United States Patent
Wang et al.

(10) Patent No.: US 11,046,715 B2
(45) Date of Patent: Jun. 29, 2021

(54) BORONIC DERIVATIVES OF HYDROXAMATES AS ANTICANCER AGENTS

(71) Applicant: Xavier University of Louisiana, New Orleans, LA (US)

(72) Inventors: Guangdi Wang, New Orleans, LA (US); Shilong Zheng, New Orleans, LA (US); Jiawang Liu, New Orleans, LA (US); Qiu Zhong, New Orleans, LA (US); Shanchun Guo, New Orleans, LA (US)

(73) Assignee: Xavier University of Louisiana, New Orleans, LA (US)

( * ) Notice: Subject to any disclaimer, the term of this patent is extended or adjusted under 35 U.S.C. 154(b) by 0 days.

(21) Appl. No.: 16/463,622

(22) PCT Filed: Nov. 27, 2017

(86) PCT No.: PCT/US2017/063322
§ 371 (c)(1),
(2) Date: May 23, 2019

(87) PCT Pub. No.: WO2018/102261
PCT Pub. Date: Jun. 7, 2018

(65) Prior Publication Data
US 2020/0181175 A1   Jun. 11, 2020

Related U.S. Application Data

(60) Provisional application No. 62/427,745, filed on Nov. 29, 2016.

(51) Int. Cl.
*C07F 5/02* (2006.01)
*A61P 35/00* (2006.01)

(52) U.S. Cl.
CPC .............. *C07F 5/025* (2013.01); *A61P 35/00* (2018.01)

(58) Field of Classification Search
CPC ................................. C07F 5/025; A61P 35/00
USPC ........................................................... 514/64
See application file for complete search history.

(56) References Cited

U.S. PATENT DOCUMENTS

| | | | |
|---|---|---|---|
| 7,829,742 | B2 | 11/2010 | Kahn et al. |
| 2011/0312905 | A1 | 12/2011 | Cohen et al. |

FOREIGN PATENT DOCUMENTS

| | | |
|---|---|---|
| CN | 106046028 A | 10/2016 |
| WO | 2010110545 A2 | 9/2010 |
| WO | 2015137887 A1 | 9/2015 |

OTHER PUBLICATIONS

International Search Report for PCT/US2017/063322, dated Sep. 21, 2018.
Zhang, Y. et al., "Benzoxaborole antimalarial agents, Part 2: Discovery of fluoro-substituted 7-(2-carboxyethyl)-1,3-dihydro-1-hydroxy-2,1benzoxaboroles" Bioorganic & Medicial Chemistry Letters. (2012) vol. 22: 1299-1307.

*Primary Examiner* — Kristin A Vajda
(74) *Attorney, Agent, or Firm* — McBee Moore & Vanik, IP, LLC

(57) ABSTRACT

The present disclosure relates to boronic derivatives of hydroxamate compounds, methods for making the same, methods for use as a monotherapy or in combination with one or more other therapeutic agents, for treatment of proliferative diseases such as cancer. The present disclosure also teaches the utilization of said boronic derivatives of hydroxamates as epigenetic therapy medications with enhanced bioavailability, lower-toxicity, and longer-lasting efficacy.

19 Claims, 12 Drawing Sheets

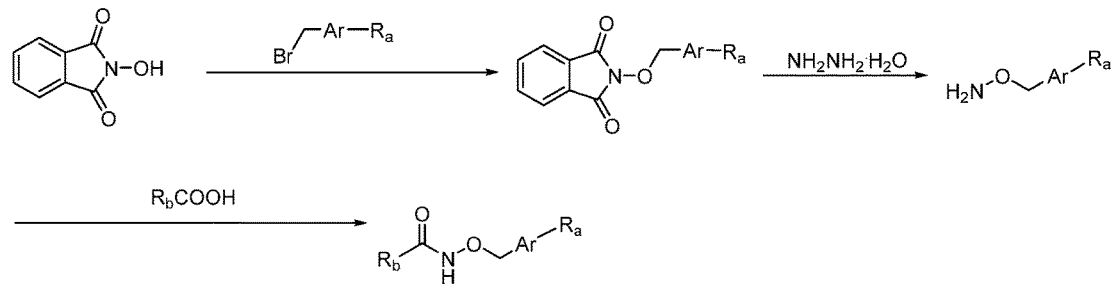

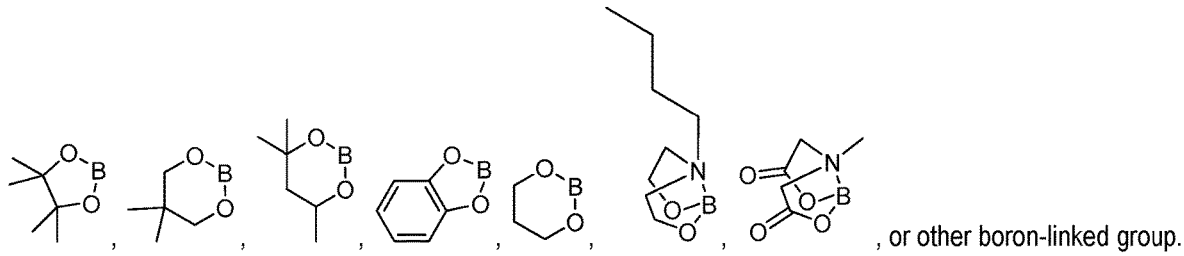

wherein R$_a$ is:

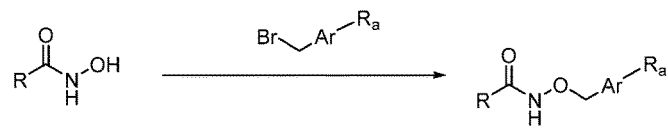

, or other boron-linked group.

wherein Ar is a substituted or unsubstituted aryl, or heteroacryl, and
wherein the R$_b$ substituent is a residue of hydroxamic acid derivative.

FIG. 1A

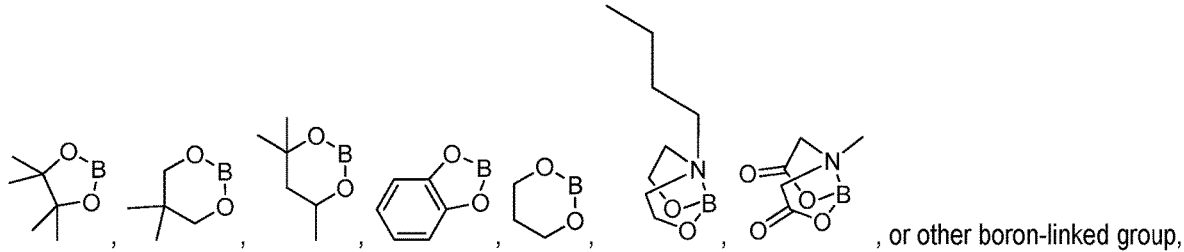

wherein R$_a$ is:

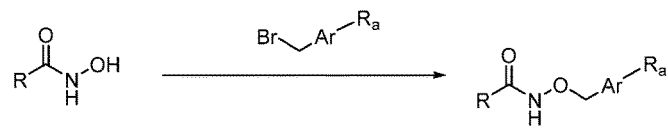

, or other boron-linked group, wherein Ar is a substituted or unsubstituted aryl, or heteroacryl, and
wherein the R$_b$ substituent is a residue of hydroxamic acid derivative.

FIG. 1B

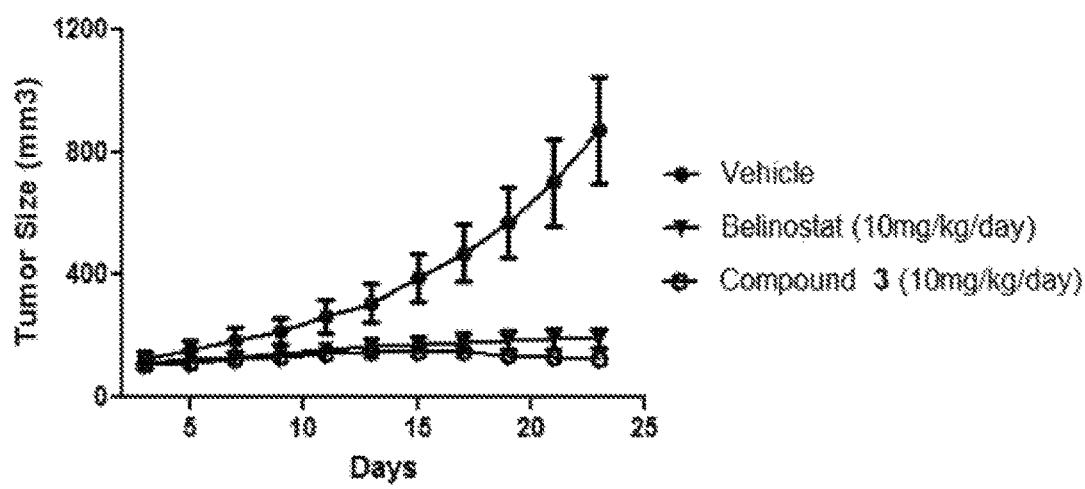
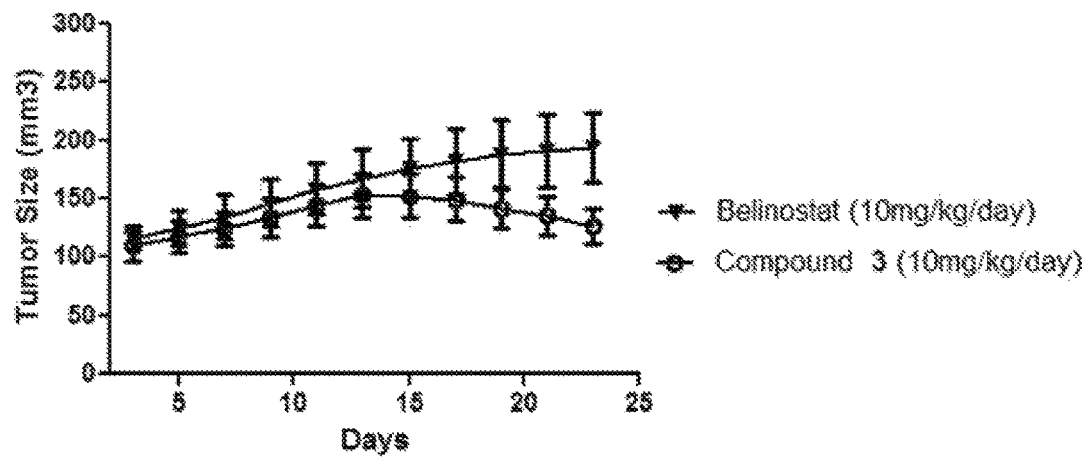
FIG. 16

BORONIC DERIVATIVES OF HYDROXAMATES AS ANTICANCER AGENTS

CROSS-REFERENCE TO RELATED APPLICATIONS

This application is the National Stage entry of International Application No. PCT/US17/63322, filed 27 Nov. 2017, which claims the benefit of U.S. Provisional Application No. 62/427,745, filed on 29 Nov. 2016.

STATEMENT REGARDING FEDERALLY SPONSORED RESEARCH OR DEVELOPMENT

This invention was made with government support under grant number 2G12MD007595 awarded by the National Institute on Minority Health and Health Disparities (NIMHD). The government has certain rights in the invention.

BACKGROUND

1. Field

The present disclosure relates to boronic derivatives of hydroxamate compounds, methods for making the same, methods for use as a monotherapy or in combination with one or more other therapeutic agents, for treatment of proliferative diseases such as cancer. Further, the present disclosure teaches the utilization of said boronic derivatives of hydroxamates as epigenetic therapy medications with enhanced bioavailability, lower-toxicity, and longer-lasting efficacy.

2. Description of Related Art

Certain compounds that inhibit histone deacetylases—known as histone deacetylase inhibitors (HDIs) and which often possess hyroxamate strucutre—are useful chemotherapeutic compounds and may be combined with other chemotherapeutic compounds. Uses include treatment and/or prophylaxis of lymphomas (e.g., for example, chronic lymphocytic leukemia, multiple myeloma, cutaneous T cell lymphoma, acute myeloid leukemia, and non-Hodgkin's lymphoma) as well as solid tumors. The clinical benefits of these compounds, however, is diminished by reduced bioavailability. Thus, a need exists for improvement of such therapeutic compounds.

BRIEF SUMMARY

Use of the novel boronic derivatives of hydroxamate compounds can provide sustained high bioavailability to exert superior therapeutic efficacy for solid tumors by their unique capability of seeking out tumor cells via molecular recognition. Therefore, the novel compounds disclosed herein can be useful in treating a substantially widened spectrum of neoplastic types, including hematological malignancies and solid tumors.

The present application provides a method to prepare and use boronic derivatives of hydroxamate molecules for the purpose of improved bioavailability, prolonged retention in patients' body, especially in the blood circulatory system. Selected examples of such compounds have been tested in vitro and in vivo to have potent anti-cancer efficacies. The compounds were found to potently inhibit cancer cell growth when cells are treated with submicromolar concentrations of the compounds. SC (subcutaneous injection) doses of the boronic hydroxamate derivatives administered to mice were found to inhibit the growth of xenograft tumor transplanted from drug-resistant cancer cells. Consequently, the boronic derivatives of hydroxamate compounds address an important need in the art to develop bioavailable, efficacious anticancer agents.

Thus, in an embodiment, the boron-containing hydroxamate derivatives of the present disclosure are compounds of Formula (I):

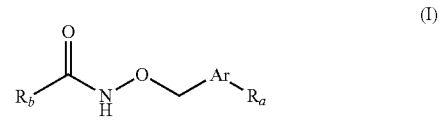

wherein:

$R_a$ is:

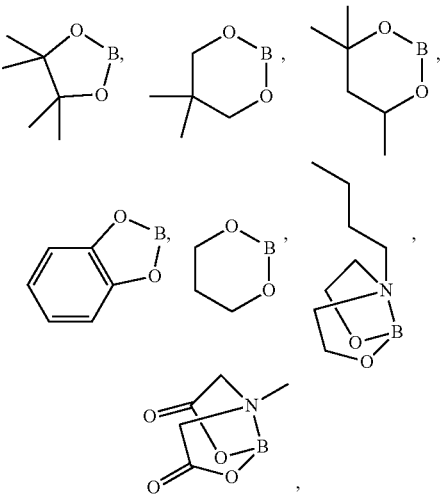

$KF_3B$, $(HO)_2B$, $NaF_3B$, or other boron-linked groups;

Ar is a substituted or unsubstituted aryl, or heteroaryl; and $R_b$ is a residue of hydroxamic acid derivative histone deacetylase inhibitor.

The structures are depicted more fully by the example compound structures of Table 6 below.

In Formulas II-X, XIa, XIb, XIIa, XIIb, and XIII-XXXVIII below, Ar and $R_a$ are as defined above for Formula (I).

In an embodiment, the boron-containing hydroxamate derivatives of the present disclosure are compounds of Formula (II):

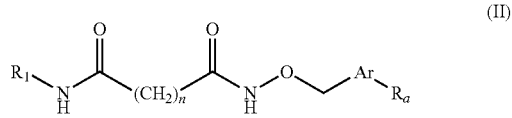

wherein:

$R_1$ is a substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; and n is 2, 3, 4, 5, 6, 7, 8.

In an embodiment, the boron-containing hydroxamate derivatives of the present disclosure are compounds of Formula (III) or Formula (IV):

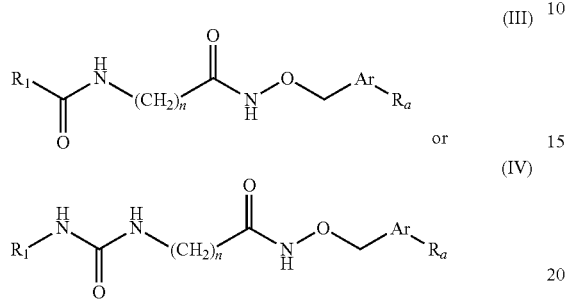

wherein:

$R_1$ is a substituted or unsubstituted aryl, arylalkyl, naphthyl, cycloalkyl, cycloalkylamino, pyridineamino, piperidino, 2-pyridinyl, 3-pyridinyl, 4-pyridinyl, thiazolyl, 9-purine-6-amino, thiazoleamino, hydroxyl, branched or unbranched alkyl, alkenyl, alkyloxy, aryloxy, arylalkyloxy, pyridyl, quinolinyl or isoquinolinyl; and n is 2, 3, 4, 5, 6, 7, or 8.

In an embodiment, the boron-containing hydroxamate derivatives of the present disclosure are compounds of Formula (V):

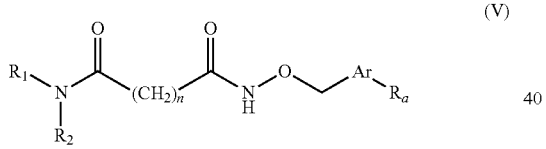

wherein:

each of $R_1$ and $R_2$ are independently the same as or different from each other and are a hydrogen atom, a hydroxyl group, a substituted or unsubstituted, branched or unbranched alkyl, alkenyl cycloalkyl, aryl, heterocyclyl, heteroaryl, alkylcycloalkyl, alkylaryl, arylalkyl, alkylheterocyclyl, alkylheteroaryl, arylalkyloxy, or aryloxy; and n is 2, 3, 4, 5, 6, 7, or 8.

In an embodiment, the boron-containing hydroxamate derivatives of the present disclosure are compounds of Formula (VI) or Formula (VII):

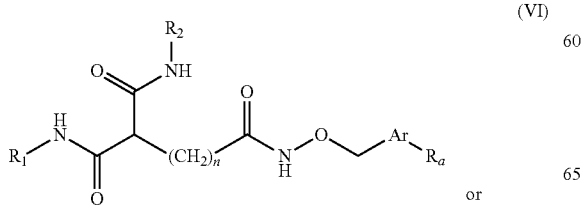

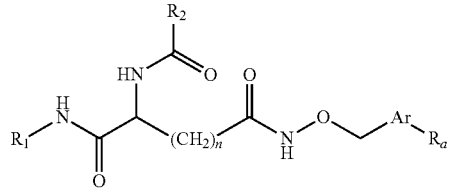

wherein each of $R_1$ and $R_2$ are independently the same as or different from each other and are a hydrogen atom, a hydroxyl group, a substituted or unsubstituted, branched or unbranched alkyl, alkenyl cycloalkyl, aryl, heterocyclyl, heteroaryl, alkylcycloalkyl, alkylaryl, arylalkyl, alkylheterocyclyl, alkylheteroaryl, arylalkyloxy, or aryloxy; and n is 2, 3, 4, 5, 6, 7, or 8.

In an embodiment, the boron-containing hydroxamate derivatives of the present disclosure are compounds of Formula (VIII):

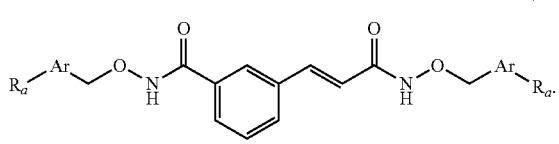

In an embodiment, the boron-containing hydroxamate derivatives of the present disclosure are compounds of Formula (IX) or Formula (X):

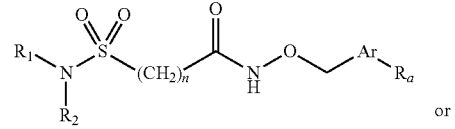

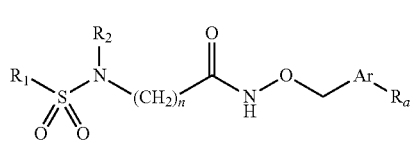

wherein:

each of $R_1$ and $R_2$ are independently the same as or different from each other and are a hydrogen atom, a substituted or unsubstituted phenyl, benzyl, phenylalkyl, naphthyl, naphthylalkyl, 2-pyridinyl, 2-pyridinylalkyl, 3-pyridinyl, 3-pyridinylalkyl, 4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl or isoquinolinyl; and n is 2, 3, 4, 5, 6, 7, or 8.

In an embodiment, the boron-containing hydroxamate derivatives of the present disclosure are compounds of Formula (XIa) or Formula (XIIa):

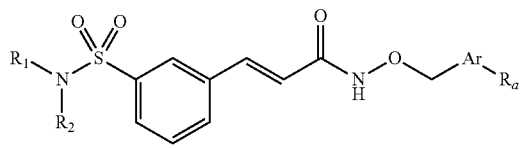

(XIa)

or

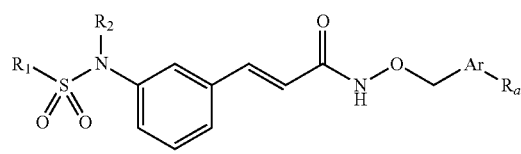

(XIIa)

wherein:

each of $R_1$ and $R_2$ are independently the same as or different from each other and are a hydrogen atom, a substituted or unsubstituted phenyl, benzyl, phenylalkyl, naphthyl, naphthylalkyl, 2-pyridinyl, 2-pyridinylalkyl, 3-pyridinyl, 3-pyridinylalkyl, 4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl, or isoquinolinyl.

In an embodiment, the boron-containing hydroxamate derivatives of the present disclosure are compounds of Formula (XIb) or Formula (XIIb):

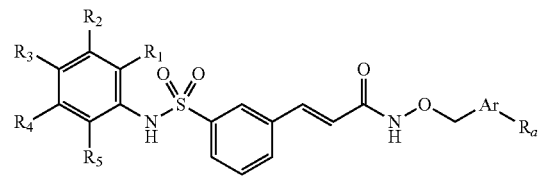

(XIb)

or

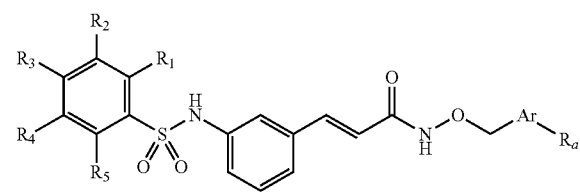

(XIIb)

wherein:

each of $R_1$, $R_2$, $R_3$, $R_4$, and $R_5$ are independently the same as or different from each other and are a hydrogen atom, methyl, methoxy, phenyl, chloro, bromo, fluoro, iodo, difluoromethyl, trifluoromethyl, difluoromethoxy, trifluoromethoxy, nitro, nitrile, acetyl, acyl, alkylthio, isopropyl, isobutyl, tert-butyl, a substituted or unsubstituted phenyl, benzyl, phenylalkyl, naphthyl, naphthylalkyl, 2-pyridinyl, 2-pyridinylalkyl, 3-pyridinyl, 3-pyridinylalkyl, 4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl, or isoquinolinyl.

In an embodiment, the boron-containing hydroxamate derivatives of the present disclosure are compounds of Formula (XIII) or Formula (XIV):

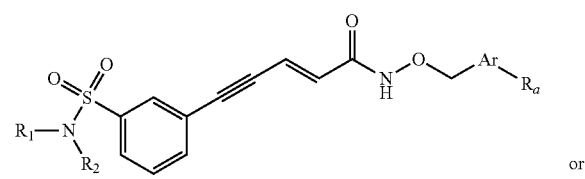

(XIII)

or

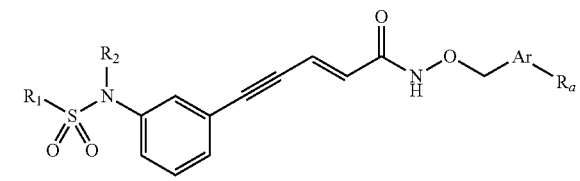

(XIV)

wherein:

each of $R_1$ and $R_2$ are independently the same as or different from each other and are a hydrogen atom, a substituted or unsubstituted phenyl, benzyl, phenylalkyl, naphthyl, naphthylalkyl, 2-pyridinyl, 2-pyridinylalkyl, 3-pyridinyl, 3-pyridinylalkyl, 4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl, or isoquinolinyl.

In an embodiment, the boron-containing hydroxamate derivatives of the present disclosure are compounds of Formula (XV):

(XV)

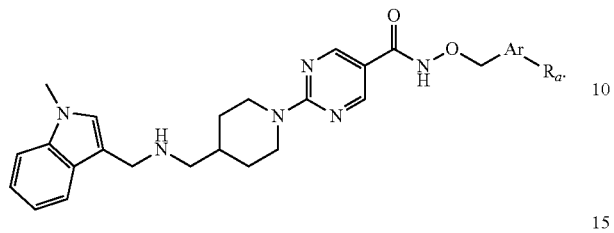

In an embodiment, the boron-containing hydroxamate derivatives of the present disclosure are compounds of Formula (XVI):

(XVI)

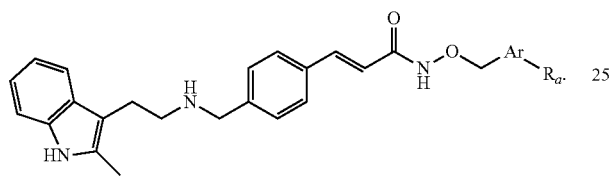

In an embodiment, the boron-containing hydroxamate derivatives of the present disclosure are compounds of Formula (XVII):

(XVII)

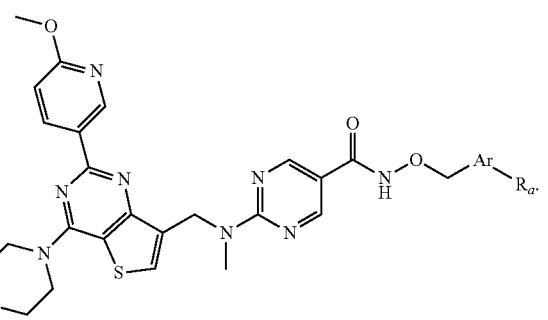

In an embodiment, the boron-containing hydroxamate derivatives of the present disclosure are compounds of Formula (XVIII):

(XVIII)

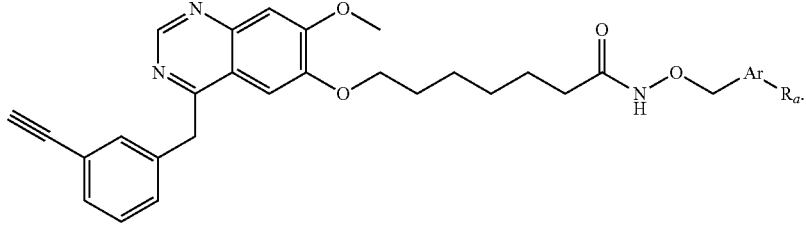

In an embodiment, the boron-containing hydroxamate derivatives of the present disclosure are compounds of Formula (XIX):

(XIX)

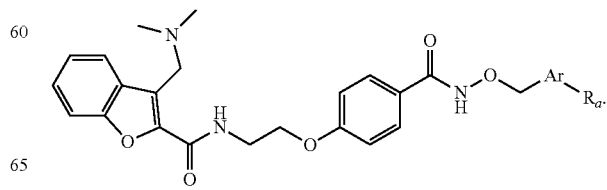

In an embodiment, the boron-containing hydroxamate derivatives of the present disclosure are compounds of Formula (XX):

(XX)

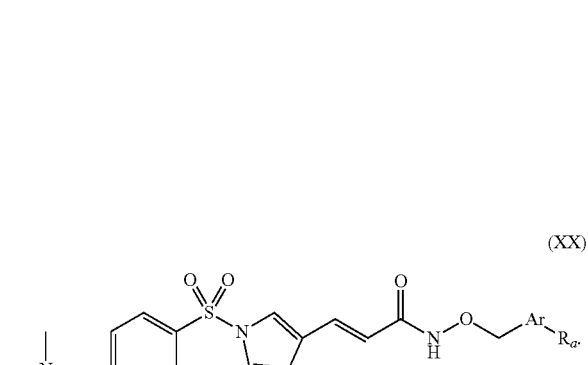

In an embodiment, the boron-containing hydroxamate derivatives of the present disclosure are compounds of Formula (XXI):

(XXI)

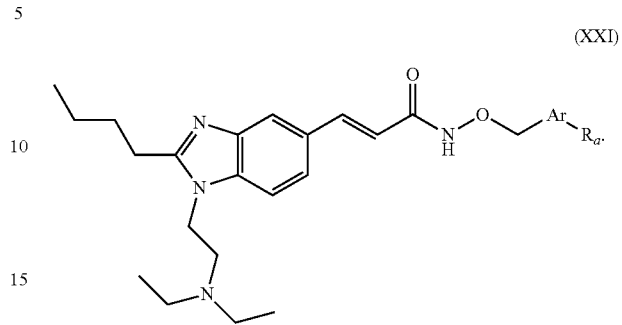

In an embodiment, the boron-containing hydroxamate derivatives of the present disclosure are compounds of Formula (XXII):

(XXII)

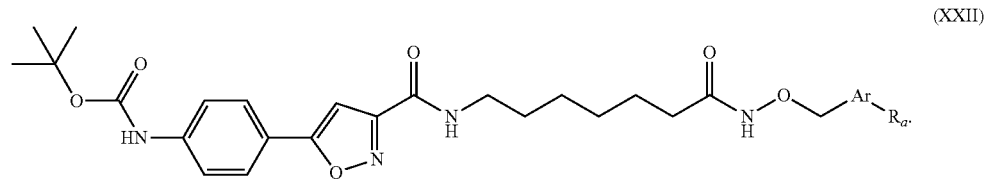

In an embodiment, the boron-containing hydroxamate derivatives of the present disclosure are compounds of Formula (XXIII):

(XXIII)

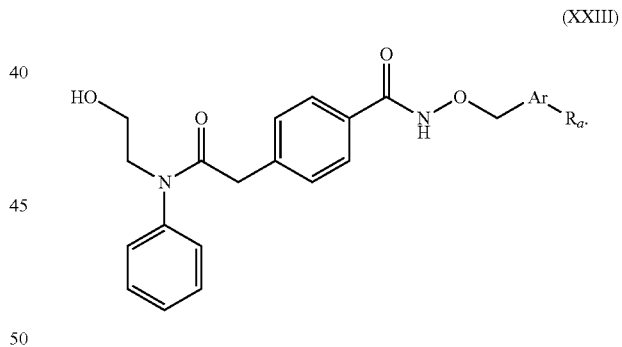

In an embodiment, the boron-containing hydroxamate derivatives of the present disclosure are compounds of Formula (XXIV):

(XXIV)

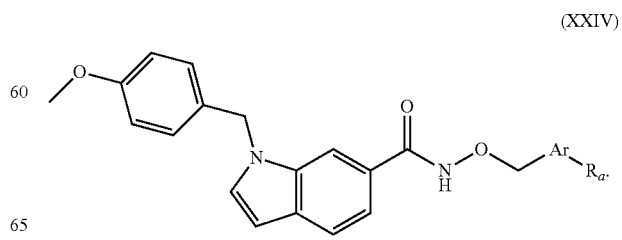

In an embodiment, the boron-containing hydroxamate derivatives of the present disclosure are compounds of Formula (XXV):

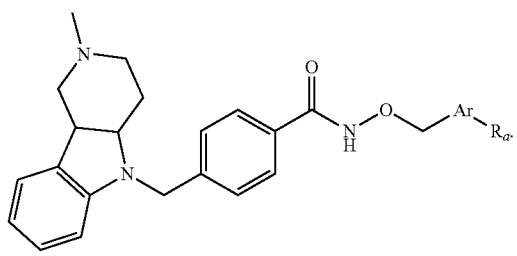

(XXV)

In an embodiment, the boron-containing hydroxamate derivatives of the present disclosure are compounds of Formula (XXVI):

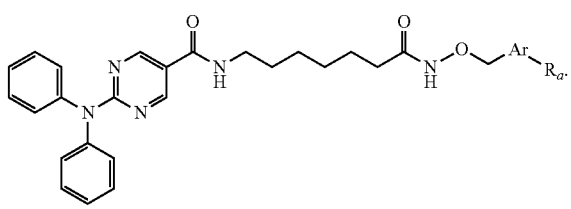

(XXVI)

In an embodiment, the boron-containing hydroxamate derivatives of the present disclosure are compounds of Formula (XXVII):

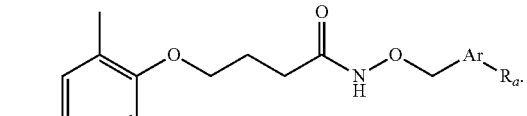

(XXVII)

In an embodiment, the boron-containing hydroxamate derivatives of the present disclosure are compounds of Formula (XXVIII):

(XXVIII)

In an embodiment, the boron-containing hydroxamate derivatives of the present disclosure are compounds of Formula (XXIX):

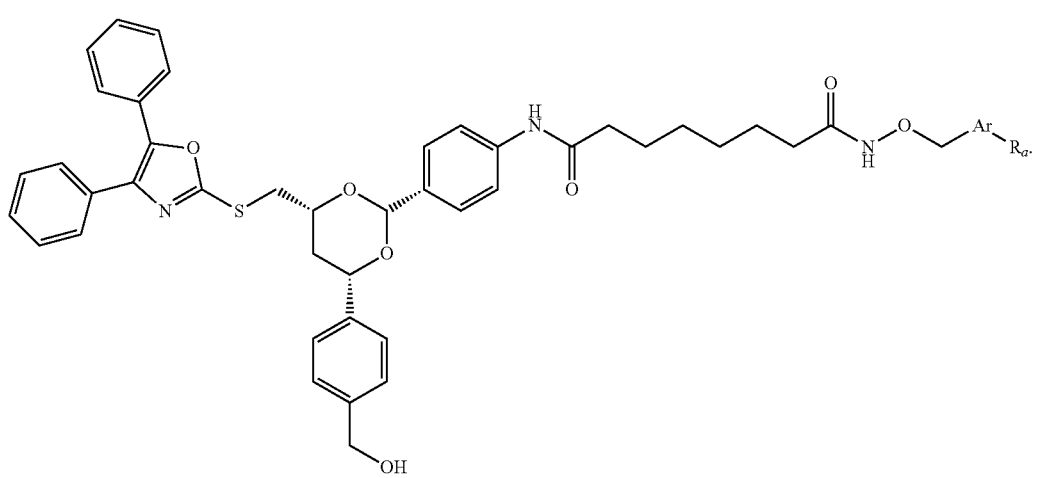

(XXIX)

In an embodiment, the boron-containing hydroxamate derivatives of the present disclosure are compounds of Formula (XXX):

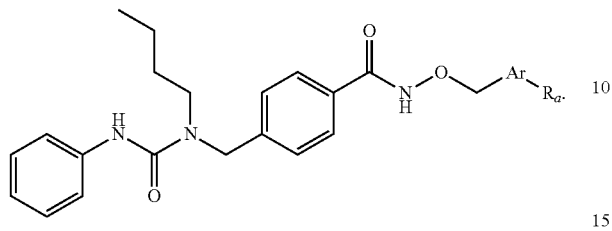

(XXX)

In an embodiment, the boron-containing hydroxamate derivatives of the present disclosure are compounds of Formula (XXXI):

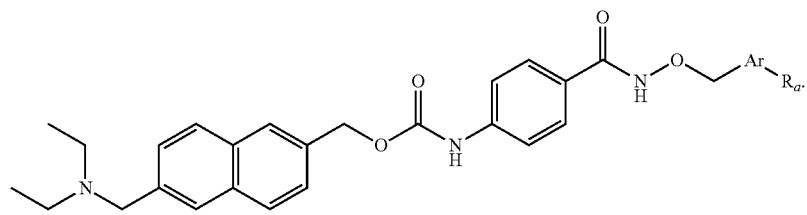

(XXXI)

In an embodiment, the boron-containing hydroxamate derivatives of the present disclosure are compounds of Formula (XXXII):

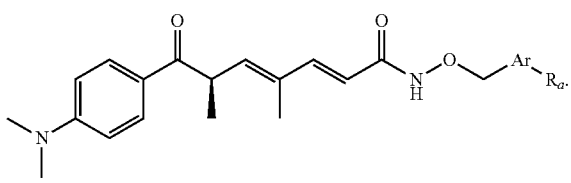

(XXXII)

In an embodiment, the boron-containing hydroxamate derivatives of the present disclosure are compounds of Formula (XXXIII):

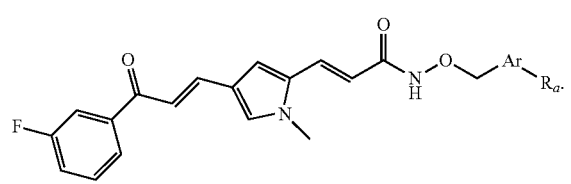

(XXXIII)

In an embodiment, the boron-containing hydroxamate derivatives of the present disclosure are compounds of Formula (XXXIV):

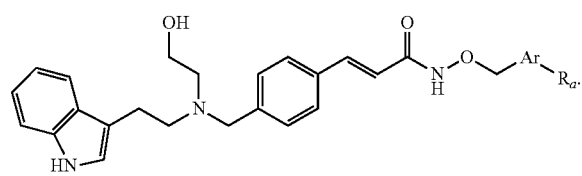

(XXXIV)

In an embodiment, the boron-containing hydroxamate derivatives of the present disclosure are compounds of Formula (XXXV):

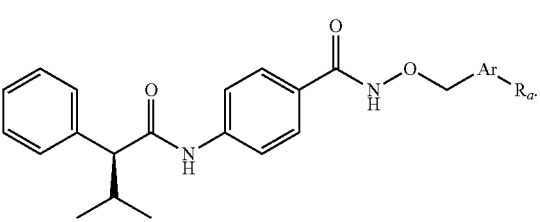

(XXXV)

In an embodiment, the boron-containing hydroxamate derivatives of the present disclosure are compounds of Formula (XXXVI):

(XXXVI)

In an embodiment, the boron-containing hydroxamate derivatives of the present disclosure are compounds of Formula (XXXVII):

(XXXVII)

In an embodiment, the boron-containing hydroxamate derivatives of the present disclosure are compounds of Formula (XXXVIII):

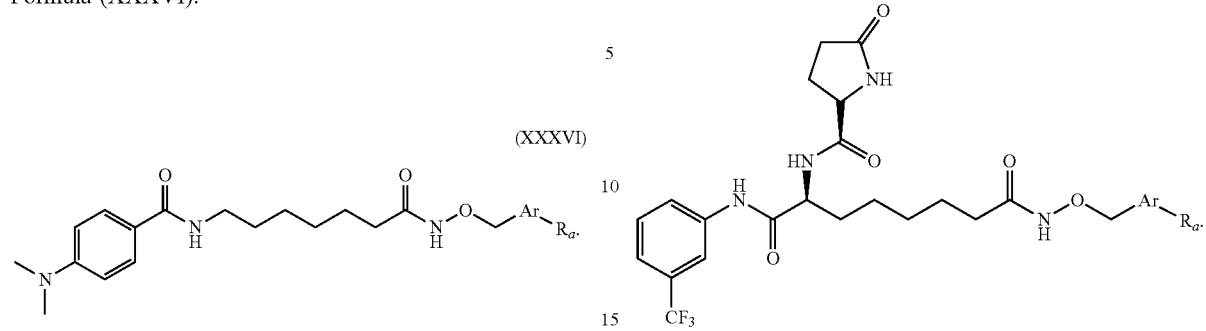

(XXXVIII)

Of Formulas I-X, XIa, XIb, XIIa, XIIb, and XIII-XXXVIII, preferably, $R_a$ is:

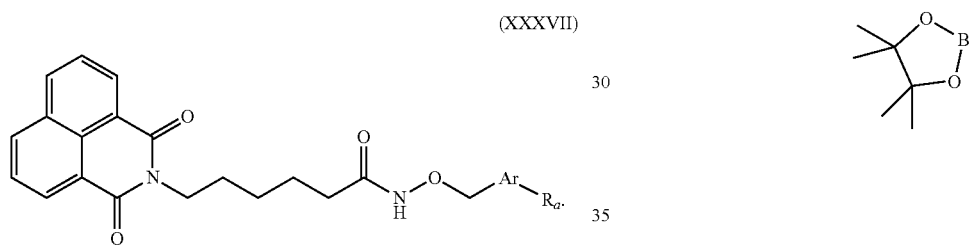

or $(OH)_2B$.

In a preferred embodiment, the boronic derivative is Compound 1:

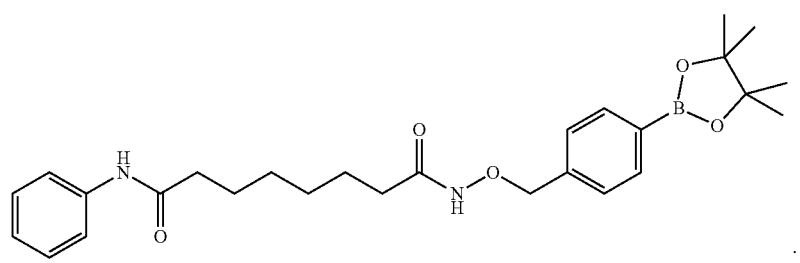

Compound 1

In a preferred embodiment, the boronic derivative is Compound 2:
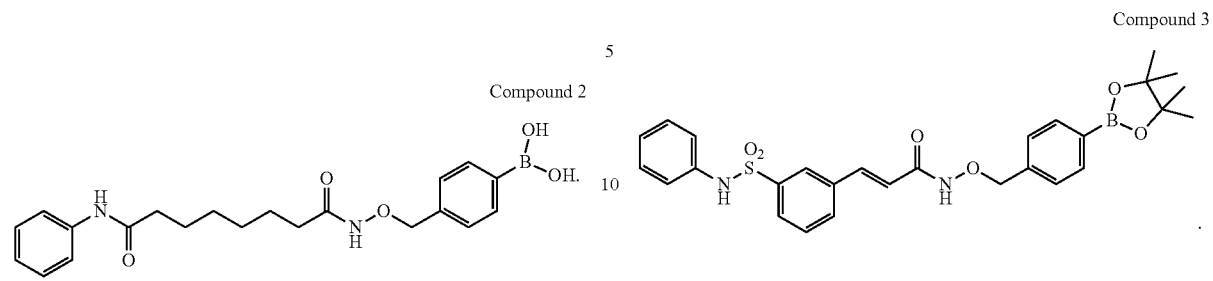
In a preferred embodiment, the boronic derivative is Compound 3:
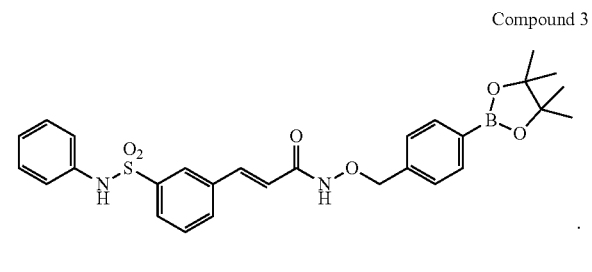 [SMILES: CC1(C)OB(c2ccc(CONC(=O)/C=C/c3cccc(S(=O)(=O)Nc4ccccc4)c3)cc2)OC1(C)C]
In a preferred embodiment, the boronic derivative is Compound 4:
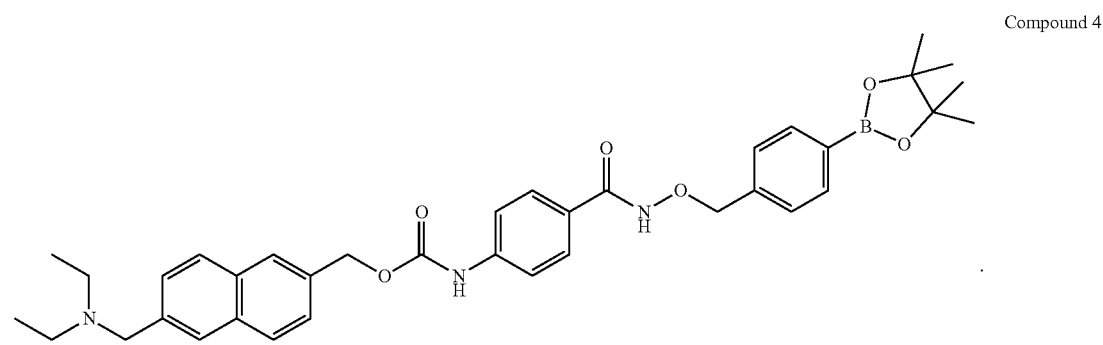 [SMILES: CCN(CC)Cc1ccc2cc(COC(=O)Nc3ccc(C(=O)NOCc4ccc(B5OC(C)(C)C(C)(C)O5)cc4)cc3)ccc2c1]
In a preferred embodiment, the boronic derivative is Compound 5:
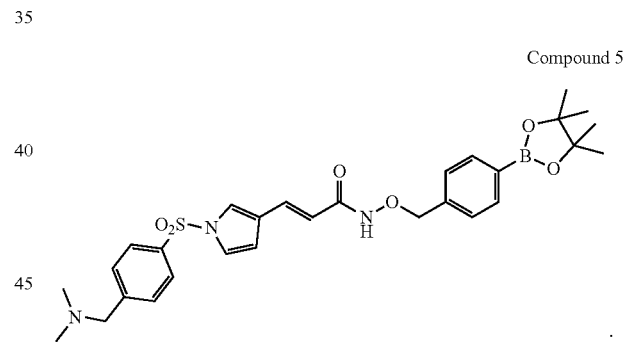
In a preferred embodiment, the boronic derivative is Compound 6:
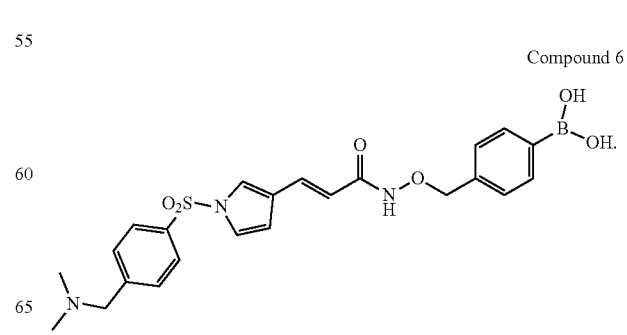

In a preferred embodiment, the boronic derivative is Compound 7:

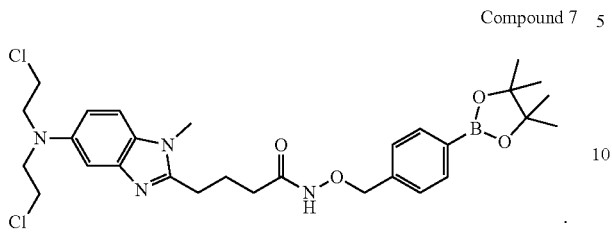

Compound 7

In a preferred embodiment, the boronic derivative is Compound 8:

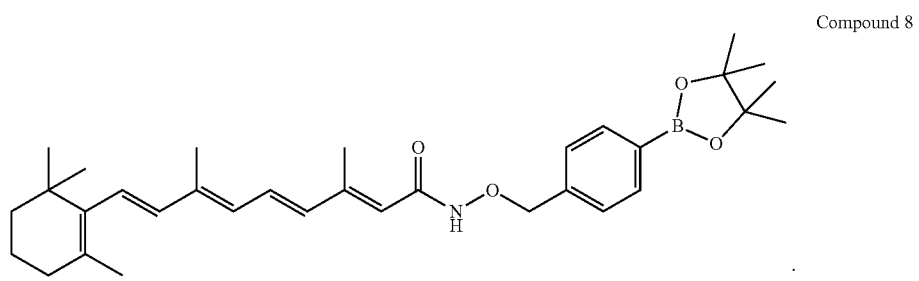 [SMILES: CC1=C(/C=C/C(C)=C/C=C/C(C)=C/C(=O)NOCc2ccc(B3OC(C)(C)C(C)(C)O3)cc2)C(C)(C)CCC1]

Compound 8

In a preferred embodiment, the boronic derivative is Compound 9:

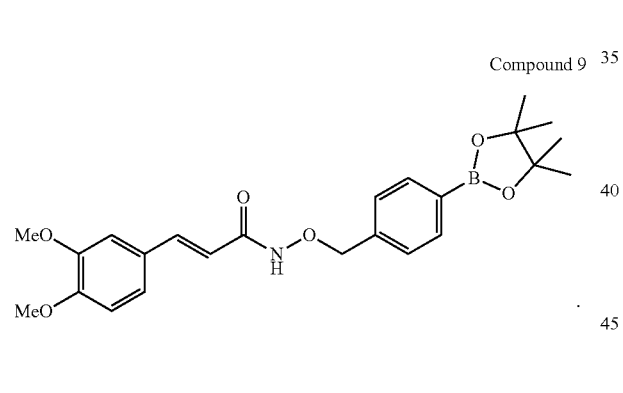

Compound 9

In a preferred embodiment, the boronic derivative is Compound 10:

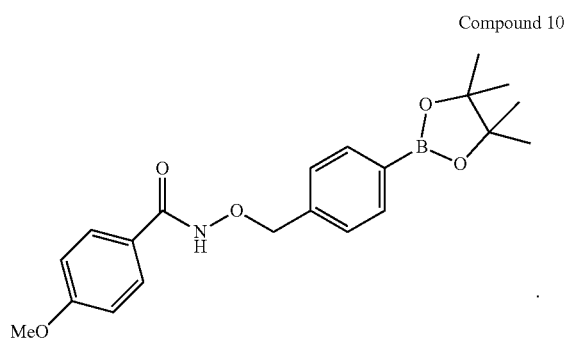 [SMILES: COc1ccc(C(=O)NOCc2ccc(B3OC(C)(C)C(C)(C)O3)cc2)cc1]

Compound 10

In a preferred embodiment, the boronic derivative is Compound 11:

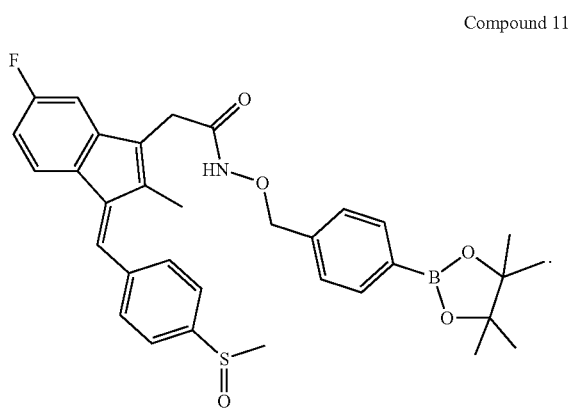 [SMILES: CC1=C(CC(=O)NOCc2ccc(B3OC(C)(C)C(C)(C)O3)cc2)c2cc(F)ccc2/C1=C/c1ccc(S(C)=O)cc1]

Compound 11

In a preferred embodiment, the boronic derivative is Compound 12:

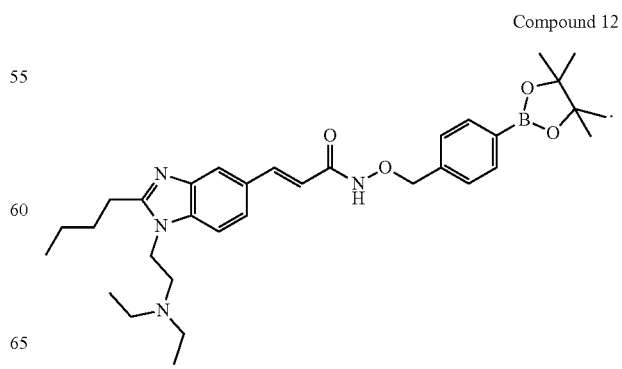

Compound 12

In a preferred embodiment, the boronic derivative is Compound 13:

Compound 13

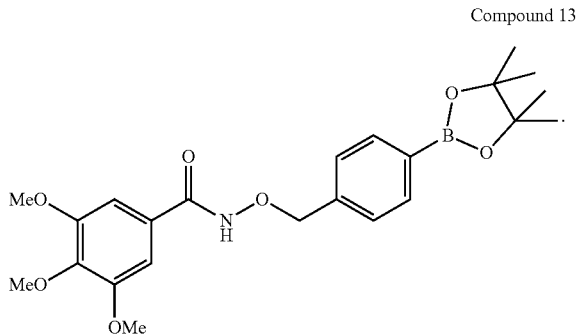 [SMILES: COc1cc(C(=O)NOCc2ccc(B3OC(C)(C)C(C)(C)O3)cc2)cc(OC)c1OC]

In a preferred embodiment, the boronic derivative is Compound 14:

Compound 14

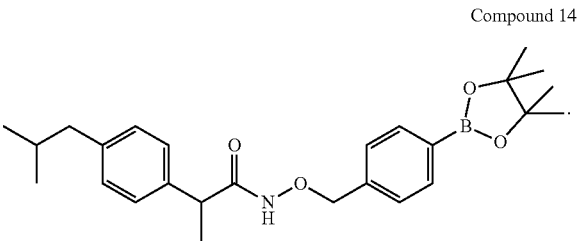 [SMILES: CC(C)Cc1ccc(C(C)C(=O)NOCc2ccc(B3OC(C)(C)C(C)(C)O3)cc2)cc1]

In a preferred embodiment, the boronic derivative is Compound 15:

Compound 15

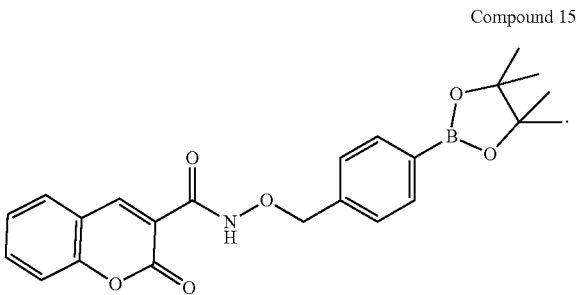 [SMILES: CC1(C)OB(c2ccc(CONC(=O)c3cc4ccccc4oc3=O)cc2)OC1(C)C]

In a preferred embodiment, the boronic derivative is Compound 16:

Compound 16

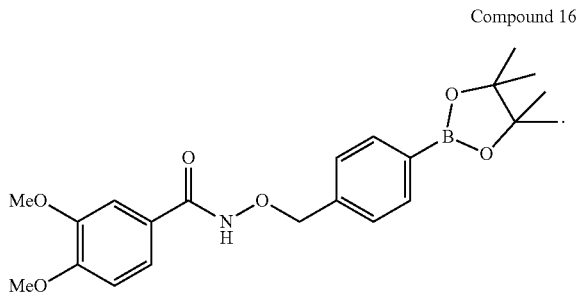 [SMILES: COc1ccc(C(=O)NOCc2ccc(B3OC(C)(C)C(C)(C)O3)cc2)cc1OC]

In an embodiment, the disclosure provides for a pharmaceutical composition in the form of at least one boronic derivative of hydroxamate for treatment of proliferative diseases and/or symptoms. The composition may comprise at least one boronic derivative of hydroxamate in an amount that is therapeutically effective.

The disclosure therefore relates to use of a boronic hydroxamate derivatives according to Formula I and/or the related Formula I compounds denoted by Formulas II-X, XIa, XIb, XIIa, XIIb, and XIII-XXXVIII), or combinations thereof, for treatment of proliferative diseases and/or symptoms such as cancer and cystic fibrosis.

The pharmaceutical compositions of the present disclosure can be in any form known to those of skill in the art. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravenous, intradermal, intramuscular, and subcutaneous administration. The pharmaceutical compositions disclosed herein may also further comprise carriers, binders, diluents, and excipients.

Also, in other aspects, the present disclosure relates to new boronic derivatives of hydroxamate compounds and their pharmaceutically acceptable salts; pharmaceutical compositions comprising the new boronic derivatives of hydroxamate compounds, either alone or in combination with at least one additional therapeutic agent, with a pharmaceutically acceptable carrier; and uses of the new boronic derivatives of hydroxamate compounds, either alone or in combination with at least one additional therapeutic agent, in the treatment of proliferative diseases and/or symptoms including cancer and cystic fibrosis. The combination with an additional therapeutic agent may take the form of combining the new boronic derivatives of hydroxamate compounds with any known therapeutic agent.

It is a further object of the disclosure to provide boronic derivatives of hydroxamate compounds, methods of synthesizing the boronic derivatives of hydroxamate compounds, methods of manufacturing the boronic derivatives of hydroxamate compounds, and methods of using the boronic derivatives of hydroxamate compounds.

Another object of the disclosure is to provide a composition, for example a pharmaceutical composition, comprising at least one boronic derivative of hydroxamate compounds in an amount effective for an indication, including but not limited to primary tumor, treatment of recurrent cancer, treatment of metastatic cancer that may or may not be resistant to other cancer therapies.

A further object of the disclosure is a kit, comprising a composition containing at least one boronic derivative of hydroxamate compounds for treatment of cancer or other indications. The composition of the kit may comprise at least one carrier, at least one binder, at least one diluent, at least one excipient, at least one other therapeutic agent, or mixtures thereof.

The methods for treating a clinical indication by the boronic derivatives of hydroxamate compounds disclosed herein, may be effectuated by administering a therapeutically effective amount of the drug to a patient in need thereof, this therapeutically effective amount may comprise administration of the prodrug to the patient at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, or about 10 mg/kg/day to about 100 mg/kg/day are also contemplated.

In certain aspects, the at least one boron-based prodrug analog has a purity of ≥75%, ≥80%, ≥85%, ≥90%, ≥95%, ≥96%, ≥97%, or ≥98%, and preferably ≥99%.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following description, claims, and accompanying drawings explained below.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIGS. 1A & 1B show general synthetic schemes for preparation of boronic derivatives of hydroxamate compounds according to Formula (I).

FIG. 16 shows inhibition of tumor growth in an MCF-7 tumor xenograft model in mice. (A) Tumor volumes of the vehicle, belinostat and compound 3-treated groups by subcutaneous injection. (B) The enlarged section of tumor volumes of belinostat and compound 3-treated groups.

DETAILED DESCRIPTION

Figure 2A:
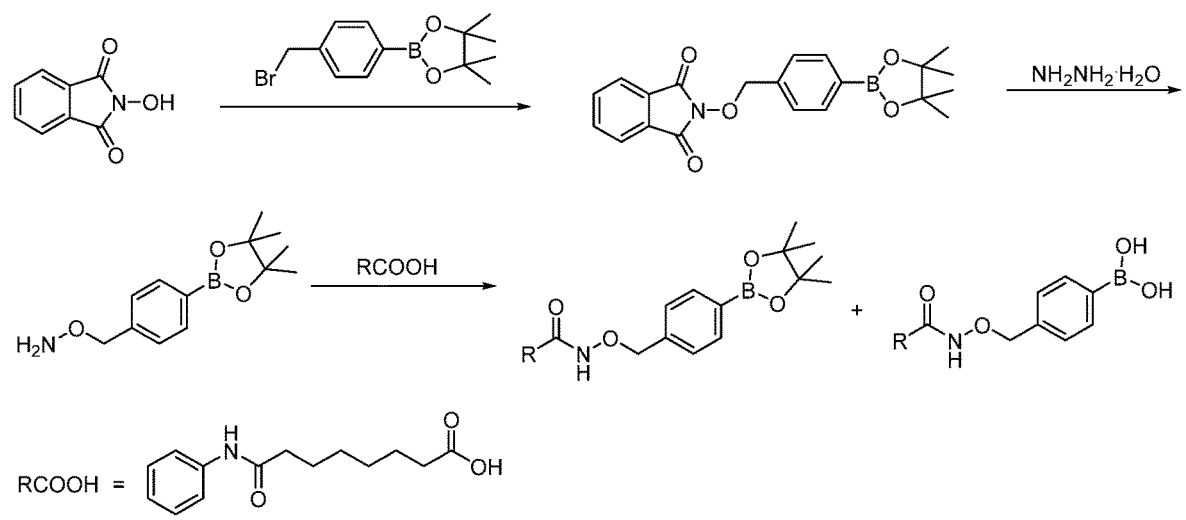
FIGS. 2A & 2B show synthetic schemes for preparation of compounds 1 and 2.
Figure 2B:
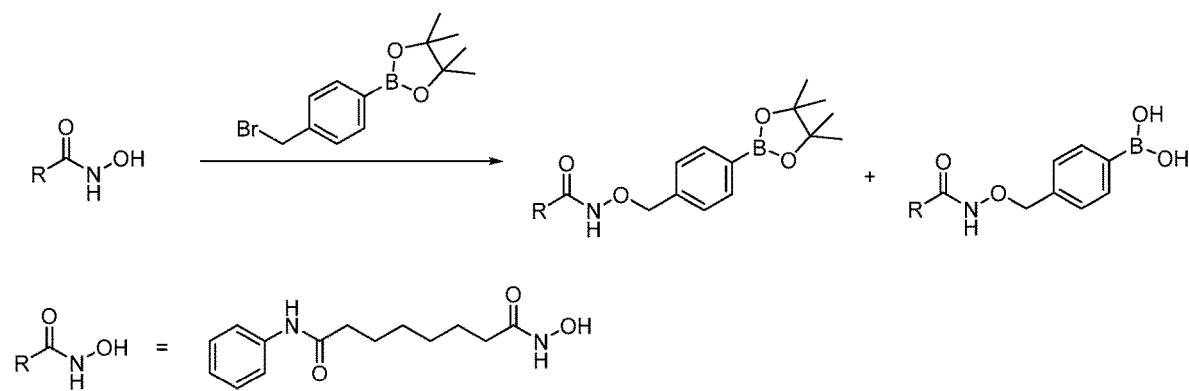
Figure 3:
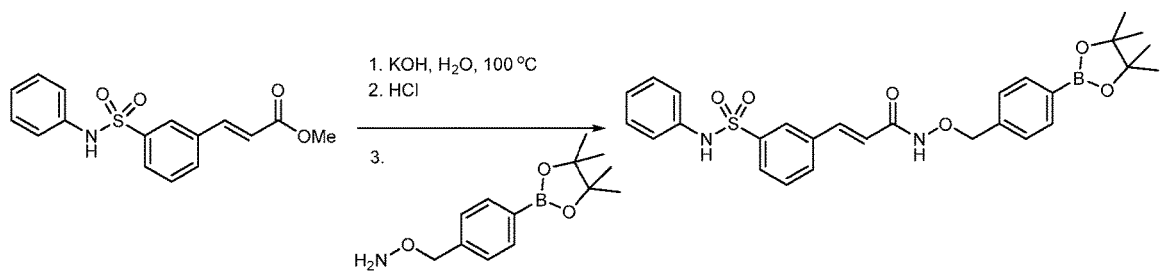
FIG. 3 shows a synthetic scheme for preparation of compound 3.
Figure 4:
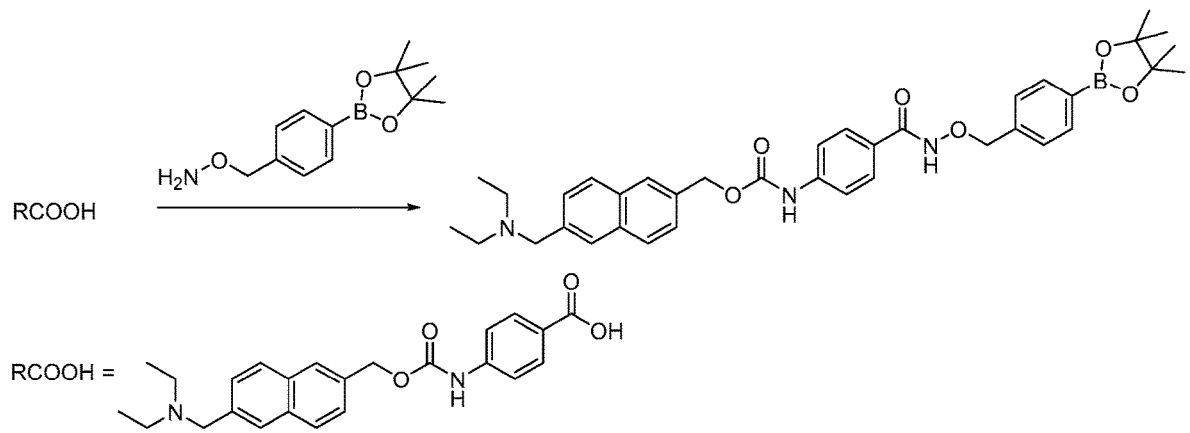
FIG. 4 shows a synthetic scheme for preparation of compound 4.
Figure 5:
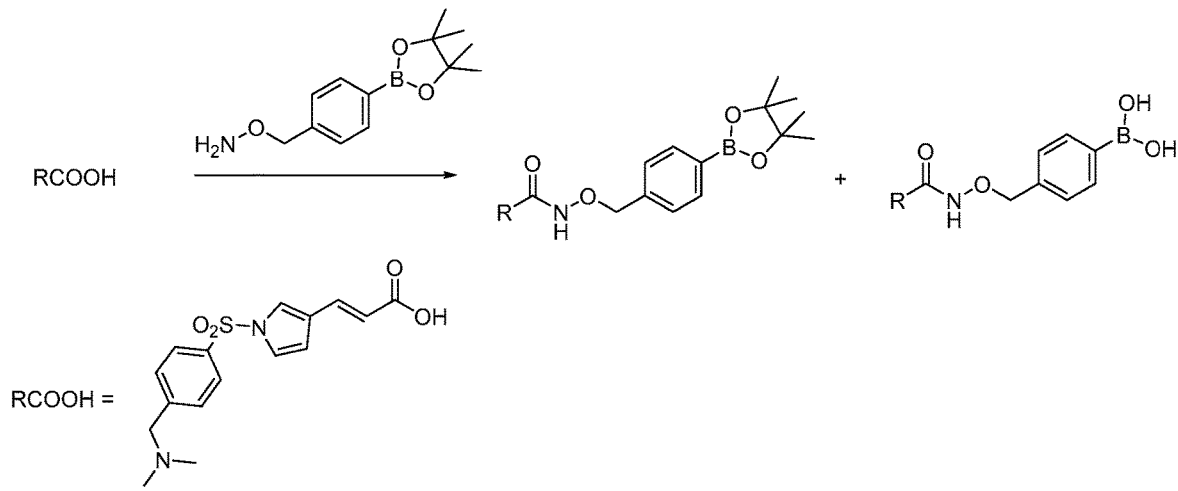
FIG. 5 shows a synthetic scheme for preparation of compound 5 and compound 6.
Figure 6:
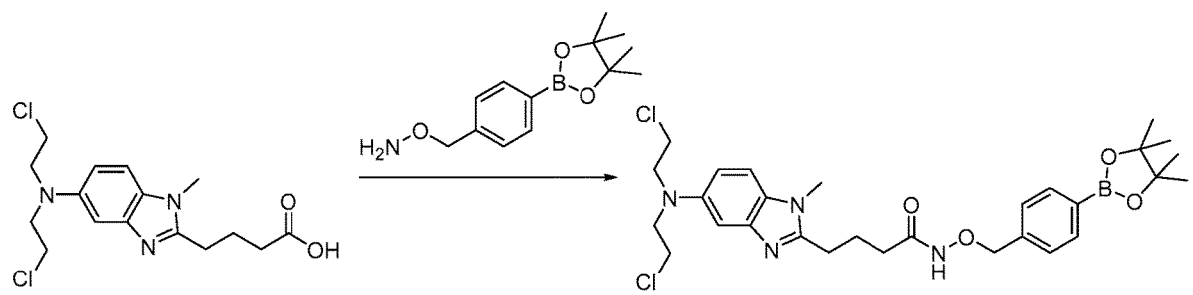
FIG. 6 shows a synthetic scheme for preparation of compound 7.
Figure 7:
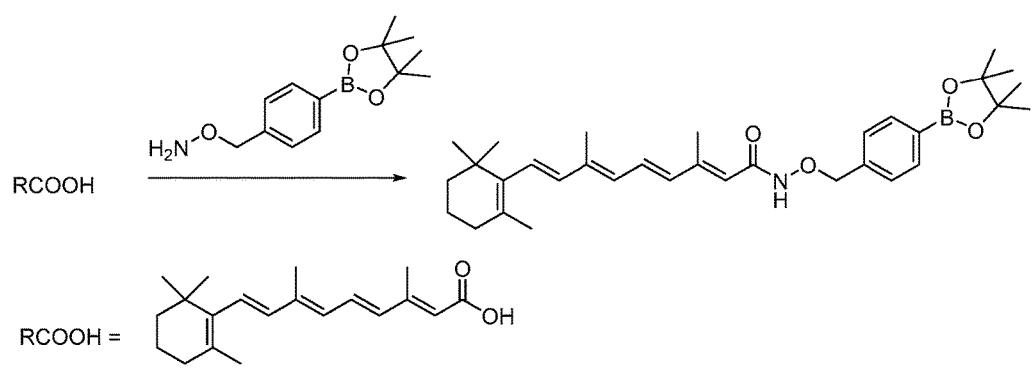
FIG. 7 shows a synthetic scheme for preparation of compound 8.
Figure 8:
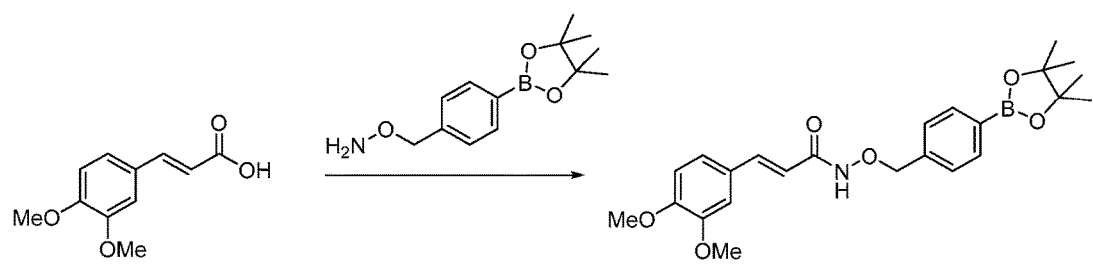
FIG. 8 shows a synthetic scheme for preparation of compound 9.
Figure 9:
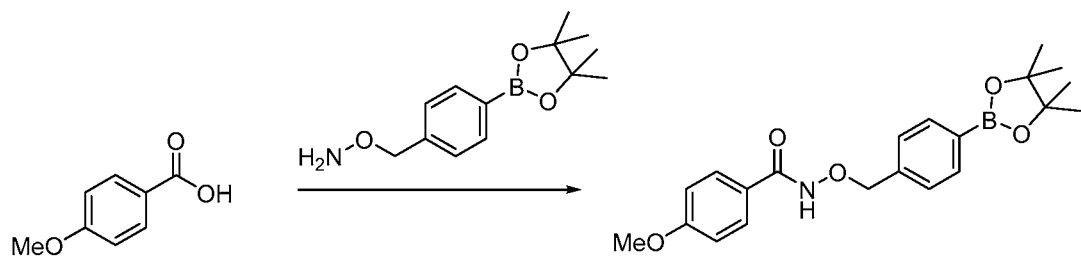
FIG. 9 shows a synthetic scheme for preparation of compound 10.
Figure 10:
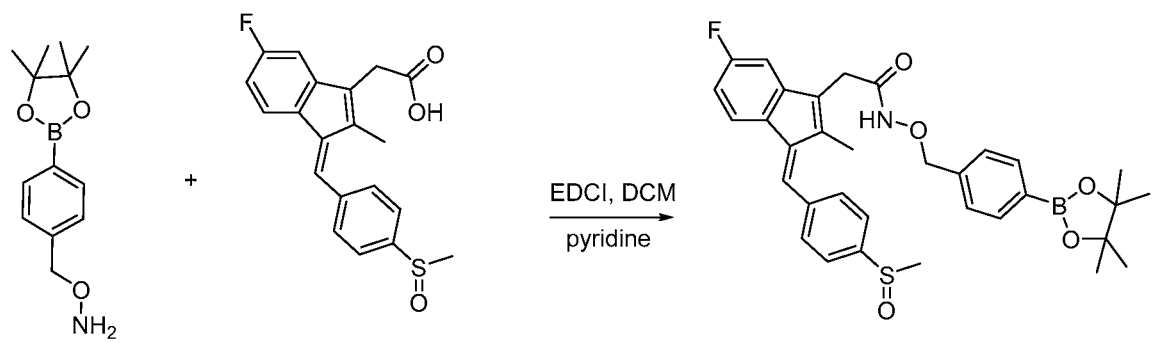
FIG. 10 shows a synthetic scheme for preparation of compound 11.
Figure 11:
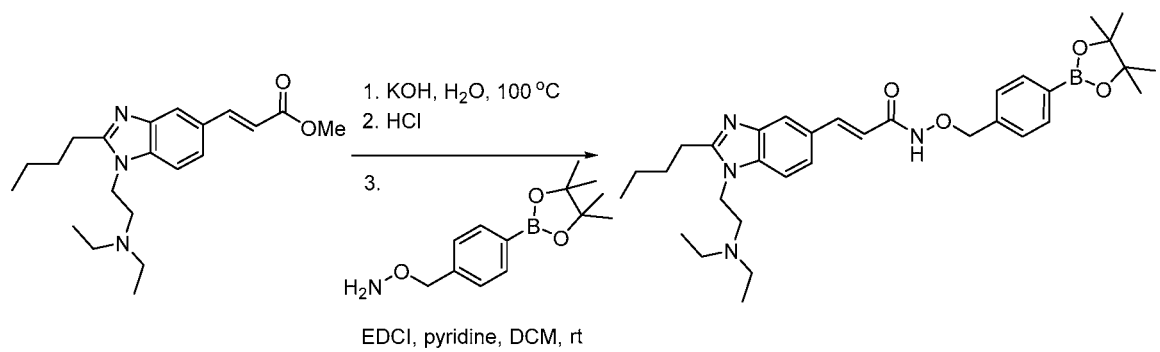
FIG. 11 shows a synthetic scheme for preparation of compound 12.
Figure 12:
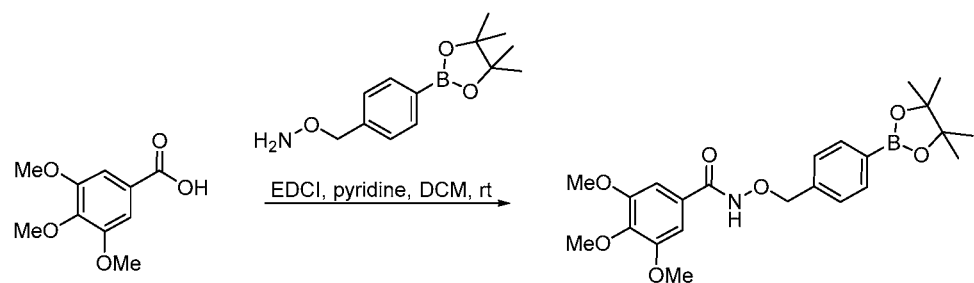
FIG. 12 shows a synthetic scheme for preparation of compound 13.
Figure 13:
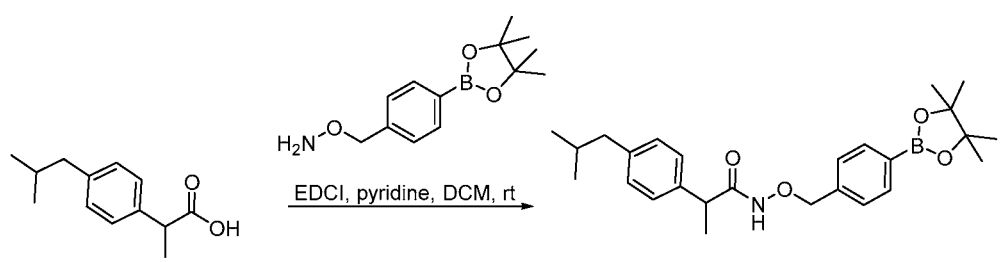
FIG. 13 shows a synthetic scheme for preparation of compound 14.
Figure 14:
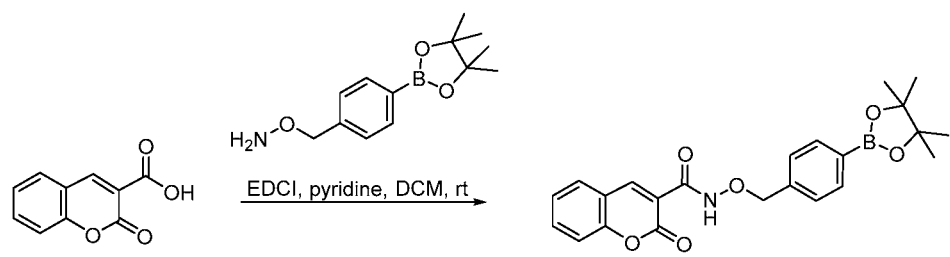
FIG. 14 shows a synthetic scheme for preparation of compound 15.
Figure 15:
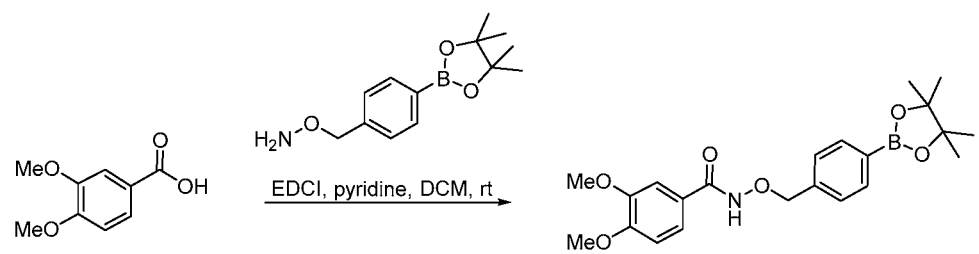
FIG. 15 shows a synthetic scheme for preparation of compound 16.
Figure 17:
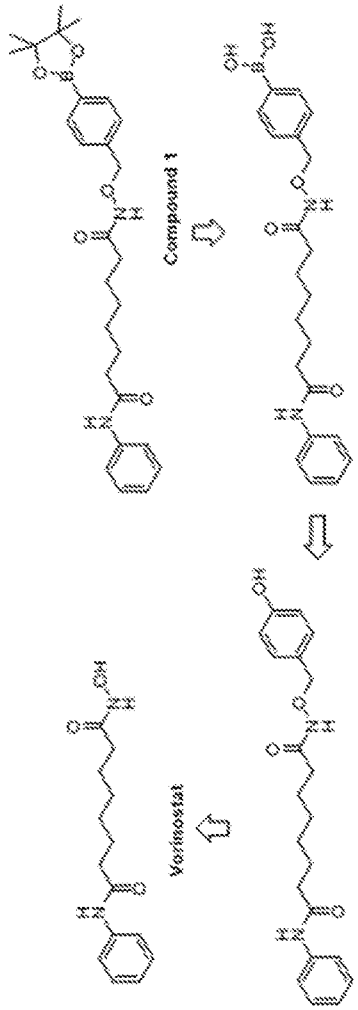
FIG. 17 shows a possible route of metabolism from compound 1 to vorinostat.
Figure 18:
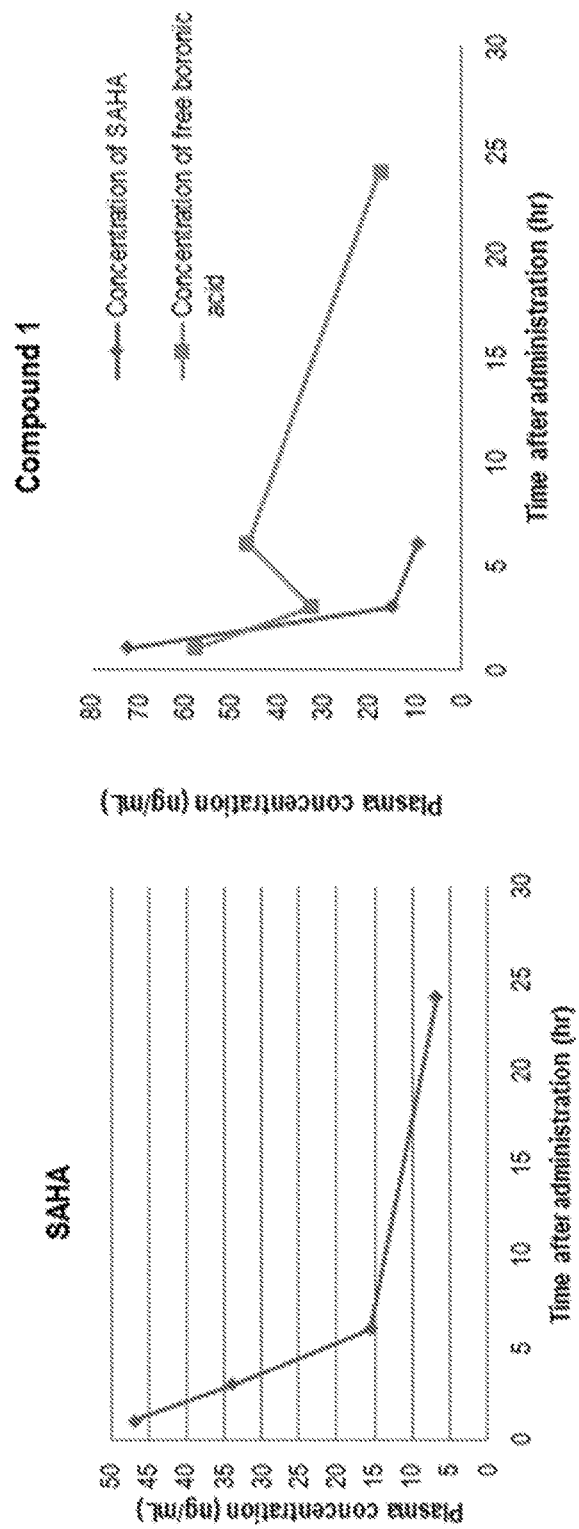
FIG. 18 shows pharmacokinetics of vorinostat (SAHA) and its boronic derivative compound 1 in rat at a single intraperitoneal dose of 10 mg/kg.
Figure 19:
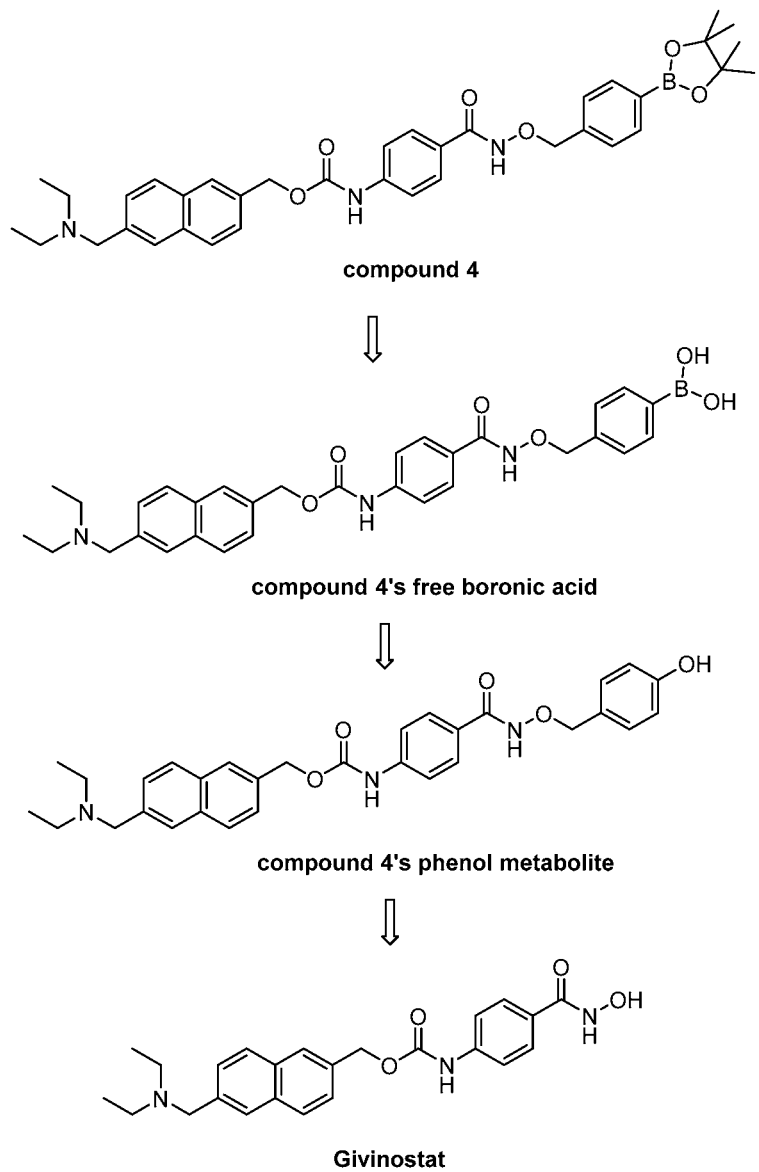
FIG. 19 shows a possible route of metabolism from compound 4 to Givinostat.
Figure 20:
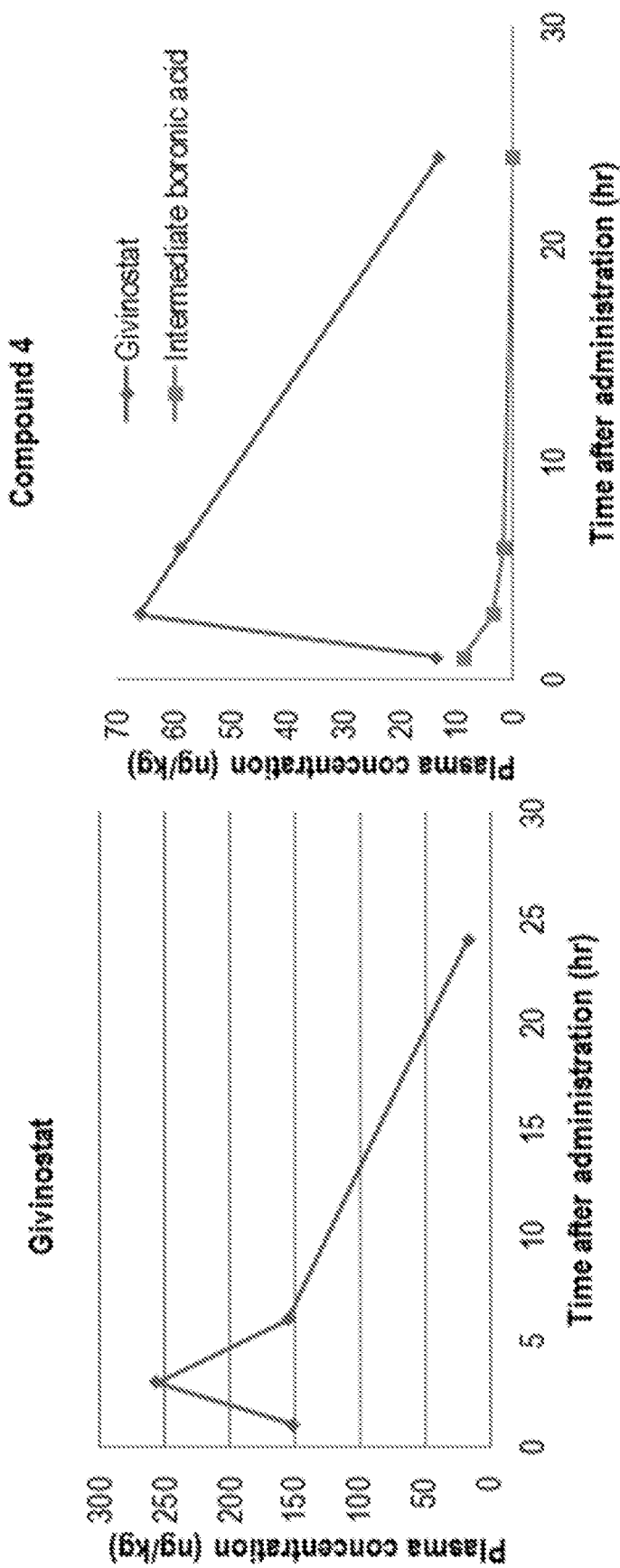
FIG. 20 shows pharmacokinetics of Givinostat and its boronic derivative compound 4 in rat at a single intraperitoneal dose of 10 mg/kg.
Figure 21:
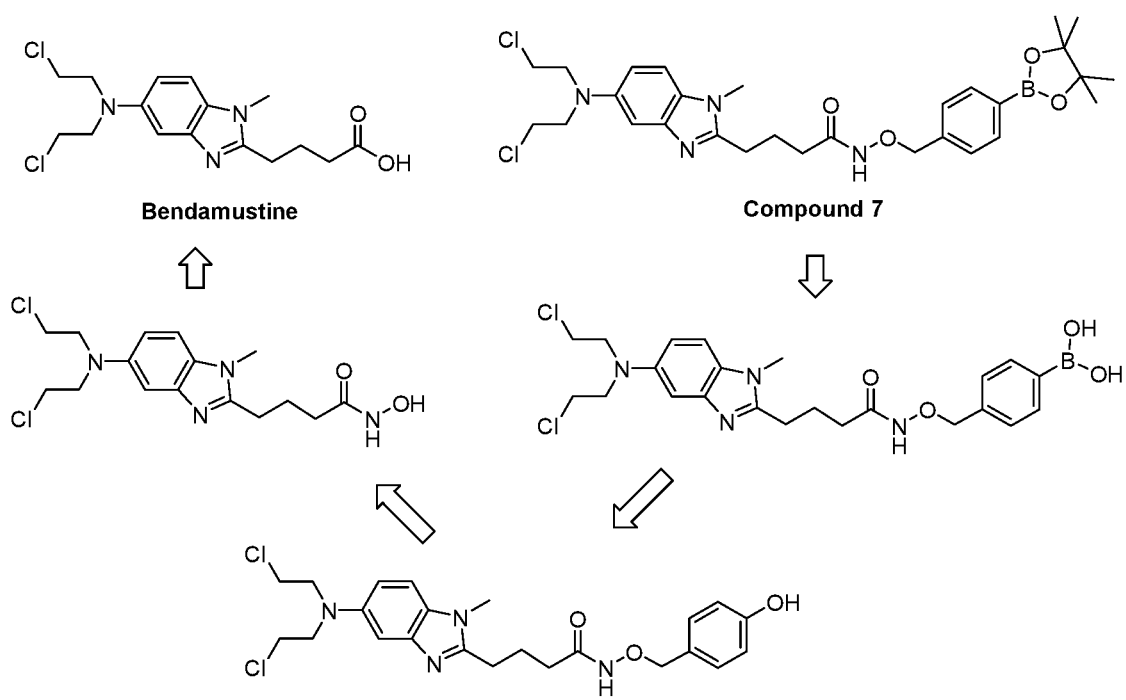
FIG. 21 shows a possible route of metabolism from compound 7 to bendamustine.
Figure 22:
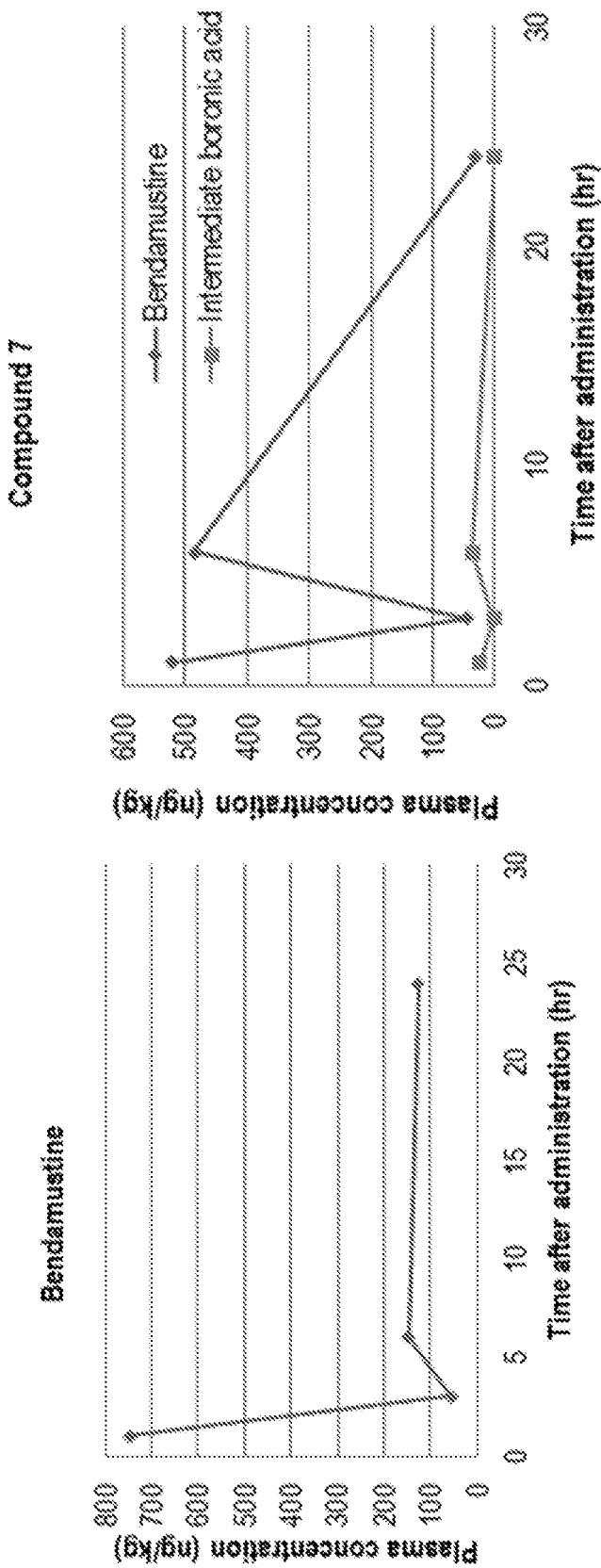
FIG. 22 shows pharmacokinetics of Bendamustine and its boronic derivative compound 7 in rat at a single intraperitoneal dose of 10 mg/kg.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

The subject disclosure features, in one aspect, the synthesis of boronic derivatives of hydroxamate compounds. To determine whether the disclosed compounds have therapeutic efficacy in vitro and in vivo, studies described below were performed.

The in vitro cytotoxicity of boronic derivatives of hydroxamates was tested against various cancer cell lines; the results are provided in Table 1.

TABLE 1

Antiproliferation activity ($IC_{50}$, μM) of boronic derivatives of hydroxamates

| | Cancer cell lines | | | | | | |
|---|---|---|---|---|---|---|---|
| Compounds | MDA-MB-231 | A549 | HeLa | SK-MEL-28 | MCF-7 | SK-OV-3 | NCI-H460 |
| Vorinostat (SAHA) | 0.201 | n.d. | n.d. | 0.482 | n.d. | 0.124 | 0.425 |
| Compound 1 | 423 | n.d. | n.d. | 13.5 | n.d. | 55.2 | n.d. |
| Belinostat | 0.0616 | 0.0766 | 0.0865 | n.d. | 0.0964 | n.d. | n.d. |
| Compound 3 | 0.303 | 0.453 | 0.273 | 0.678 | 1.46 | n.d. | 0.430 |
| Givinostat | 0.119 | n.d. | n.d. | 0.0913 | n.d. | n.d. | 0.103 |

TABLE 1-continued

Antiproliferation activity (IC$_{50}$, µM) of boronic derivatives of hydroxamates

| Compounds | Cancer cell lines | | | | | | |
|---|---|---|---|---|---|---|---|
| | MDA-MB-231 | A549 | HeLa | SK-MEL-28 | MCF-7 | SK-OV-3 | NCI-H460 |
| Compound 4 | 0.321 | n.d. | n.d. | 0.377 | n.d. | 0.296 | 0.154 |
| Compound 5 | >10 | >10 | >10 | n.d. | n.d. | n.d. | n.d. |
| Bendamustine | 37.5 | n.d. | n.d. | 149 | n.d. | 33.4 | 45.3 |
| Compound 7 | 3.33 | n.d. | n.d. | 0.373 | n.d. | 1.84 | 1.22 |
| Compound 10 | >10 | >10 | >10 | n.d. | n.d. | n.d. | n.d. |
| Sulindac | 1395 | 20400 | 458 | 1400 | n.d. | 109 | 41.9 |
| Compound 11 | 20.1 | 696 | 277 | 77.4 | n.d. | 19.4 | 1.01 |
| Compound 13 | >10 | >10 | >10 | n.d. | n.d. | n.d. | n.d. |
| Compound 14 | >10 | >10 | >10 | n.d. | n.d. | n.d. | n.d. |
| Compound 15 | >10 | >10 | >10 | n.d. | n.d. | n.d. | n.d. |
| Compound 16 | >10 | >10 | >10 | n.d. | n.d. | n.d. | n.d. | n.d.: not determined; * MDA-MB-231: human breast adenocarcinoma; A549: human non-small-cell lung carcinoma; HeLa: human epitheloid cervix carcinoma; SK-MEL-28: human melanoma; MCF-7: human breast adenocarcinoma; SK-OV-3: human ovarian cancer; NCI-H460: human non-small-cell lung cancer.

Example 1: In Vitro Pharmacokinetics of Boronic Derivatives of Hydroxamates-Pharmacokinetics of Compound 3

Cell culture media was analyzed for concentrations of compound 3 and its active form belinostat in MDA-MB-231 and HeLa cells. The results show that compound 3 rapidly hydrolyzed to its boronic acid form compound 95. Using HPLC coupled to an Orbitrap mass spectrometer, it was possible to separate, identify, and quantify compound 95 and the active form belinostat. As shown in Table 2, the concentrations of belinostat and compound 95 were measured at 30.68 and 331.79 ng/mL, respectively, in the culture media after 1-day incubation of compound 3 with MDA-MB-231 cells, indicating that compound 3 has been completely converted to compound 95 and partially to belinostat. From Day 1 to Day 6, the concentration of compound 95 decreased gradually from 331.79 to 130.91 ng/mL, while the concentration of belinostat remained nearly constant. Similar results were observed in HeLa cells, where the concentrations of belinostat and compound 95 were measured at 8.38 and 282.74 ng/mL in the media after 1-day incubation, 3.81 and 49.64 ng/mL on day 6, respectively. These results confirmed that compound 3 could be partially transformed to active belinostat, which may be the reason why compound 3 displayed differences in its cytotoxicity against cancer cell lines when compared with belinostat (Table 1).

TABLE 2

Concentration (ng/mL) of belinostat and compound 95 in culture media after incubation of compound 3 with MDA-MB-231 and HeLa cancer cell lines.

| | Compound 3 | | | |
|---|---|---|---|---|
| | MDA-MB-231 | | HeLa | |
| Day | Belinostat | Compound 95 | Belinostat | Compound 95 |
| 1 | 30.68 ± 0.40 | 331.79 ± 4.46 | 8.38 ± 0.05 | 282.74 ± 14.22 |
| 2 | 27.69 ± 1.26 | 268.49 ± 2.23 | 6.56 ± 0.11 | 147.36 ± 3.32 |
| 3 | 20.28 ± 0.54 | 246.94 ± 11.22 | 13.42 ± 0.46 | 144.94 ± 0.79 |
| 4 | 19.82 ± 0.86 | 171.79 ± 3.76 | 7.77 ± 0.09 | 106.97 ± 0.69 |
| 5 | 28.53 ± 1.01 | 145.79 ± 3.15 | 3.68 ± 0.15 | 82.71 ± 3.56 |
| 6 | 27.75 ± 0.50 | 130.91 ± 5.40 | 3.81 ± 0.17 | 49.64 ± 0.93 |

±: standard error (SEM) of triplicate experiments

Example 2: Anti-HDAC Activity of Boronic Derivatives of Hydroxamates-HDAC Inhibitory Activity of Compound 3

Histone deacetylase (HDAC) inhibitory activity of compound 3 was investigated with the histone deacetylase activity assay kit (Fluorometric) ab156064 (Abcam, Cambridge, UK). As shown in Table 3, compound 3 displays an EC$_{50}$ value of 0.35 µM after 20 min incubation following the protocol for the assay kit, which is higher than the EC$_{50}$ values (0.18 and 0.031 µM) of vorinostat and belinostat. The difference in EC$_{50}$ values among compound 3, vorinostat, and belinostat is consistent with their difference in IC$_{50}$ values against cancer cell lines (Table 1), which suggests that the cytotoxicity of compound 3 may also be related to its HDAC inhibitory activity. These results are expected by design in that release of the active drug belinostat from the compound 3 is only partial in in vitro systems, hence the reduced potency of compound 3.

TABLE 3

HDAC inhibitory activity of compound 3

| Compounds | EC$_{50}$ (µM) |
|---|---|
| vorinostat | 0.18 |
| belinostat | 0.031 |
| compound 3 | 0.35 |

Example 3: In Vivo Efficacy Assay and Pharmacokinetics of Boronic Derivatives of Hydroxamates in Mice—In Vivo Efficacy of Compound 3

The in vivo efficacy of compound 3 in mice was investigated. A head-to-head study with a dosage of 10 mg/kg/day of compound 3 and belinostat by subcutaneous injection in an MCF-7 tumor xenograft model in mice was designed to test the tumor inhibitory efficacy of the two compounds. The results in FIG. 16 (panel A) demonstrate that both belinostat and compound 3 have potent inhibitory activity against the growth of tumor compared with the increase of tumor volume in the vehicle group. In the enlarged view of tumor growth curves displayed in FIG. 16 (panel B), the difference in tumor growth between the treatment groups of compound 3 and belinostat becomes clear after two weeks' dosing at 10 mg/kg. Compound 3 treatment not only inhibited the growth of tumor but also resulted in tumor remission in this tumor xenograft model. In the belinostat treatment group, average tumor volume continued its slow increase from 167 mm$^3$ at day 15 to 194 mm$^3$ at day 24, whereas tumor volume in mice treated with compound 3 decreased from 153 mm$^3$ to 127 mm$^3$ in the same period of time. Moreover, due to its heavier molecular weight, the molar concentration of compound 3 is lower than belinostat given at the same dosage in mg/kg, which adds to the observed efficacy of compound 3.

Taken together, these results demonstrate that compound 3 afforded significantly greater efficacy than belinostat in the in vivo assay, with 85.3% and 77.7% inhibition of tumor growth (TGI), 14.6% and 22.3% tumor volume ratio (T/C), respectively. Importantly, in all of the in vitro assays, compound 3 demonstrated a consistently lower potency than belinostat against a panel of cancer cell lines, but the dramatic reversal in the in vivo efficacy of compound 3 was seen. The statistical analysis of t-test shows that the tumor volume of the compound 3-treated group has significant difference from that of the belinostat-treated group with 0.0045 of P-Value (<0.05).

TABLE 4

Efficacy and pharmacokinetics of compound 3 against MCF-7 in mice

| Groups | Tumor volume (mm$^3$) | T/C (%) | TGI (%) | Concentration in tumor tissue (ng/g) | |
|---|---|---|---|---|---|
| | | | | belinostat | compound 95 |
| Vehicle | 869.28 ± 173.01 | NA | NA | NA | NA |
| belinostat | 193.68 ± 29.79 | 22.3 | 77.7 | 23.36 ± 1.57 | NA |
| compound 3 | 126..65 ± 15.29 | 14.6 | 85.3 | 56.95 ± 15.19 | 51.03 ± 41.96 |

NA: not available;
±: standard error of 4 mice

After 24 days of treatment with belinostat or compound 3 at a dosage of 10 mg/kg/day by subcutaneous injection, belinostat and compound 95 (the corresponding free boronic acid of compound 3) in tumor tissue of mice were analyzed and the results are shown in Table 4. For the belinostat-treated group, the concentration of belinostat in tumor tissue was 23.36 ng/g, while for the compound 3-treated group, belinostat was 56.95 ng/g, but also compound 95 was found at a concentration of 51.03 ng/g in tumor tissue. Despite low molar dosage administration of compound 3, the compound 3 group has a higher concentration of belinostat than the belinostat group in tumor tissue. When added together, the concentration of belinostat and compound 95 for the compound 3 group is five times greater than that of the belinostat group. The results confirmed that compound 3 has better bioavailability than belinostat in an MCF-7 tumor xenograft model in mice; it was also much easier than belinostat to reach deep tumor tissues. Therefore, the dramatic reversal in the in vivo efficacy of compound 3 could be attributed to its superior biocompatibility to the active site.

Example 4: In Vivo Pharmacokinetics Study of Boron-Containing Derivatives of Hydroxamates—In Vivo Pharmacokinetics of Compound 3

Pharmacokinetic studies of compound 3 in mice were conducted. After a single dose of 10 mg/kg by intraperitoneal injection (IP), blood samples were collected from mice and resulting plasma were analyzed for concentration of belinostat at 1, 3, 6, and 24 h after drug administration. The results in Table 5 show that compound 3 afforded over 172.67 ng/mL peak concentration of belinostat at 3 h after administration, a level far exceeding 25.78 ng/mL achieved by belinostat when given a single dose of 10 mg/kg by IP to mice, and even at 24 h, compound 3 group remained over 34.31 ng/ml concentration of belinostat. Moreover, PK studies revealed that the predominant form in mice plasma is compound 95 (the corresponding free boronic acid of compound 3) with belinostat accounting for only its about 10-20%, and the maximum concentration of compound 95 reached 930.77 ng/mL, about forty times of maximum concentration (25.78 ng/mL of belinostat) achieved by belinostat. These observations provide definitive evidence that the bioavailability of compound 3 is superior compared to belinostat.

TABLE 5

Pharmacokinetics of compound 3 and belinostat in mice after intraperitoneal injection (IP)

| | Compound 3 | | Belinostat |
|---|---|---|---|
| Time (h) | Belinostat (ng/mL) | Compound 95 (ng/mL) | Belinostat (ng/mL) |
| 1 | 3.16 ± 0.13 | 36.75 ± 2.22 | 20.94 ± 1.73 |
| 3 | 172.67 ± 3.25 | 930.77 ± 28.91 | 25.78 ± 1.62 |
| 6 | 72.54 ± 2.94 | 367.62 ± 25.81 | 14.28 ± 0.74 |
| 24 | 34.31 ± 2.62 | 229.35 ± 11.68 | 5.32 ± 0.16 |

±: standard error (SEM) of 3 mice

As used herein, the term "minimize" or "reduce", or derivatives thereof, include a complete or partial inhibition of a specified biological effect (which is apparent from the context in which the terms "minimize" or "reduce" are used).

Examples of boronic derivatives of hydroxamate compounds are provided by Formulas 1 through 118 of Table 6.

TABLE 6
| Compound No. | Molecular formula | Structure |
| --- | --- | --- |
| Compound 1 | C₂₇H₃₇BN₂O₅ | 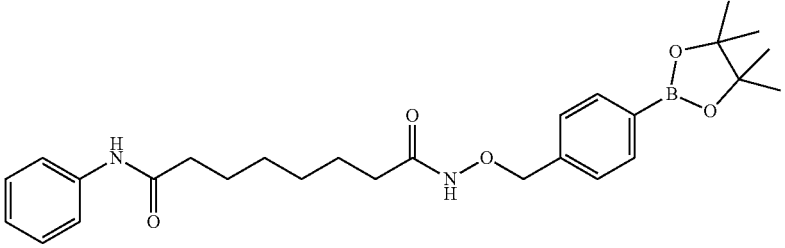 [SMILES: CC1(C)OB(c2ccc(CONC(=O)CCCCCCC(=O)Nc3ccccc3)cc2)OC1(C)C] |
| Compound 2 | C₂₁H₂₇BN₂O₅ | 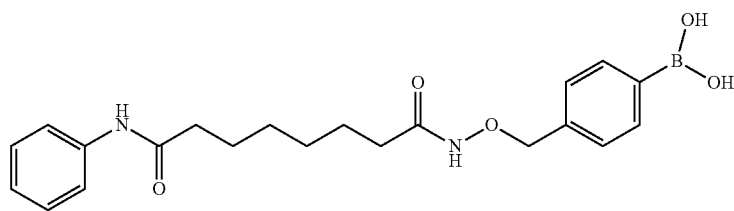 [SMILES: O=C(CCCCCCC(=O)Nc1ccccc1)NOCc1ccc(B(O)O)cc1] |
| Compound 3 | C₂₈H₃₁BN₂O₆S | 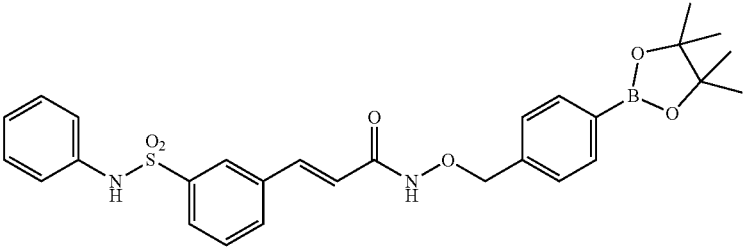 [SMILES: CC1(C)OB(c2ccc(CONC(=O)/C=C/c3cccc(S(=O)(=O)Nc4ccccc4)c3)cc2)OC1(C)C] |
| Compound 4 | C₃₇H₄₄BN₃O₆ | 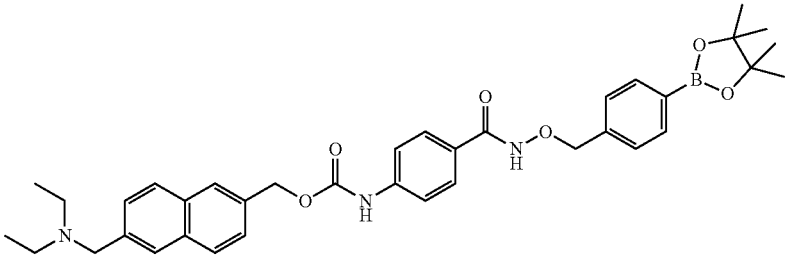 [SMILES: CCN(CC)Cc1ccc2cc(COC(=O)Nc3ccc(C(=O)NOCc4ccc(B5OC(C)(C)C(C)(C)O5)cc4)cc3)ccc2c1] |
| Compound 5 | C₂₉H₃₆BN₃O₆S | 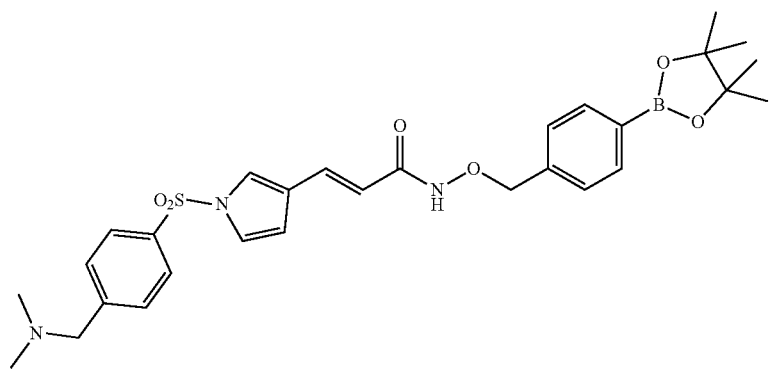 |

TABLE 6-continued
| Compound No. | Molecular formula | Structure |
| --- | --- | --- |
| Compound 6 | $C_{23}H_{26}BN_3O_6S$ | 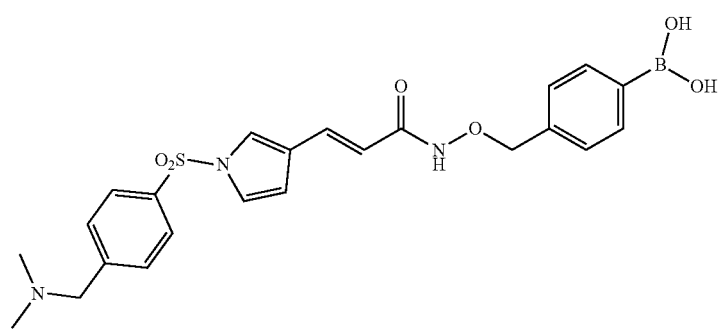 [SMILES: CN(C)Cc1ccc(S(=O)(=O)n2ccc(/C=C/C(=O)NOCc3ccc(B(O)O)cc3)c2)cc1] |
| Compound 7 | $C_{29}H_{39}BCl_2N_4O_4$ | 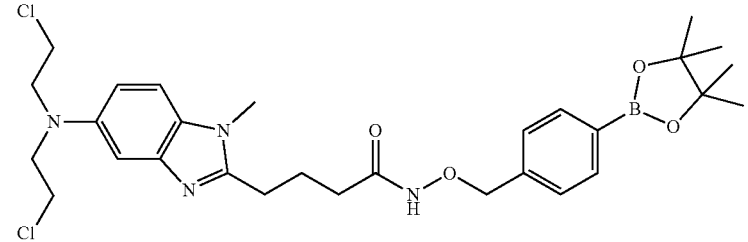 [SMILES: Cn1c(CCCC(=O)NOCc2ccc(B3OC(C)(C)C(C)(C)O3)cc2)nc2cc(N(CCCl)CCCl)ccc21] |
| Compound 8 | $C_{33}H_{46}BNO_4$ | 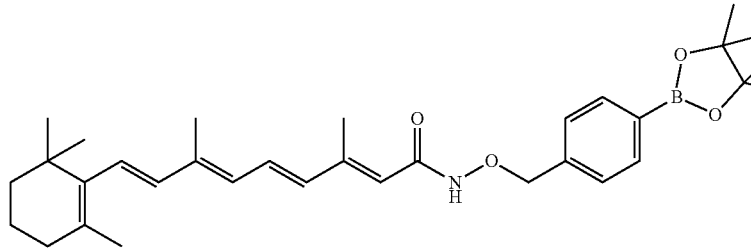 |
| Compound 9 | $C_{24}H_{30}BNO_6$ | 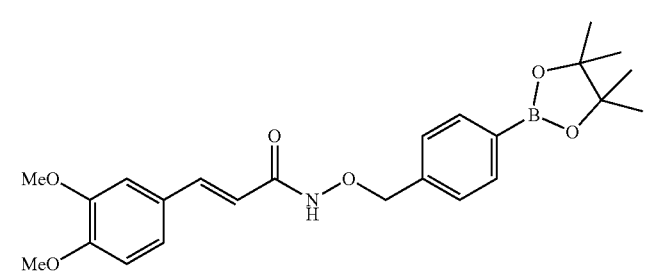 [SMILES: COc1ccc(/C=C/C(=O)NOCc2ccc(B3OC(C)(C)C(C)(C)O3)cc2)cc1OC] |
| Compound 10 | $C_{21}H_{26}BNO_5$ | 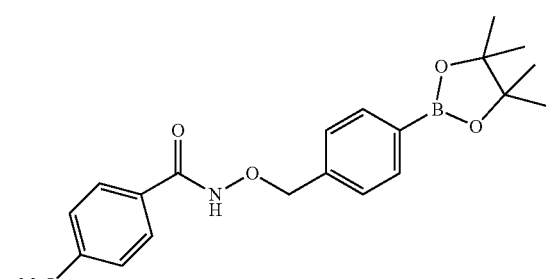 |

TABLE 6-continued

| Compound No. | Molecular formula | Structure |
| --- | --- | --- |
| Compound 11 | $C_{33}H_{35}BFNO_5S$ | 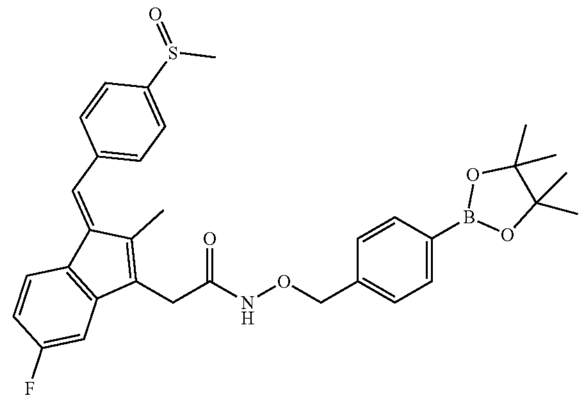 [SMILES: CC1=C(CC(=O)NOCc2ccc(B3OC(C)(C)C(C)(C)O3)cc2)c2cc(F)ccc2/C1=C/c1ccc(S(C)=O)cc1] |
| Compound 12 | $C_{33}H_{47}BN_4O_4$ | 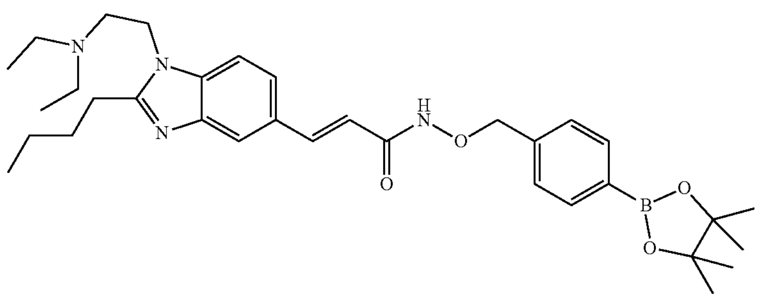 [SMILES: CCCCc1nc2cc(/C=C/C(=O)NOCc3ccc(B4OC(C)(C)C(C)(C)O4)cc3)ccc2n1CCN(CC)CC] |
| Compound 13 | $C_{23}H_{30}BNO_7$ | 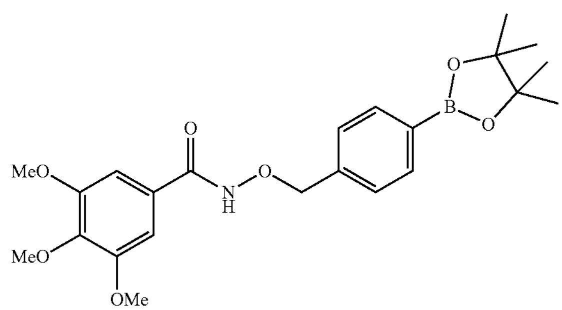 [SMILES: COc1cc(C(=O)NOCc2ccc(B3OC(C)(C)C(C)(C)O3)cc2)cc(OC)c1OC] |
| Compound 14 | $C_{26}H_{36}BNO_4$ | 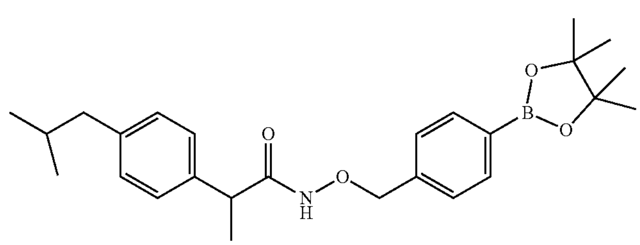 [SMILES: CC(C)Cc1ccc(C(C)C(=O)NOCc2ccc(B3OC(C)(C)C(C)(C)O3)cc2)cc1] |
| Compound 15 | $C_{23}H_{24}BNO_6$ | 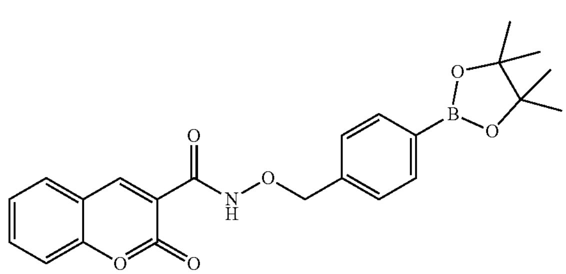 |

TABLE 6-continued

| Compound No. | Molecular formula | Structure |
| --- | --- | --- |
| Compound 16 | $C_{22}H_{28}BNO_6$ | 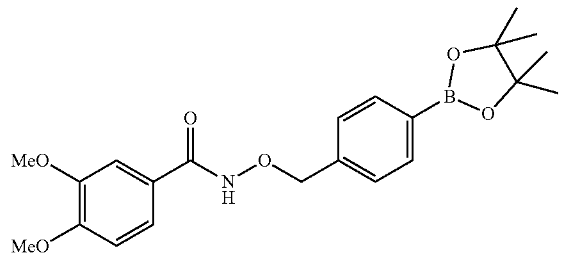 [SMILES: COc1ccc(C(=O)NOCc2ccc(B3OC(C)(C)C(C)(C)O3)cc2)cc1OC] |
| Compound 17 | $C_{34}H_{40}BN_3O_7$ | 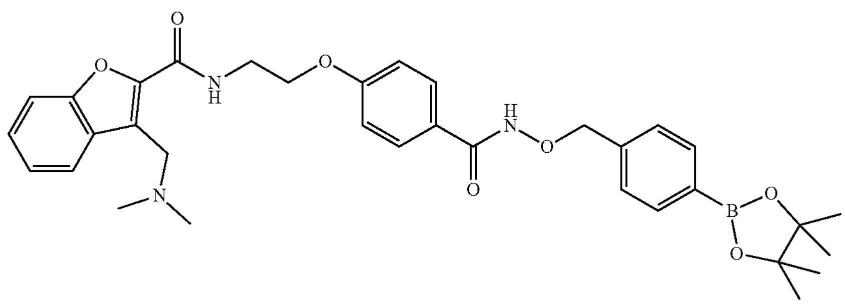 [SMILES: CN(C)Cc1c(C(=O)NCCOc2ccc(C(=O)NOCc3ccc(B4OC(C)(C)C(C)(C)O4)cc3)cc2)oc2ccccc12] |
| Compound 18 | $C_{28}H_{30}BN_3O_7$ | 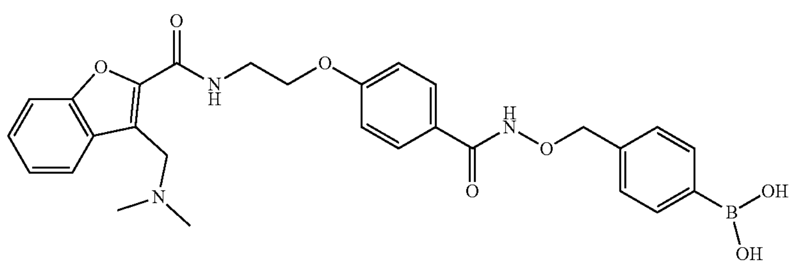 [SMILES: CN(C)Cc1c(C(=O)NCCOc2ccc(C(=O)NOCc3ccc(B(O)O)cc3)cc2)oc2ccccc12] |
| Compound 19 | $C_{31}H_{34}BN_3O_6$ | 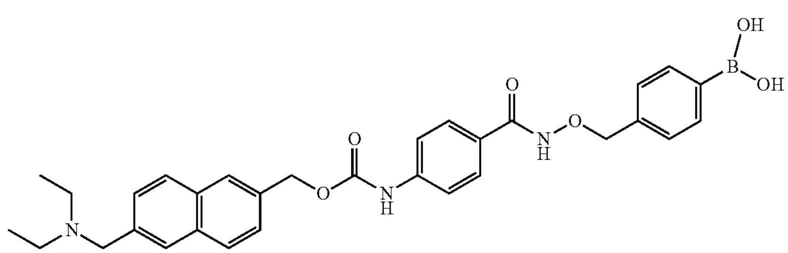 [SMILES: CCN(CC)Cc1ccc2cc(COC(=O)Nc3ccc(C(=O)NOCc4ccc(B(O)O)cc4)cc3)ccc2c1] |
| Compound 20 | $C_{27}H_{37}BN_4O_4$ | 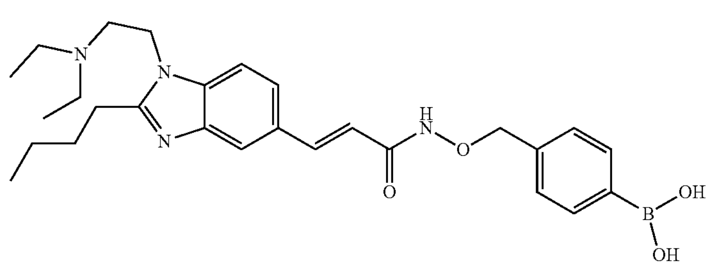 [SMILES: CCCCc1nc2cc(/C=C/C(=O)NOCc3ccc(B(O)O)cc3)ccc2n1CCN(CC)CC] |

TABLE 6-continued

| Compound No. | Molecular formula | Structure |
| --- | --- | --- |
| Compound 21 | $C_{34}H_{40}BN_3O_4$ | 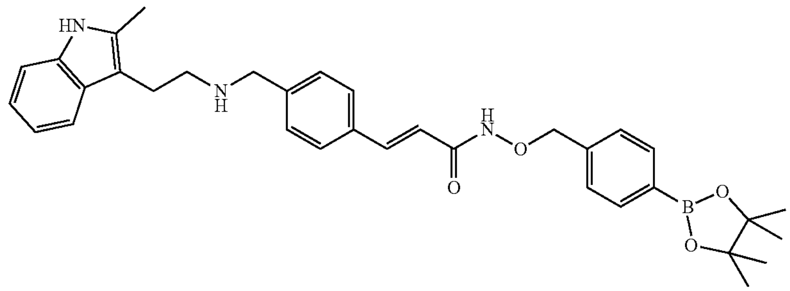 [SMILES: Cc1[nH]c2ccccc2c1CCNCc1ccc(/C=C/C(=O)NOCc2ccc(B3OC(C)(C)C(C)(C)O3)cc2)cc1] |
| Compound 22 | $C_{28}H_{30}BN_3O_4$ | 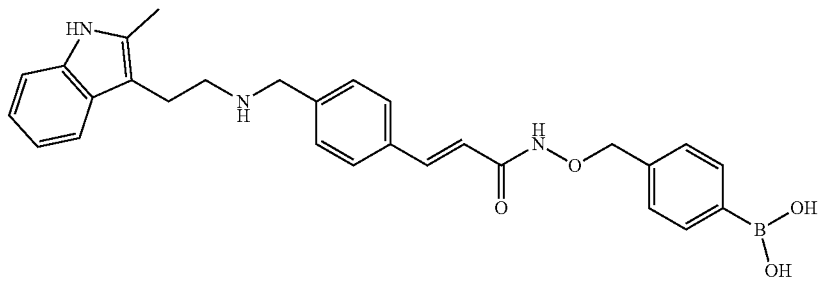 [SMILES: Cc1[nH]c2ccccc2c1CCNCc1ccc(/C=C/C(=O)NOCc2ccc(B(O)O)cc2)cc1] |
| Compound 23 | $C_{34}H_{43}BN_6O_4$ | 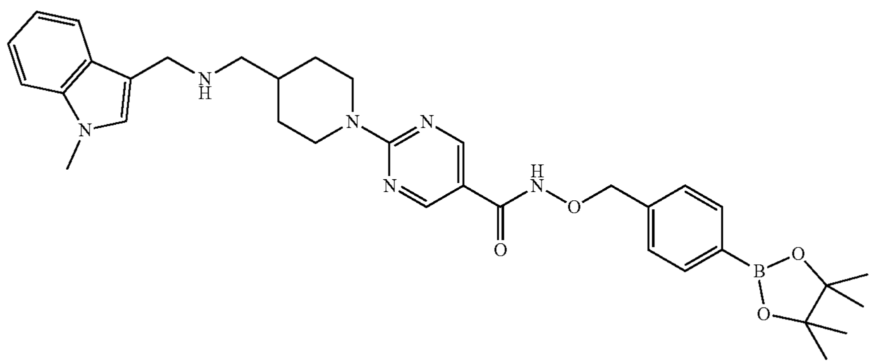 [SMILES: Cn1cc(CNCC2CCN(c3ncc(C(=O)NOCc4ccc(B5OC(C)(C)C(C)(C)O5)cc4)cn3)CC2)c2ccccc21] |
| Compound 24 | $C_{28}H_{33}BN_6O_4$ | 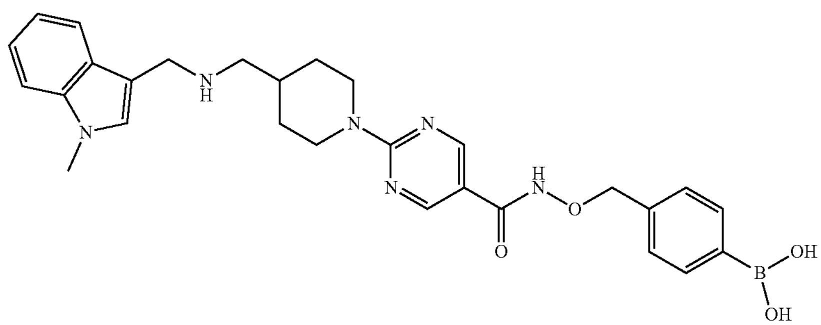 [SMILES: Cn1cc(CNCC2CCN(c3ncc(C(=O)NOCc4ccc(B(O)O)cc4)cn3)CC2)c2ccccc21] |
| Compound 25 | $C_{37}H_{43}BN_4O_6$ | 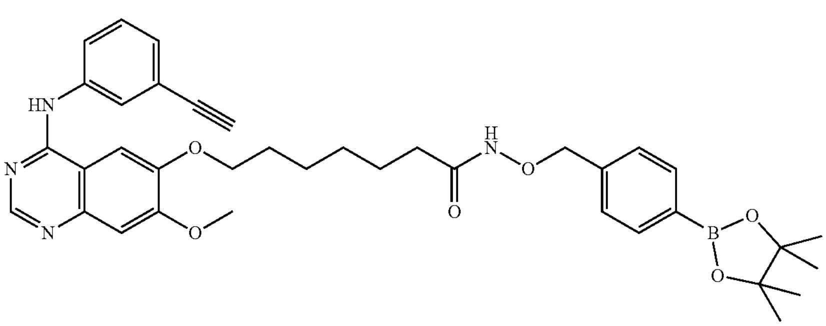 [SMILES: C#Cc1cccc(Nc2ncnc3cc(OC)c(OCCCCCCC(=O)NOCc4ccc(B5OC(C)(C)C(C)(C)O5)cc4)cc23)c1] |

TABLE 6-continued

| Compound No. | Molecular formula | Structure |
| --- | --- | --- |
| Compound 26 | $C_{31}H_{33}BN_4O_6$ | 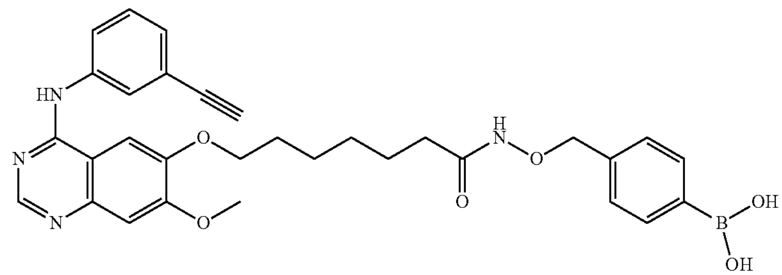 [SMILES: C#Cc1cccc(Nc2ncnc3cc(OC)c(OCCCCCCC(=O)NOCc4ccc(B(O)O)cc4)cc23)c1] |
| Compound 27 | $C_{32}H_{45}BCl_2N_4O_4$ | 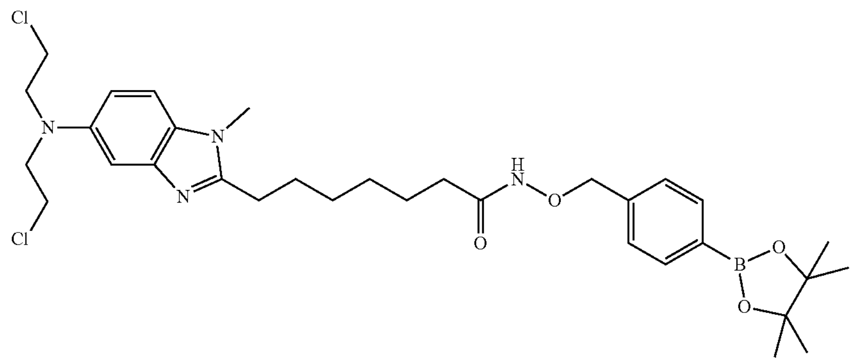 [SMILES: Cn1c(CCCCCCC(=O)NOCc2ccc(B3OC(C)(C)C(C)(C)O3)cc2)nc2cc(N(CCCl)CCCl)ccc21] |
| Compound 28 | $C_{26}H_{35}BCl_2N_4O_4$ | 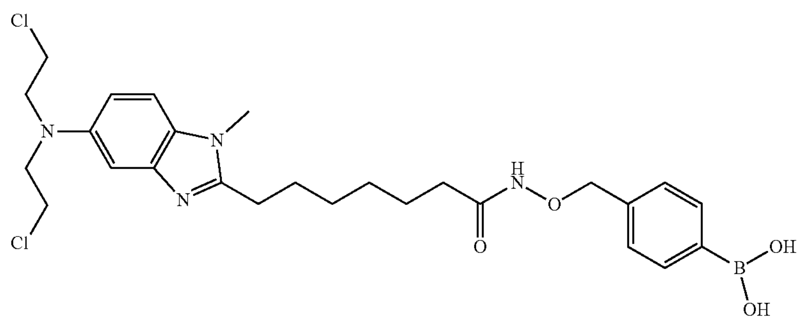 [SMILES: Cn1c(CCCCCCC(=O)NOCc2ccc(B(O)O)cc2)nc2cc(N(CCCl)CCCl)ccc21] |
| Compound 29 | $C_{27}H_{37}BCl_2N_2O_4$ | 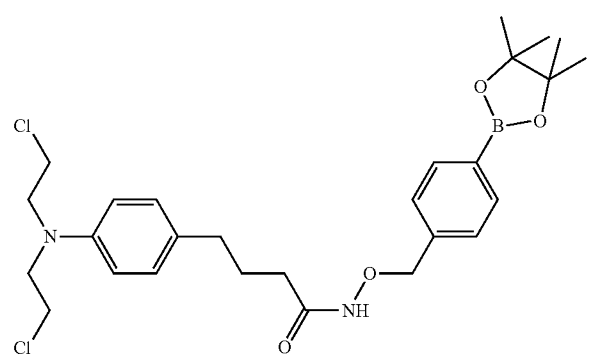 [SMILES: CC1(C)OB(c2ccc(CONC(=O)CCCc3ccc(N(CCCl)CCCl)cc3)cc2)OC1(C)C] |
| Compound 30 | $C_{21}H_{27}BCl_2N_2O_4$ | 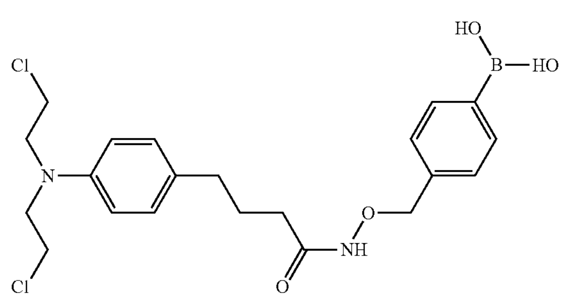 [SMILES: O=C(CCCc1ccc(N(CCCl)CCCl)cc1)NOCc1ccc(B(O)O)cc1] |

TABLE 6-continued
| Compound No. | Molecular formula | Structure |
|---|---|---|
| Compound 31 | $C_{30}H_{43}BCl_2N_2O_4$ | 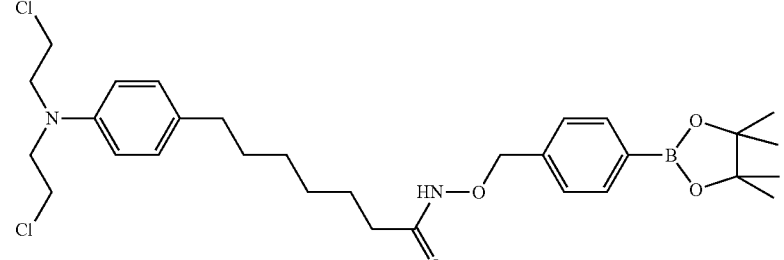 |
| Compound 32 | $C_{24}H_{33}BCl_2N_2O_4$ | 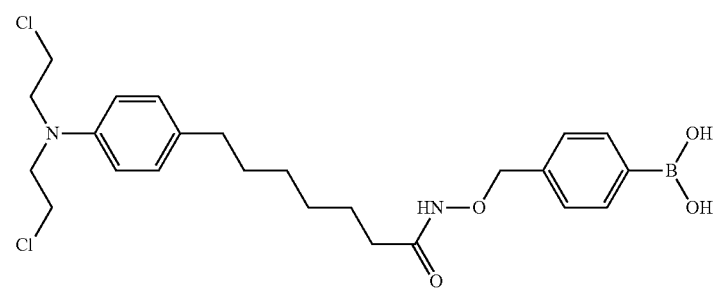 [SMILES: O=C(CCCCCCc1ccc(N(CCCl)CCCl)cc1)NOCc1ccc(B(O)O)cc1] |
| Compound 33 | $C_{30}H_{38}BNO_8$ | 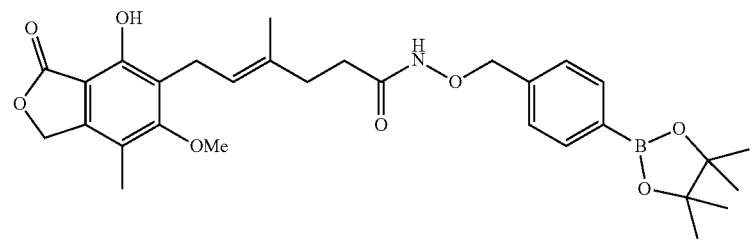 [SMILES: COc1c(C)c2c(c(O)c1C/C=C(\C)CCC(=O)NOCc1ccc(B3OC(C)(C)C(C)(C)O3)cc1)C(=O)OC2] |
| Compound 34 | $C_{24}H_{28}BNO_8$ | 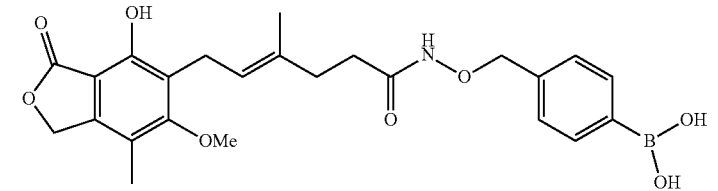 [SMILES: COc1c(C)c2c(c(O)c1C/C=C(\C)CCC(=O)NOCc1ccc(B(O)O)cc1)C(=O)OC2] |
| Compound 35 | $C_{23}H_{25}BF_3NO_4$ | 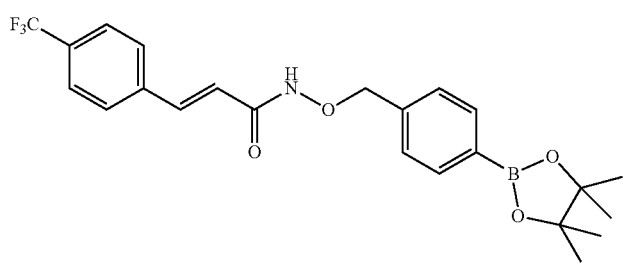 [SMILES: CC1(C)OB(c2ccc(CONC(=O)/C=C/c3ccc(C(F)(F)F)cc3)cc2)OC1(C)C] |
| Compound 36 | $C_{17}H_{15}BF_3NO_4$ | 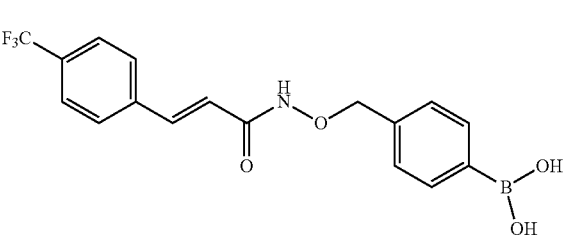 [SMILES: O=C(/C=C/c1ccc(C(F)(F)F)cc1)NOCc1ccc(B(O)O)cc1] |

TABLE 6-continued

| Compound No. | Molecular formula | Structure |
| --- | --- | --- |
| Compound 37 | $C_{28}H_{28}BNO_6S_2$ | 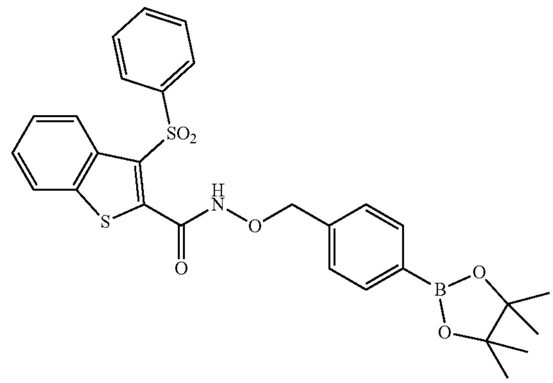 [SMILES: CC1(C)OB(c2ccc(CONC(=O)c3sc4ccccc4c3S(=O)(=O)c3ccccc3)cc2)OC1(C)C] |
| Compound 38 | $C_{22}H_{18}BNO_6S_2$ | 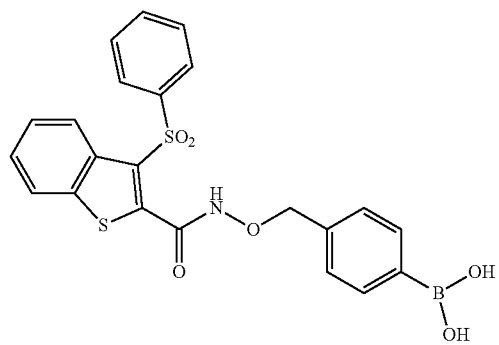 [SMILES: O=C(NOCc1ccc(B(O)O)cc1)c1sc2ccccc2c1S(=O)(=O)c1ccccc1] |
| Compound 39 | $C_{28}H_{30}BBrN_2O_5$ | 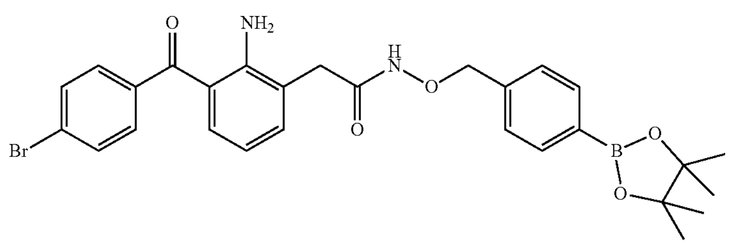 [SMILES: CC1(C)OB(c2ccc(CONC(=O)Cc3cccc(C(=O)c4ccc(Br)cc4)c3N)cc2)OC1(C)C] |
| Compound 40 | $C_{22}H_{20}BBrN_2O_5$ | 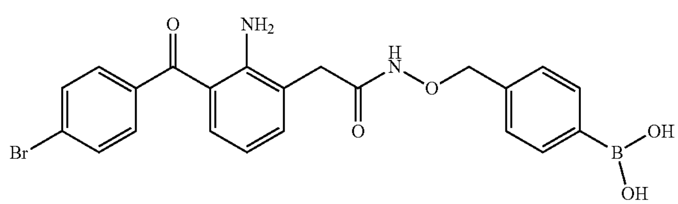 [SMILES: Nc1c(CC(=O)NOCc2ccc(B(O)O)cc2)cccc1C(=O)c1ccc(Br)cc1] |
| Compound 41 | $C_{37}H_{46}BNO_4$ | 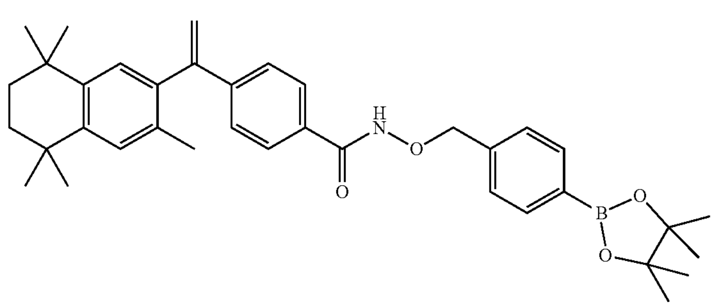 [SMILES: C=C(c1ccc(C(=O)NOCc2ccc(B3OC(C)(C)C(C)(C)O3)cc2)cc1)c1cc2c(cc1C)C(C)(C)CCC2(C)C] |

TABLE 6-continued
| Compound No. | Molecular formula | Structure |
|---|---|---|
| Compound 42 | C$_{31}$H$_{36}$BNO$_4$ | 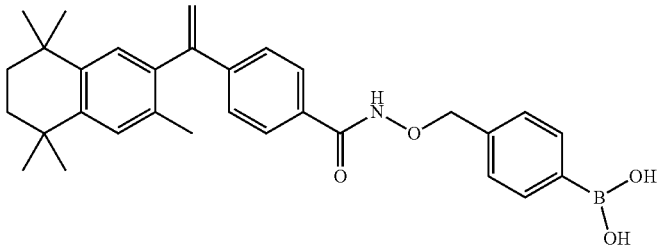 [SMILES: C=C(c1ccc(C(=O)NOCc2ccc(B(O)O)cc2)cc1)c1cc2c(cc1C)C(C)(C)CCC2(C)C] |
| Compound 43 | C$_{33}$H$_{46}$BNO$_4$ | 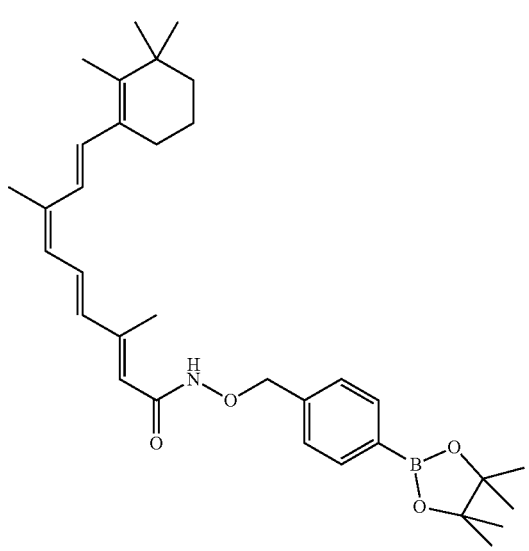 [SMILES: CC1=C(/C=C/C(C)=C\C=C\C(C)=C\C(=O)NOCc2ccc(B3OC(C)(C)C(C)(C)O3)cc2)CCCC1(C)C] |
| Compound 44 | C$_{27}$H$_{36}$BNO$_4$ | 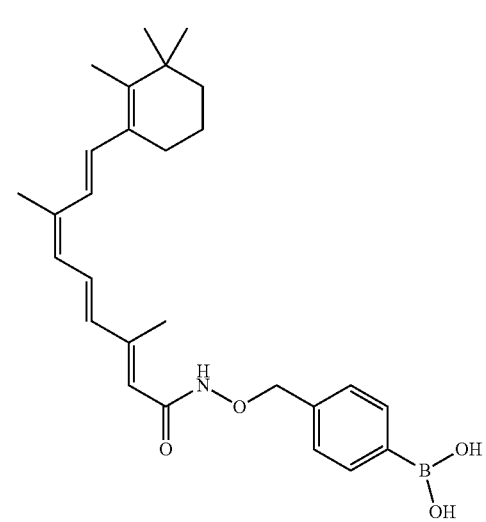 [SMILES: CC1=C(/C=C/C(C)=C\C=C\C(C)=C\C(=O)NOCc2ccc(B(O)O)cc2)CCCC1(C)C] |
| Compound 45 | C$_{21}$H$_{34}$BNO$_4$ | 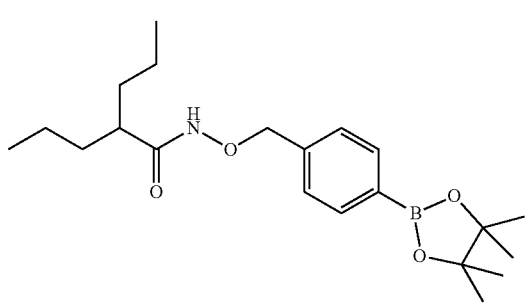 [SMILES: CCCC(CCC)C(=O)NOCc1ccc(B2OC(C)(C)C(C)(C)O2)cc1] |

TABLE 6-continued

| Compound No. | Molecular formula | Structure |
| --- | --- | --- |
| Compound 46 | C₁₅H₂₄BNO₄ | 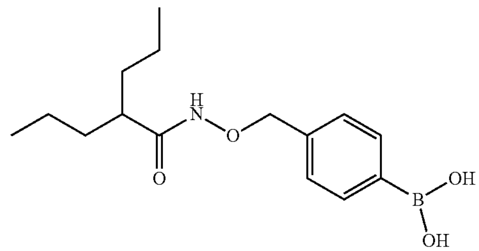 [SMILES: CCCC(CCC)C(=O)NOCc1ccc(B(O)O)cc1] |
| Compound 47 | C₃₇H₄₇BN₆O₅ | 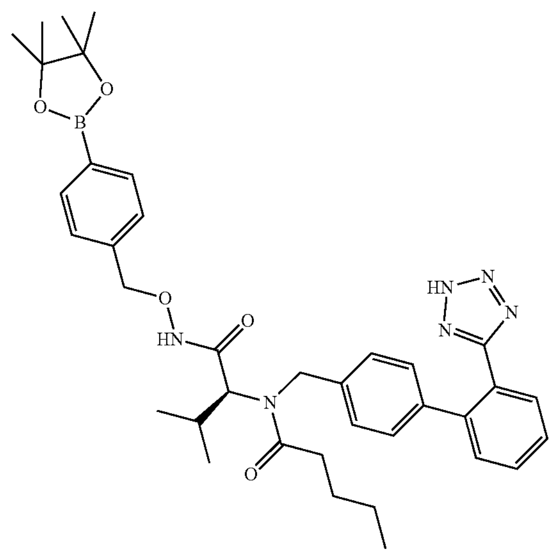 [SMILES: CCCCC(=O)N(Cc1ccc(-c2ccccc2-c2nn[nH]n2)cc1)[C@H](C(=O)NOCc1ccc(B2OC(C)(C)C(C)(C)O2)cc1)C(C)C] |
| Compound 48 | C₃₁H₃₇BN₆O₅ | 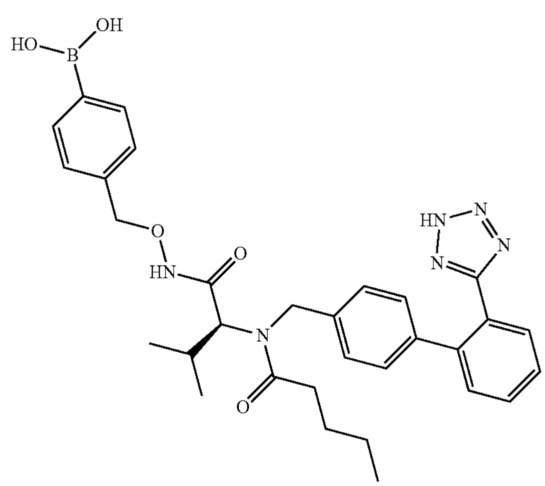 [SMILES: CCCCC(=O)N(Cc1ccc(-c2ccccc2-c2nn[nH]n2)cc1)[C@H](C(=O)NOCc1ccc(B(O)O)cc1)C(C)C] |

TABLE 6-continued

| Compound No. | Molecular formula | Structure |
| --- | --- | --- |
| Compound 49 | C$_{36}$H$_{41}$BN$_8$O$_6$S | 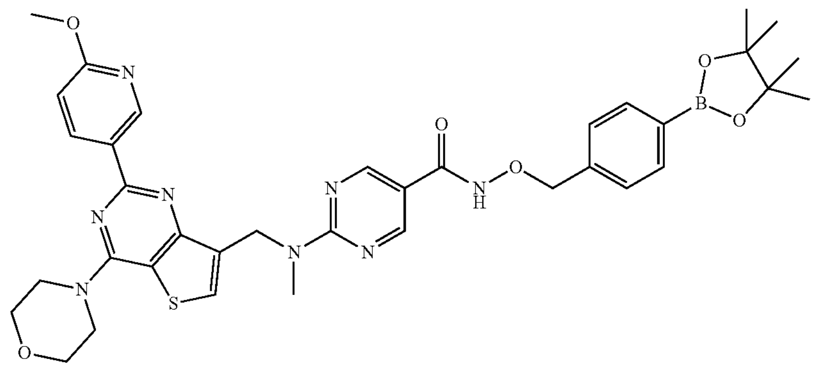 [SMILES: COc1ccc(-c2nc(N3CCOCC3)c3scc(CN(C)c4ncc(C(=O)NOCc5ccc(B6OC(C)(C)C(C)(C)O6)cc5)cn4)c3n2)cn1] |
| Compound 50 | C$_{30}$H$_{31}$BN$_8$O$_6$S | 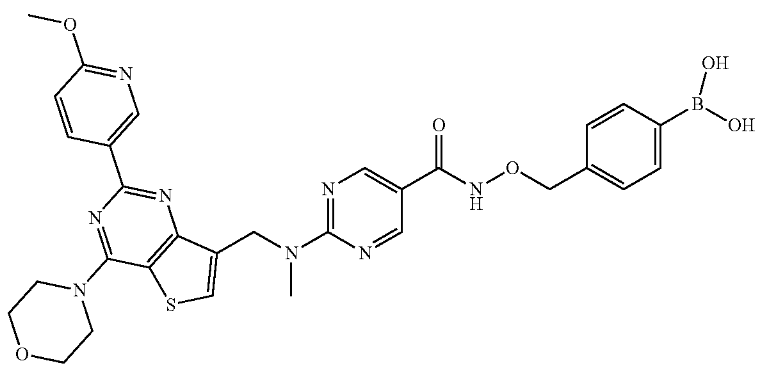 [SMILES: COc1ccc(-c2nc(N3CCOCC3)c3scc(CN(C)c4ncc(C(=O)NOCc5ccc(B(O)O)cc5)cn4)c3n2)cn1] |
| Compound 51 | C$_{35}$H$_{47}$BN$_4$O$_8$ | 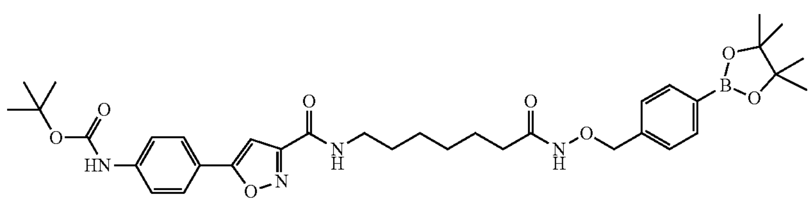 [SMILES: CC(C)(C)OC(=O)Nc1ccc(-c2cc(C(=O)NCCCCCCC(=O)NOCc3ccc(B4OC(C)(C)C(C)(C)O4)cc3)no2)cc1] |
| Compound 52 | C$_{29}$H$_{37}$BN$_4$O$_8$ | 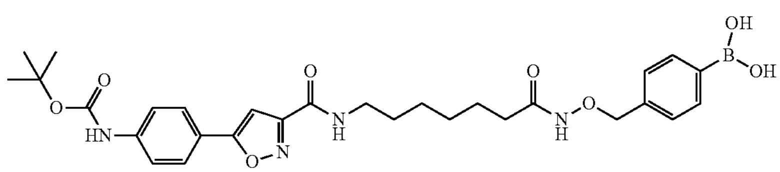 [SMILES: CC(C)(C)OC(=O)Nc1ccc(-c2cc(C(=O)NCCCCCCC(=O)NOCc3ccc(B(O)O)cc3)no2)cc1] |
| Compound 53 | C$_{30}$H$_{35}$BN$_2$O$_6$ | 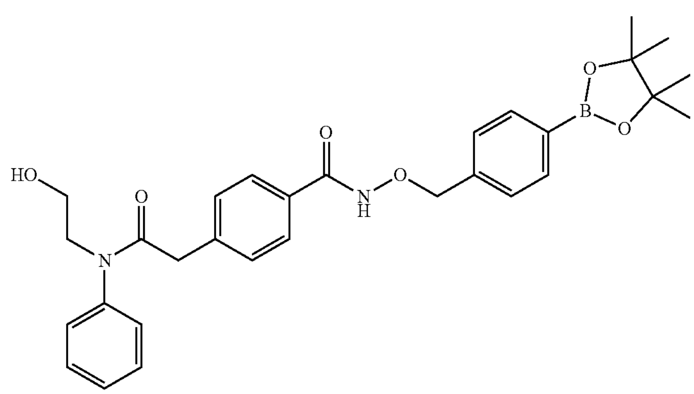 [SMILES: CC1(C)OB(c2ccc(CONC(=O)c3ccc(CC(=O)N(CCO)c4ccccc4)cc3)cc2)OC1(C)C] |

TABLE 6-continued

| Compound No. | Molecular formula | Structure |
|---|---|---|
| Compound 54 | C₂₄H₂₅BN₂O₆ | 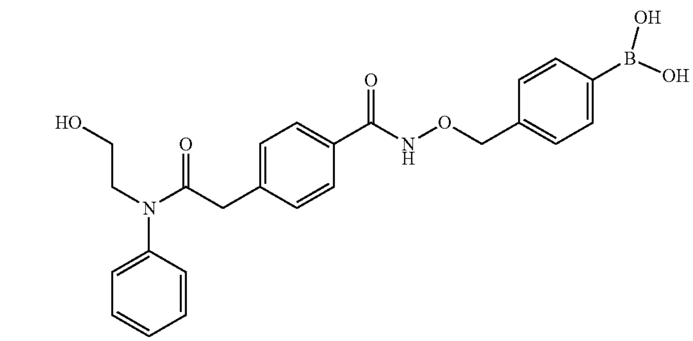 [SMILES: O=C(NOCc1ccc(B(O)O)cc1)c1ccc(CC(=O)N(CCO)c2ccccc2)cc1] |
| Compound 55 | C₃₀H₃₃BN₂O₅ | 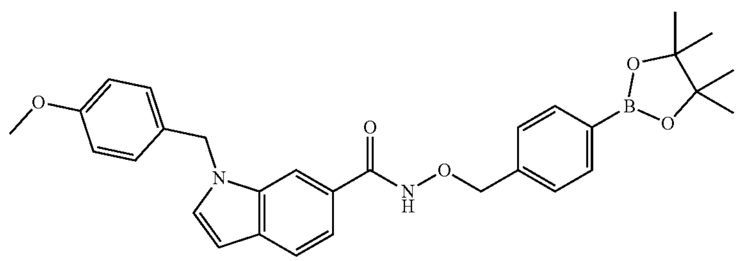 |
| Compound 56 | C₂₄H₂₃BN₂O₅ | 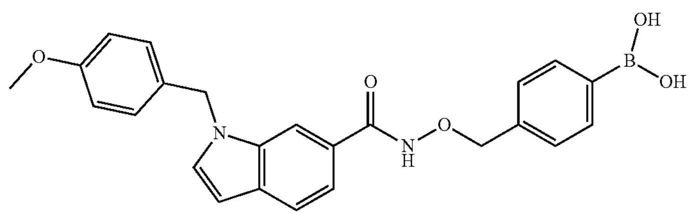 [SMILES: COc1ccc(Cn2ccc3ccc(C(=O)NOCc4ccc(B(O)O)cc4)cc32)cc1] |
| Compound 57 | C₃₃H₄₀BN₃O₄ | 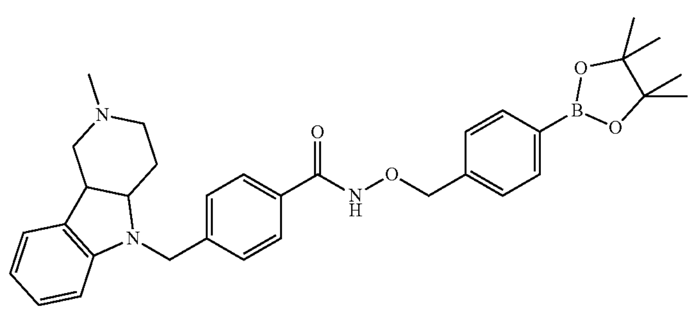 [SMILES: CN1CCC2C(C1)c1ccccc1N2Cc1ccc(C(=O)NOCc2ccc(B3OC(C)(C)C(C)(C)O3)cc2)cc1] |
| Compound 58 | C₂₇H₃₀BN₃O₄ | 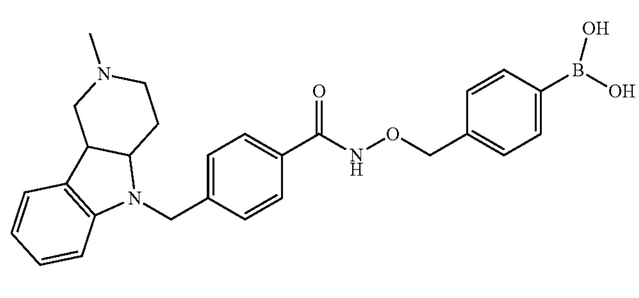 [SMILES: CN1CCC2C(C1)c1ccccc1N2Cc1ccc(C(=O)NOCc2ccc(B(O)O)cc2)cc1] |

TABLE 6-continued

| Compound No. | Molecular formula | Structure |
| --- | --- | --- |
| Compound 59 | C₃₇H₄₄BN₅O₅ | 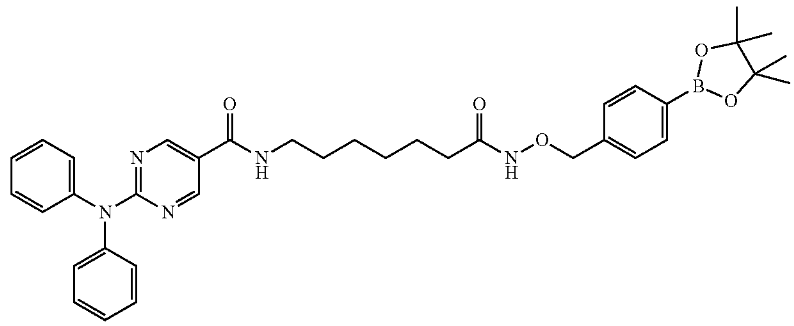 [SMILES: CC1(C)OB(c2ccc(CONC(=O)CCCCCCNC(=O)c3cnc(N(c4ccccc4)c4ccccc4)nc3)cc2)OC1(C)C] |
| Compound 60 | C₃₁H₃₄BN₅O₅ | 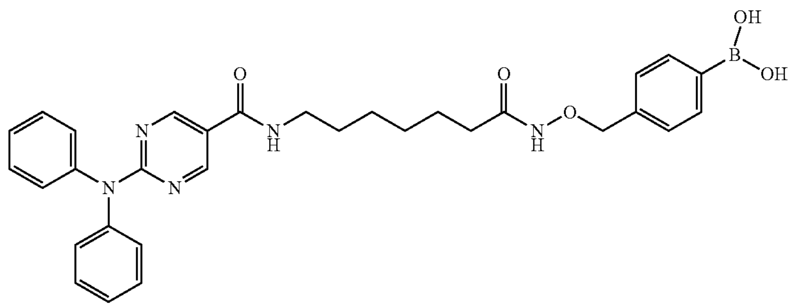 [SMILES: O=C(CCCCCCNC(=O)c1cnc(N(c2ccccc2)c2ccccc2)nc1)NOCc1ccc(B(O)O)cc1] |
| Compound 61 | C₂₄H₃₁BClNO₅ | 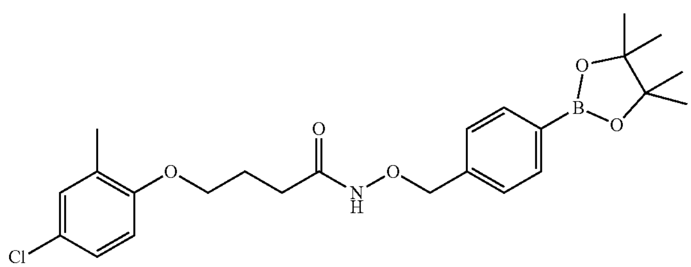 [SMILES: Cc1cc(Cl)ccc1OCCCC(=O)NOCc1ccc(B2OC(C)(C)C(C)(C)O2)cc1] |
| Compound 62 | C₁₈H₂₁BClNO₅ | 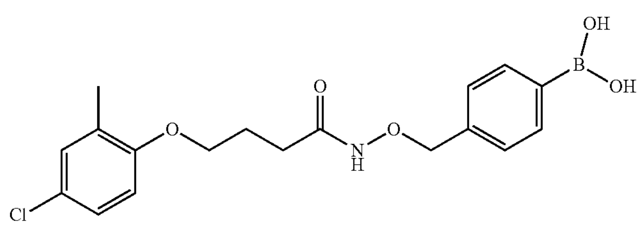 [SMILES: Cc1cc(Cl)ccc1OCCCC(=O)NOCc1ccc(B(O)O)cc1] |
| Compound 63 | C₂₈H₃₉BN₂O₆ | 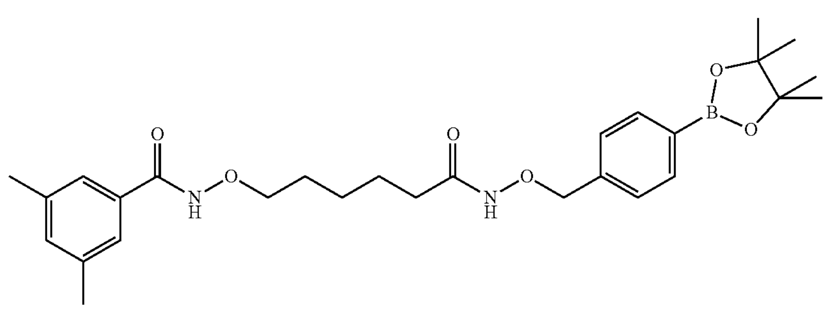 |

TABLE 6-continued

| Compound No. | Molecular formula | Structure |
| --- | --- | --- |
| Compound 64 | $C_{22}H_{29}BN_2O_6$ | 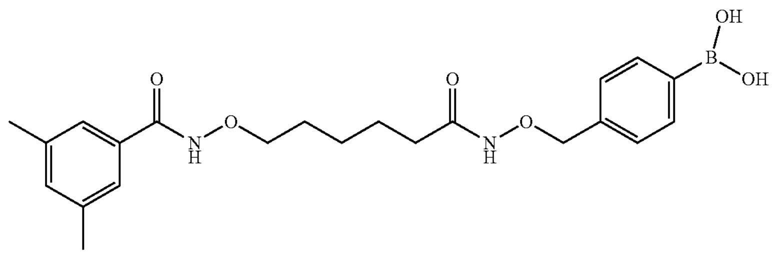 [SMILES: Cc1cc(C)cc(C(=O)NOCCCCCC(=O)NOCc2ccc(B(O)O)cc2)c1] |
| Compound 65 | $C_{54}H_{60}BN_3O_9S$ | 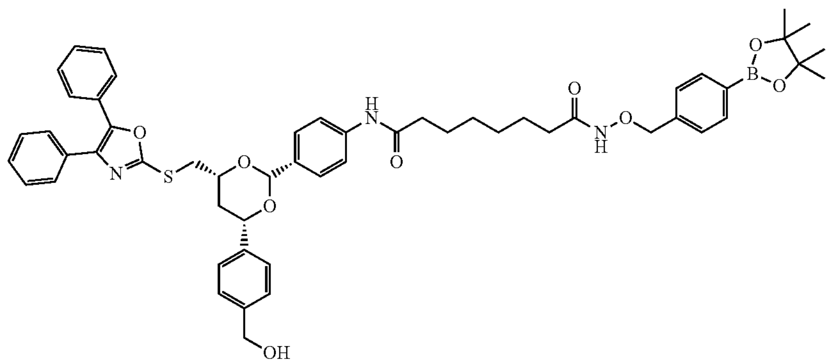 |
| Compound 66 | $C_{48}H_{50}BN_3O_9S$ | 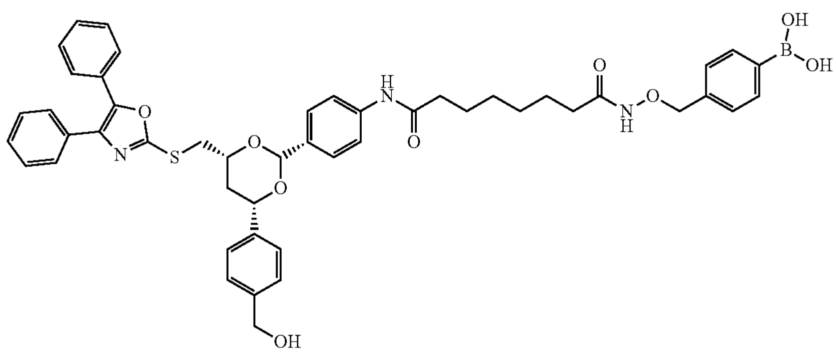 |
| Compound 67 | $C_{32}H_{40}BN_3O_5$ | 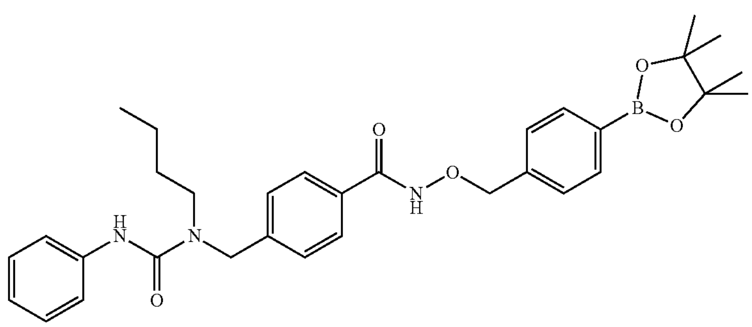 [SMILES: CCCCN(Cc1ccc(C(=O)NOCc2ccc(B3OC(C)(C)C(C)(C)O3)cc2)cc1)C(=O)Nc1ccccc1] |
| Compound 68 | $C_{26}H_{30}BN_3O_5$ | 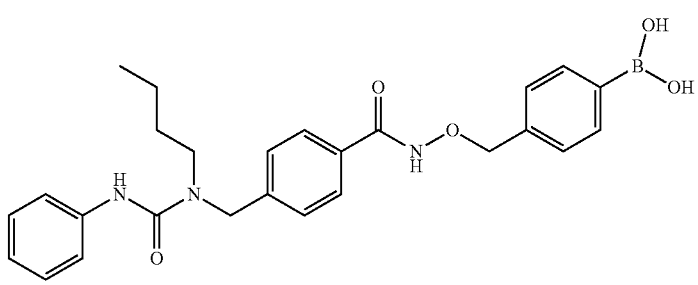 [SMILES: CCCCN(Cc1ccc(C(=O)NOCc2ccc(B(O)O)cc2)cc1)C(=O)Nc1ccccc1] |

TABLE 6-continued
| Compound No. | Molecular formula | Structure |
| --- | --- | --- |
| Compound 69 | C30H39BN2O5 | 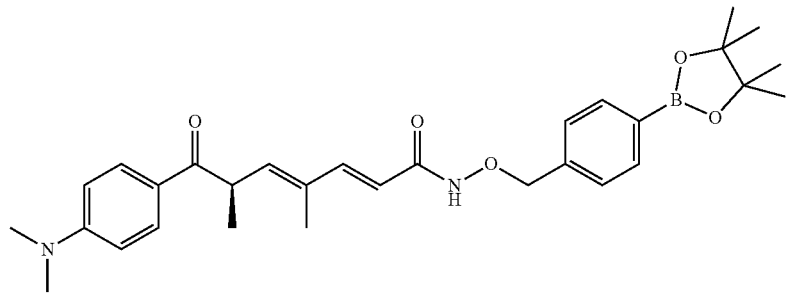 |
| Compound 70 | C24H29BN2O5 | 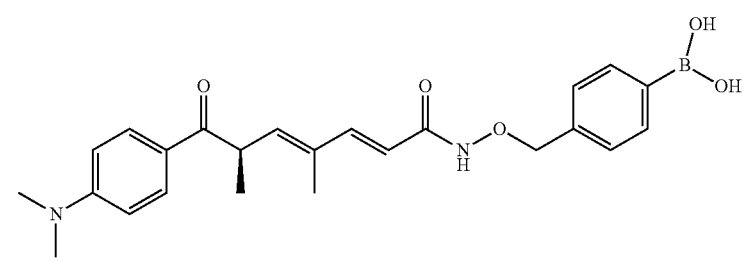 [SMILES: CC(/C=C/C(=O)NOCc1ccc(B(O)O)cc1)=C\[C@@H](C)C(=O)c1ccc(N(C)C)cc1] |
| Compound 71 | C30H32BFN2O5 | 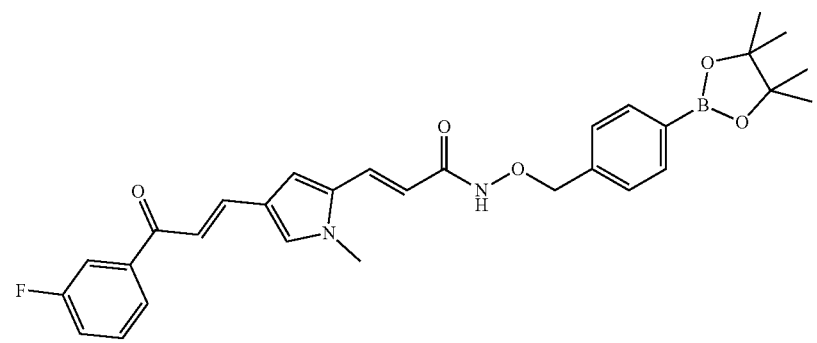 [SMILES: Cn1cc(/C=C/C(=O)c2cccc(F)c2)cc1/C=C/C(=O)NOCc1ccc(B2OC(C)(C)C(C)(C)O2)cc1] |
| Compound 72 | C24H22BFN2O5 | 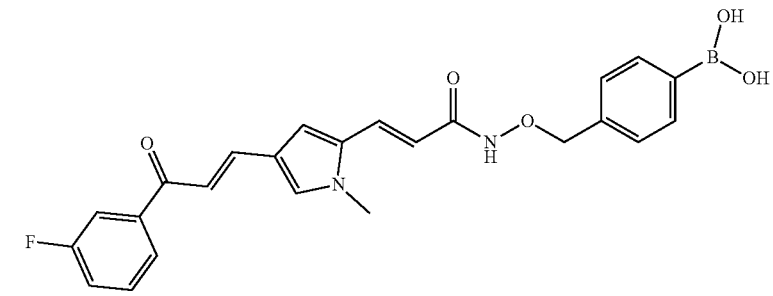 [SMILES: Cn1cc(/C=C/C(=O)c2cccc(F)c2)cc1/C=C/C(=O)NOCc1ccc(B(O)O)cc1] |
| Compound 73 | C35H42BN3O5 | 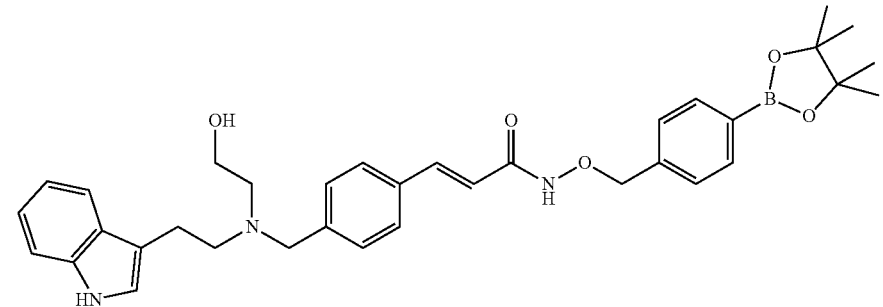 [SMILES: CC1(C)OB(c2ccc(CONC(=O)/C=C/c3ccc(CN(CCO)CCc4c[nH]c5ccccc45)cc3)cc2)OC1(C)C] |

TABLE 6-continued

| Compound No. | Molecular formula | Structure |
| --- | --- | --- |
| Compound 74 | $C_{29}H_{32}BN_3O_5$ | 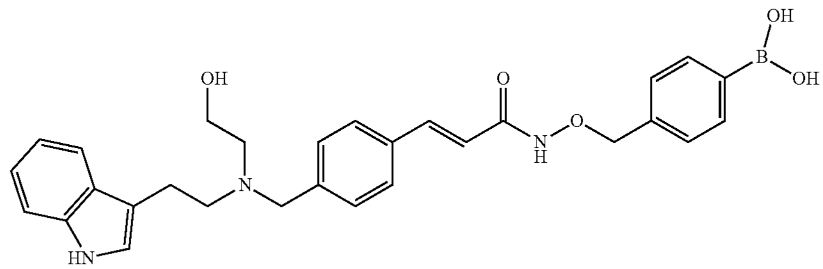 [SMILES: O=C(/C=C/c1ccc(CN(CCO)CCc2c[nH]c3ccccc23)cc1)NOCc1ccc(B(O)O)cc1] |
| Compound 75 | $C_{31}H_{37}BN_2O_5$ | 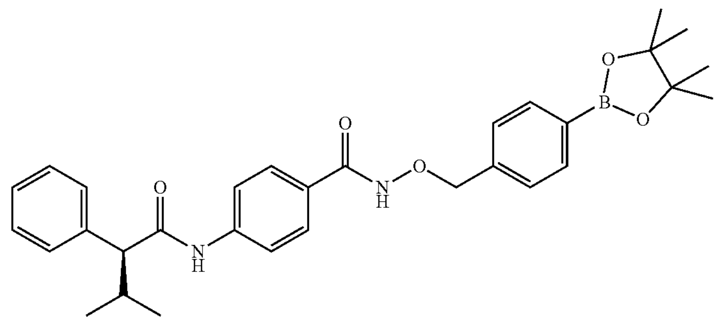 [SMILES: CC(C)[C@H](C(=O)Nc1ccc(C(=O)NOCc2ccc(B3OC(C)(C)C(C)(C)O3)cc2)cc1)c1ccccc1] |
| Compound 76 | $C_{25}H_{27}BN_2O_5$ | 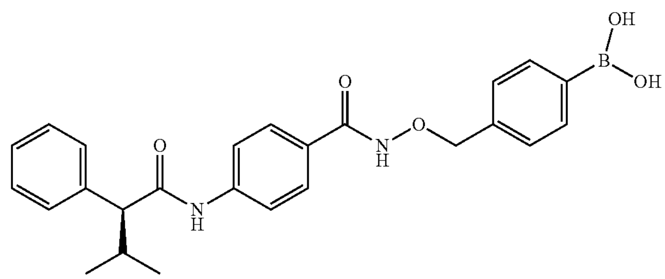 [SMILES: CC(C)[C@H](C(=O)Nc1ccc(C(=O)NOCc2ccc(B(O)O)cc2)cc1)c1ccccc1] |
| Compound 77 | $C_{29}H_{42}BN_3O_5$ | 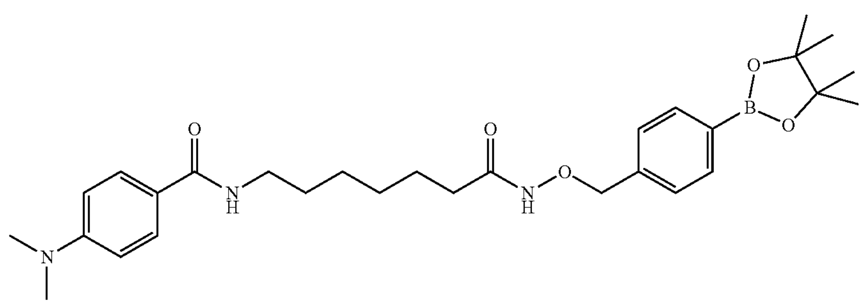 |
| Compound 78 | $C_{23}H_{32}BN_3O_5$ | 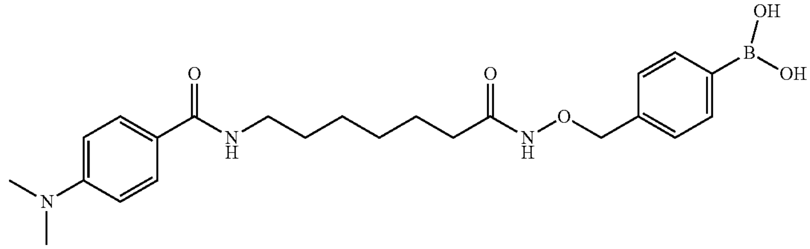 [SMILES: CN(C)c1ccc(C(=O)NCCCCCCC(=O)NOCc2ccc(B(O)O)cc2)cc1] |

TABLE 6-continued

| Compound No. | Molecular formula | Structure |
| --- | --- | --- |
| Compound 79 | C₃₁H₃₅BN₂O₆ | 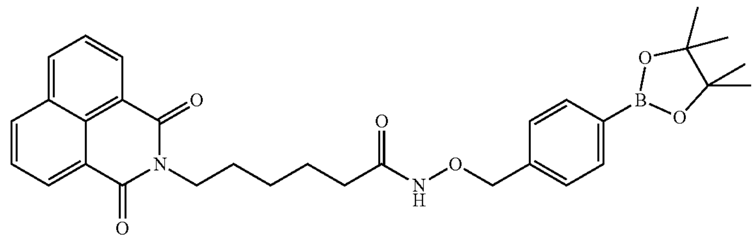 [SMILES: CC1(C)OB(c2ccc(CONC(=O)CCCCCN3C(=O)c4cccc5cccc(c45)C3=O)cc2)OC1(C)C] |
| Compound 80 | C₂₅H₂₅BN₂O₆ | 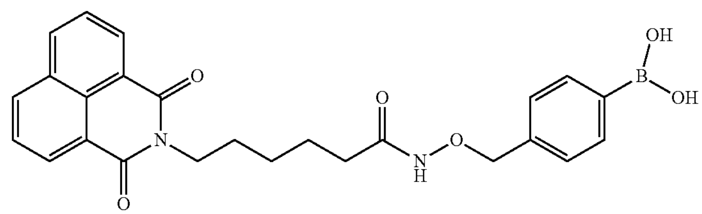 [SMILES: O=C(CCCCCN1C(=O)c2cccc3cccc(c23)C1=O)NOCc1ccc(B(O)O)cc1] |
| Compound 81 | C₃₃H₄₂BF₃N₄O₇ | 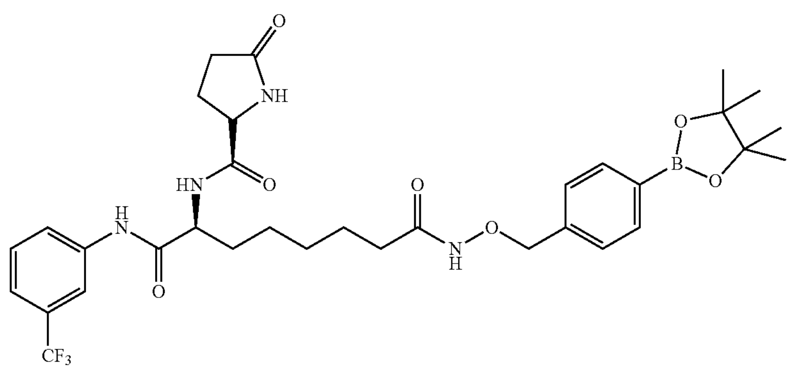 |
| Compound 82 | C₂₇H₃₂BF₃N₄O₇ | 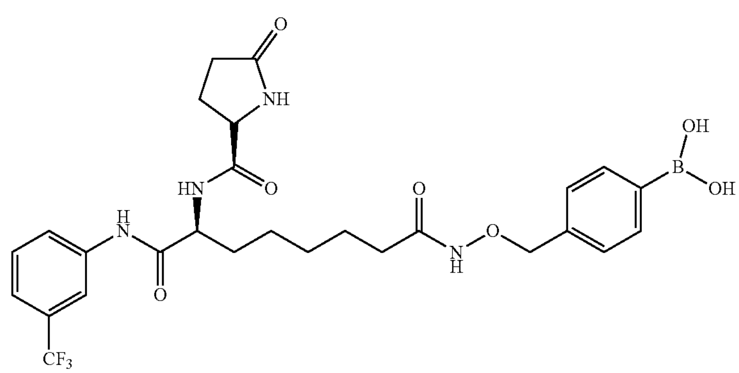 |
| Compound 83 | C₃₇H₄₅BN₆O₆ | 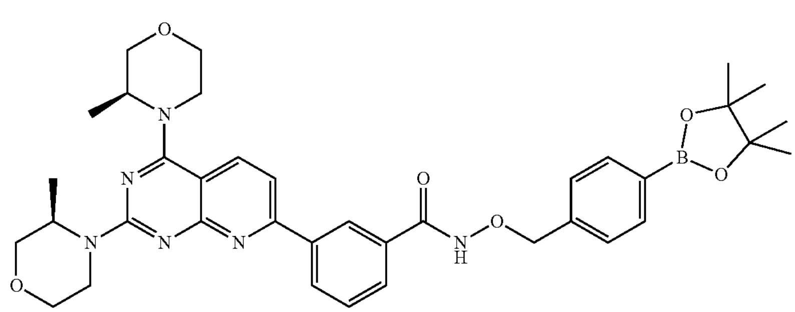 [SMILES: C[C@@H]1COCCN1c1nc(N2CCOC[C@@H]2C)c2ccc(-c3cccc(C(=O)NOCc4ccc(B5OC(C)(C)C(C)(C)O5)cc4)c3)nc2n1] |

TABLE 6-continued

| Compound No. | Molecular formula | Structure |
|---|---|---|
| Compound 84 | C$_{31}$H$_{35}$BN$_6$O$_6$ | 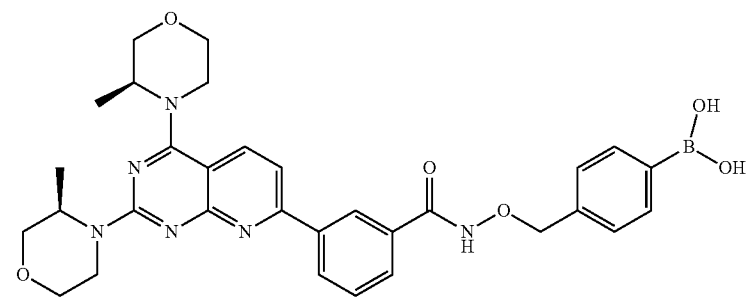 [SMILES: C[C@@H]1COCCN1c1nc(N2CCOC[C@@H]2C)c2ccc(-c3cccc(C(=O)NOCc4ccc(B(O)O)cc4)c3)nc2n1] |
| Compound 85 | C$_{43}$H$_{46}$BF$_5$N$_2$O$_8$S | 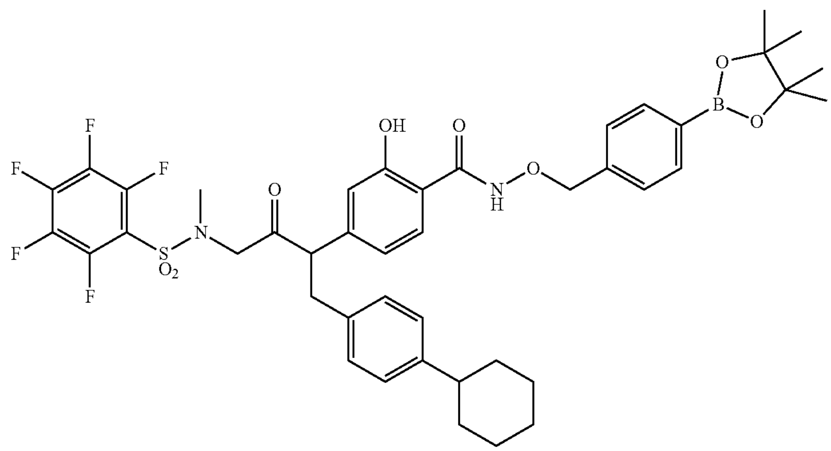 [SMILES: CN(CC(=O)C(Cc1ccc(C2CCCCC2)cc1)c1ccc(C(=O)NOCc2ccc(B3OC(C)(C)C(C)(C)O3)cc2)c(O)c1)S(=O)(=O)c1c(F)c(F)c(F)c(F)c1F] |
| Compound 86 | C$_{37}$H$_{36}$BF$_5$N$_2$O$_8$S | 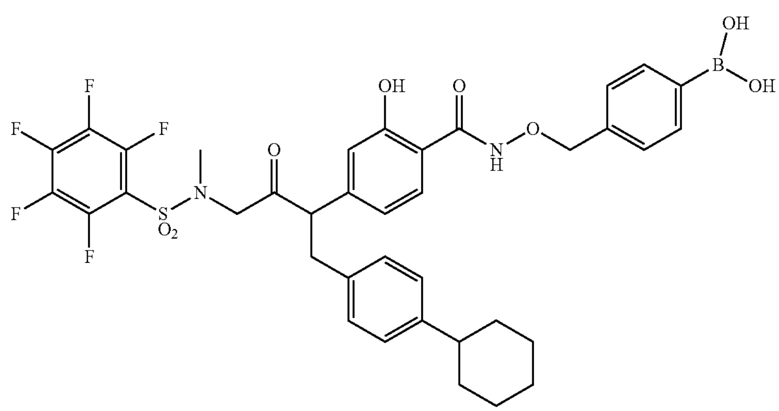 [SMILES: CN(CC(=O)C(Cc1ccc(C2CCCCC2)cc1)c1ccc(C(=O)NOCc2ccc(B(O)O)cc2)c(O)c1)S(=O)(=O)c1c(F)c(F)c(F)c(F)c1F] |
| Compound 87 | C$_{22}$H$_{26}$BNO$_6$ | 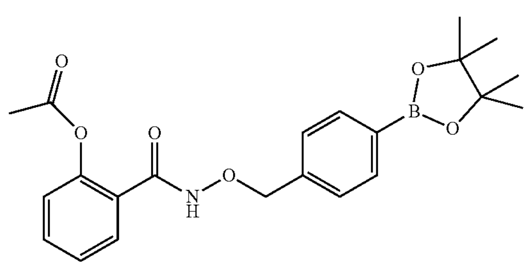 [SMILES: CC(=O)Oc1ccccc1C(=O)NOCc1ccc(B2OC(C)(C)C(C)(C)O2)cc1] |

TABLE 6-continued

| Compound No. | Molecular formula | Structure |
| --- | --- | --- |
| Compound 88 | C₁₆H₁₆BNO₆ | 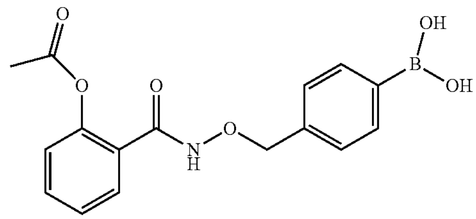 [SMILES: CC(=O)Oc1ccccc1C(=O)NOCc1ccc(B(O)O)cc1] |
| Compound 89 | C₂₆H₂₆BF₅NO₅ | 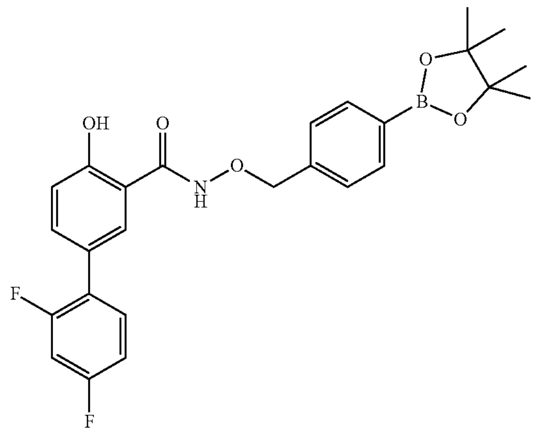 [SMILES: CC1(C)OB(c2ccc(CONC(=O)c3cc(-c4ccc(F)cc4F)ccc3O)cc2)OC1(C)C] |
| Compound 90 | C₂₀H₁₆BF₂NO₅ | 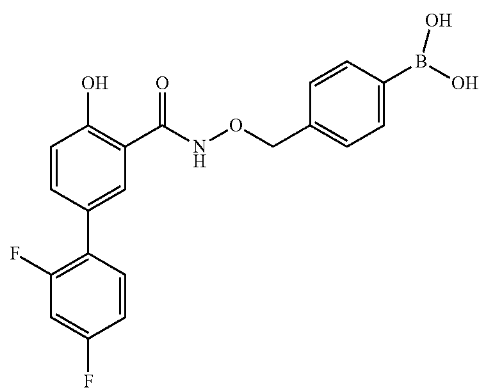 [SMILES: O=C(NOCc1ccc(B(O)O)cc1)c1cc(-c2ccc(F)cc2F)ccc1O] |
| Compound 91 | C₂₃H₂₉BCl₂N₄O₄ | 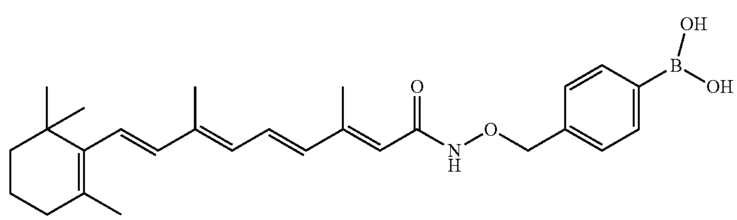 [SMILES: CC1=C(/C=C/C(C)=C/C=C/C(C)=C/C(=O)NOCc2ccc(B(O)O)cc2)C(C)(C)CCC1] |
| Compound 92 | C₂₀H₂₆BNO₄ | 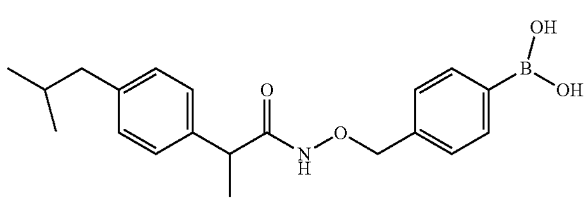 [SMILES: CC(C)Cc1ccc(C(C)C(=O)NOCc2ccc(B(O)O)cc2)cc1] |

TABLE 6-continued
| Compound No. | Molecular formula | Structure |
| --- | --- | --- |
| Compound 93 | $C_{21}H_{22}BNO_5S_2$ | 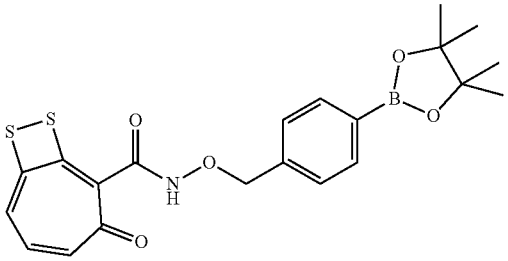 [SMILES: CC1(C)OB(c2ccc(CONC(=O)c3c(=O)cccc4ssc34)cc2)OC1(C)C] |
| Compound 94 | $C_{15}H_{12}BNO_5S_2$ | 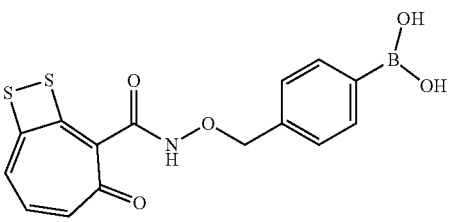 [SMILES: O=C(NOCc1ccc(B(O)O)cc1)c1c(=O)cccc2ssc12] |
| Compound 95 | $C_{22}H_{21}BN_2O_6S$ | 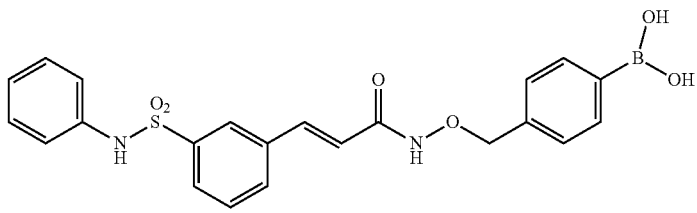 [SMILES: O=C(/C=C/c1cccc(S(=O)(=O)Nc2ccccc2)c1)NOCc1ccc(B(O)O)cc1] |
| Compound 96 | $C_{27}H_{25}BFNO_5S$ | 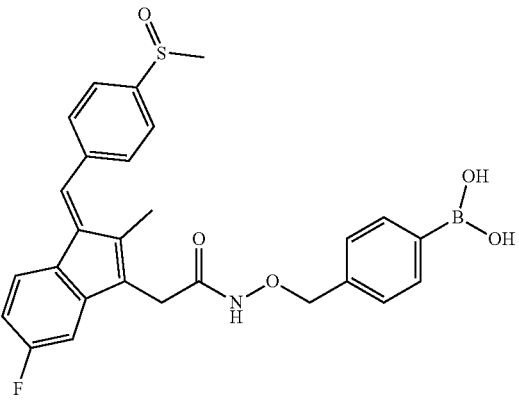 [SMILES: CC1=C(CC(=O)NOCc2ccc(B(O)O)cc2)c2cc(F)ccc2/C1=C/c1ccc(S(C)=O)cc1] |
| Compound 97 | $C_{33}H_{30}BClF_4N_4O_6$ | 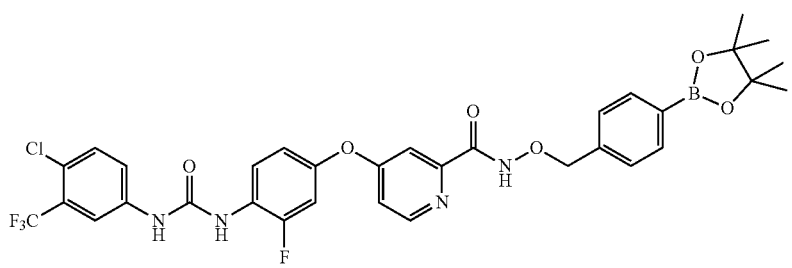 [SMILES: CC1(C)OB(c2ccc(CONC(=O)c3cc(Oc4ccc(NC(=O)Nc5ccc(Cl)c(C(F)(F)F)c5)c(F)c4)ccn3)cc2)OC1(C)C] |

TABLE 6-continued
| Compound No. | Molecular formula | Structure |
|---|---|---|
| Compound 98 | C₂₇H₂₀BClF₄N₄O₆ | 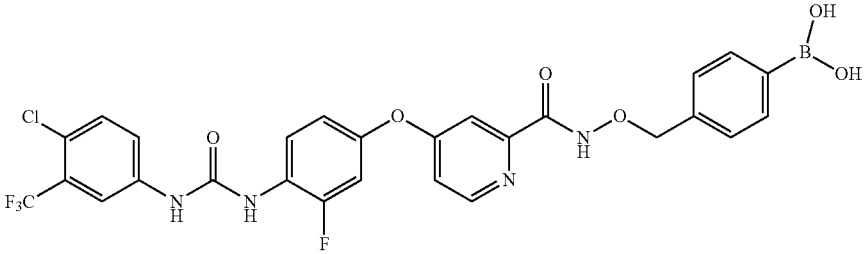 [SMILES: O=C(Nc1ccc(Cl)c(C(F)(F)F)c1)Nc1ccc(Oc2ccnc(C(=O)NOCc3ccc(B(O)O)cc3)c2)cc1F] |
| Compound 99 | C₃₃H₃₁BClF₃N₄O₆ | 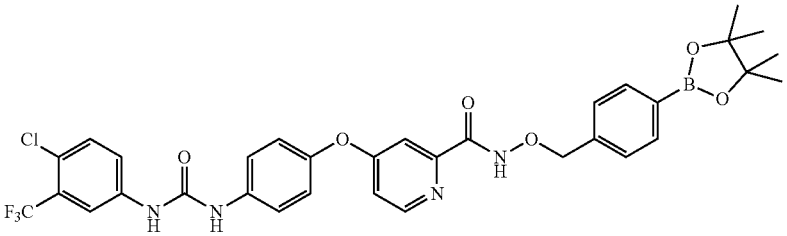 [SMILES: CC1(C)OB(c2ccc(CONC(=O)c3cc(Oc4ccc(NC(=O)Nc5ccc(Cl)c(C(F)(F)F)c5)cc4)ccn3)cc2)OC1(C)C] |
| Compound 100 | C₂₇H₂₁BClF₃N₄O₆ | 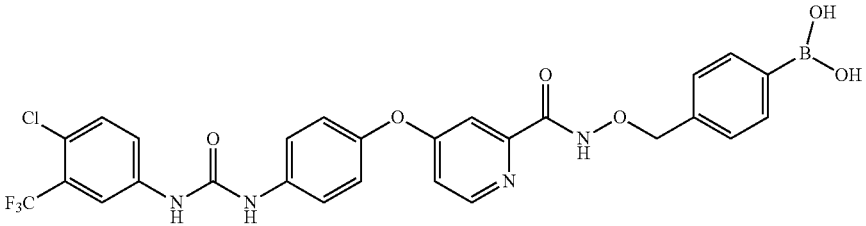 [SMILES: O=C(Nc1ccc(Oc2ccnc(C(=O)NOCc3ccc(B(O)O)cc3)c2)cc1)Nc1ccc(Cl)c(C(F)(F)F)c1] |
| Compound 101 | C₃₃H₃₁BF₄N₄O₅S | 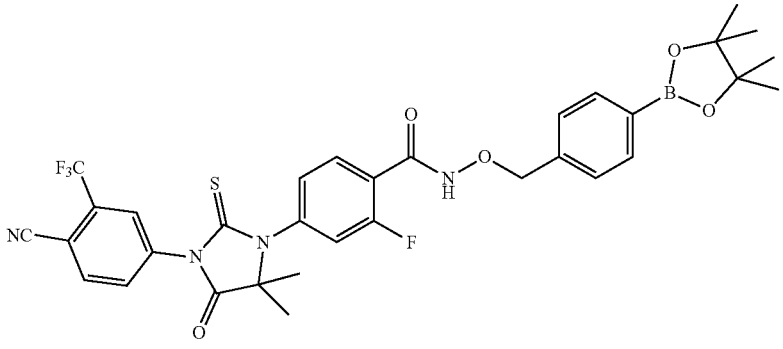 [SMILES: CC1(C)C(=O)N(c2ccc(C#N)c(C(F)(F)F)c2)C(=S)N1c1ccc(C(=O)NOCc2ccc(B3OC(C)(C)C(C)(C)O3)cc2)c(F)c1] |
| Compound 102 | C₂₇H₂₁BF₄N₄O₅S | 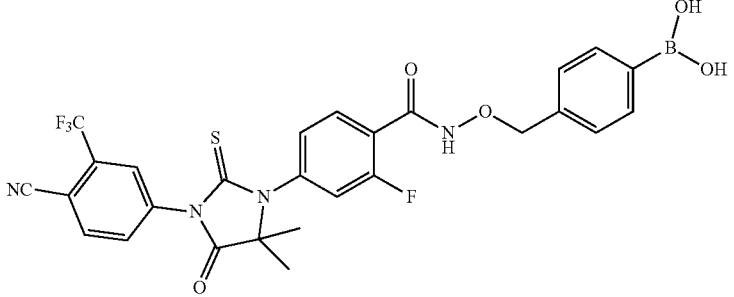 [SMILES: CC1(C)C(=O)N(c2ccc(C#N)c(C(F)(F)F)c2)C(=S)N1c1ccc(C(=O)NOCc2ccc(B(O)O)cc2)c(F)c1] |

TABLE 6-continued

| Compound No. | Molecular formula | Structure |
| --- | --- | --- |
| Compound 103 | C$_{29}$H$_{29}$BBrClFN$_3$O$_4$ | 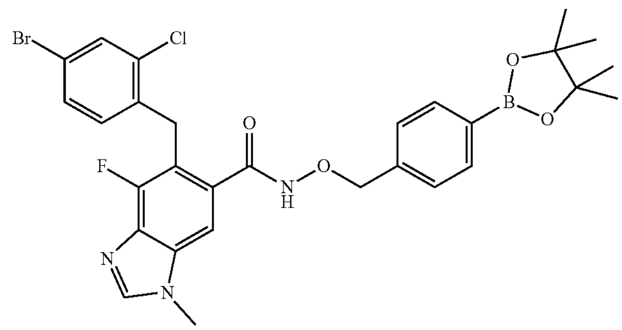 [SMILES: Cn1cnc2c(F)c(Cc3ccc(Br)cc3Cl)c(C(=O)NOCc3ccc(B4OC(C)(C)C(C)(C)O4)cc3)cc21] |
| Compound 104 | C$_{23}$H$_{19}$BBrClFN$_3$O$_4$ | 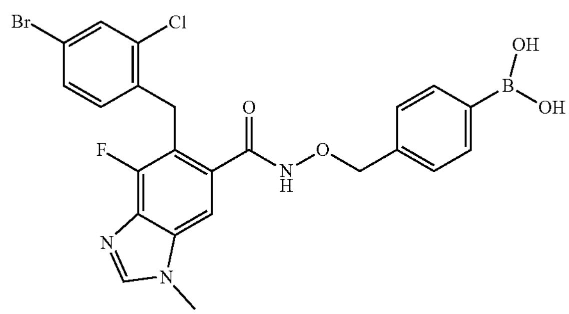 [SMILES: Cn1cnc2c(F)c(Cc3ccc(Br)cc3Cl)c(C(=O)NOCc3ccc(B(O)O)cc3)cc21] |
| Compound 105 | C$_{38}$H$_{43}$BF$_3$N$_3$O$_4$ | 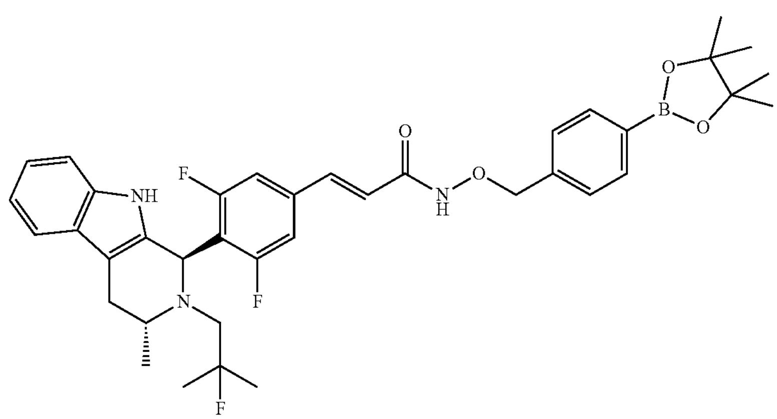 [SMILES: C[C@@H]1Cc2c([nH]c3ccccc23)[C@@H](c2c(F)cc(/C=C/C(=O)NOCc3ccc(B4OC(C)(C)C(C)(C)O4)cc3)cc2F)N1CC(C)(C)F] |
| Compound 106 | C$_{32}$H$_{33}$BF$_3$N$_3$O$_4$ | 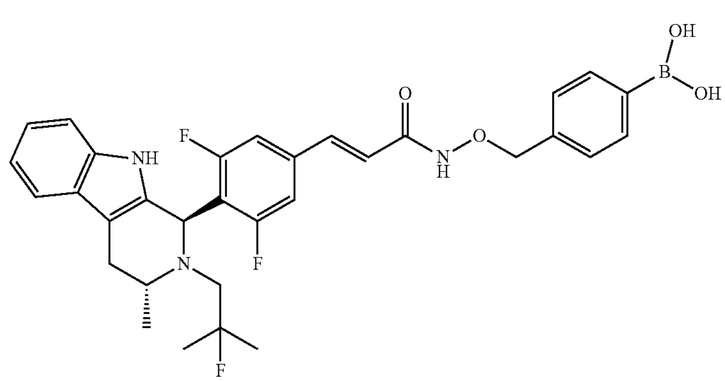 [SMILES: C[C@@H]1Cc2c([nH]c3ccccc23)[C@@H](c2c(F)cc(/C=C/C(=O)NOCc3ccc(B(O)O)cc3)cc2F)N1CC(C)(C)F] |

TABLE 6-continued

| Compound No. | Molecular formula | Structure |
| --- | --- | --- |
| Compound 107 | C₃₉H₃₈BClFN₃O₄ | 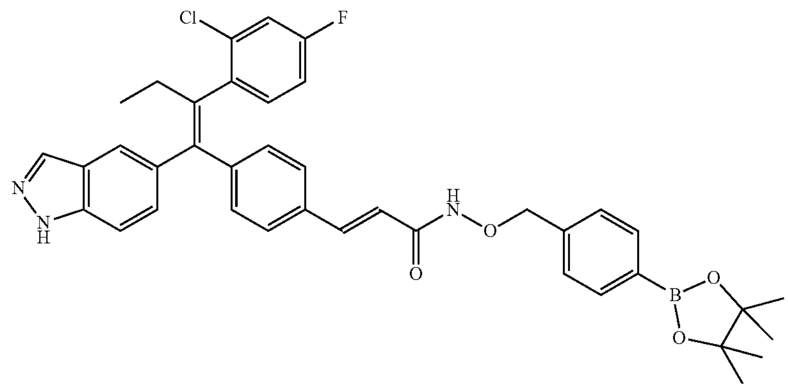 [SMILES: CC/C(=C(/c1ccc(/C=C/C(=O)NOCc2ccc(B3OC(C)(C)C(C)(C)O3)cc2)cc1)c1ccc2[nH]ncc2c1)c1ccc(F)cc1Cl] |
| Compound 108 | C₃₃H₃₈BClFN₃O₄ | 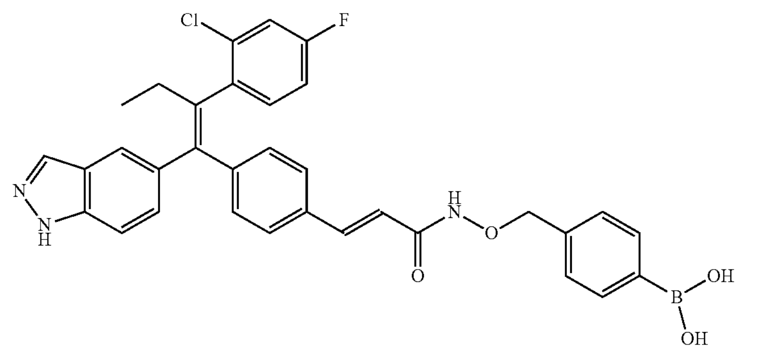 [SMILES: CC/C(=C(/c1ccc(/C=C/C(=O)NOCc2ccc(B(O)O)cc2)cc1)c1ccc2[nH]ncc2c1)c1ccc(F)cc1Cl] |
| Compound 109 | C₅₂H₅₅BClF₄N₇O₈S | 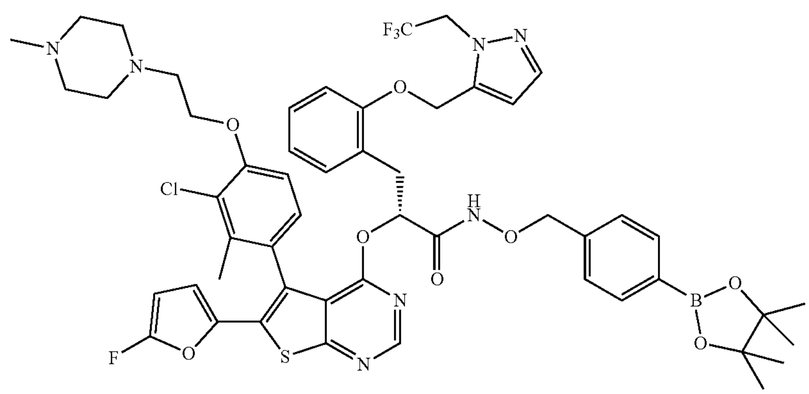 |
| Compound 110 | C₄₆H₄₅BClF₄N₇O₈S | 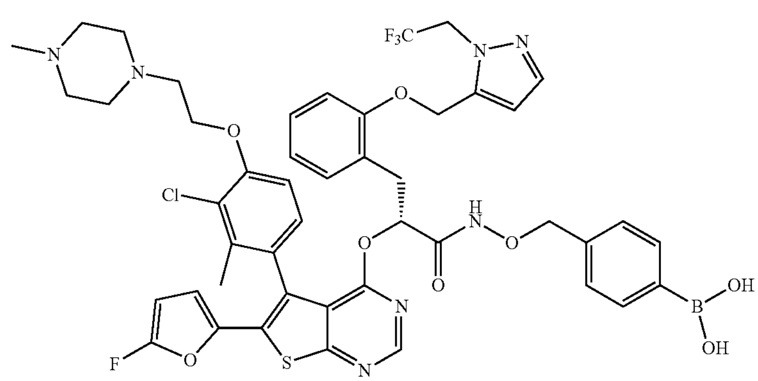 [SMILES: Cc1c(-c2c(-c3ccc(F)o3)sc3ncnc(O[C@H](Cc4ccccc4OCc4ccnn4CC(F)(F)F)C(=O)NOCc4ccc(B(O)O)cc4)c23)ccc(OCCN2CCN(C)CC2)c1Cl] |

TABLE 6-continued

| Compound No. | Molecular formula | Structure |
|---|---|---|
| Compound 111 | C₃₄H₃₆BClN₄O₇ | 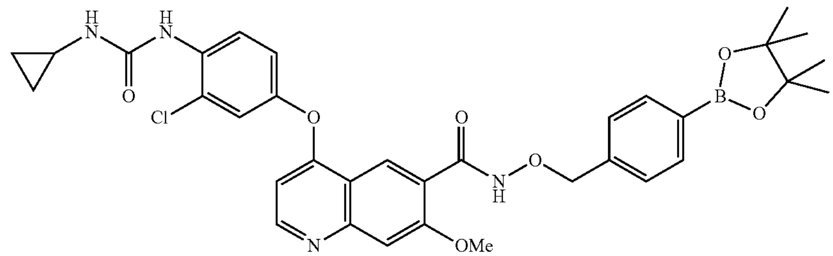 [SMILES: COc1cc2nccc(Oc3ccc(NC(=O)NC4CC4)c(Cl)c3)c2cc1C(=O)NOCc1ccc(B2OC(C)(C)C(C)(C)O2)cc1] |
| Compound 112 | C₂₈H₂₆BClN₄O₇ | 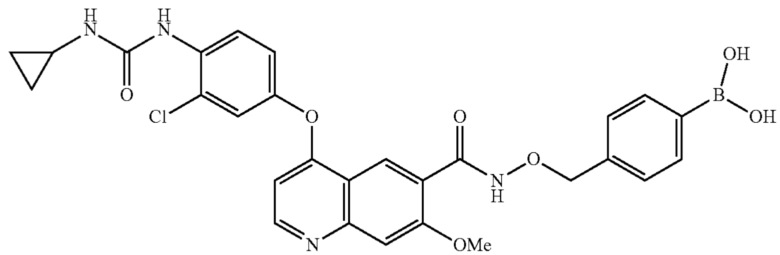 [SMILES: COc1cc2nccc(Oc3ccc(NC(=O)NC4CC4)c(Cl)c3)c2cc1C(=O)NOCc1ccc(B(O)O)cc1] |
| Compound 113 | C₂₃H₂₉BCl₂N₄O₄ | 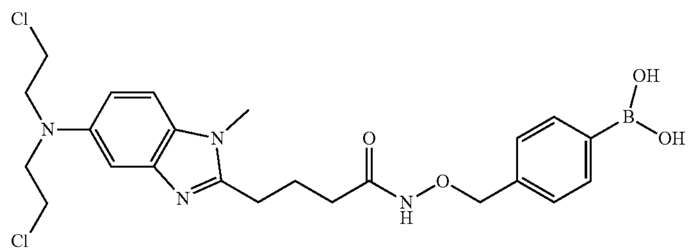 [SMILES: Cn1c(CCCC(=O)NOCc2ccc(B(O)O)cc2)nc2cc(N(CCCl)CCCl)ccc21] |
| Compound 114 | C₁₇H₂₀BNO₇ | 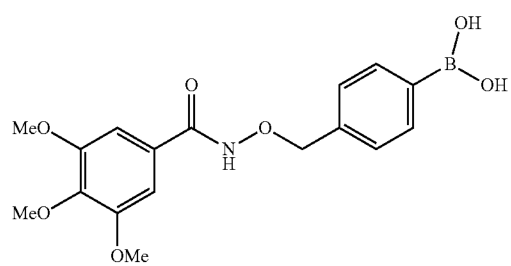 [SMILES: COc1cc(C(=O)NOCc2ccc(B(O)O)cc2)cc(OC)c1OC] |
| Compound 115 | C₁₅H₁₆BNO₅ | 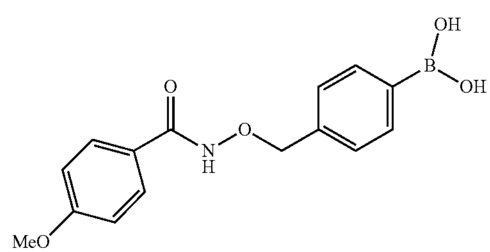 [SMILES: COc1ccc(C(=O)NOCc2ccc(B(O)O)cc2)cc1] |
| Compound 116 | C₁₆H₁₈BNO₆ | 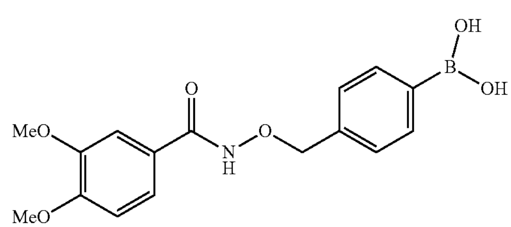 [SMILES: COc1ccc(C(=O)NOCc2ccc(B(O)O)cc2)cc1OC] |

TABLE 6-continued

| Compound No. | Molecular formula | Structure |
| --- | --- | --- |
| Compound 117 | $C_{18}H_{20}BNO_6$ | (structure: 3,4-dimethoxycinnamoyl-NH-O-CH₂-C₆H₄-B(OH)₂) |
| Compound 118 | $C_{17}H_{14}BNO_6$ | (structure: 2-oxo-2H-chromene-3-carbonyl-NH-O-CH₂-C₆H₄-B(OH)₂) |

Also provided is the use of at least one compound of Compounds 1 through 118 for treatment of a disease or symptom in a mammal in need thereof.

Also provided is a compound of Formulas 1 through 118 for use as a medicament, for use in the treatment of cancer in a mammal in need thereof, for use in providing epigenetic modulations in a mammal in need thereof.

In an embodiment, disease or symptom is selected from the group consisting of: a bacterial, viral, fungal, or *mycoplasma* infection; cancer; ulcer; Parkinson's disease; tuberculosis; leprosy; brucellosis; opioid addiction; arthritis; osteoarthritis; rheumatoid arthritis; leukemia; depression; cough or common cold; human immunodeficiency virus (HIV); anthrax; asthma; bronchitis; hypothyroidism; hypertension; hypotension; congestive heart failure; graft-versus-host disease; helminth infection; *Mycobacterium avium* complex (MAC) disease; ulcerative colitis; overactive bladder; urinary incontinence; and esophageal variceal bleeding.

A synthetic procedure for preparation of the boronic derivatives of hydroxamates involves condensation reaction of any substrates with carboxylic acid group and O-(4-(4,4,5,5-tetramethyl-1,3,2-dioxaborolan-2-yl)benzyl)hydroxylamine which was obtained from N-hydroxyphthalimide.

The below Examples will further illustrate the chemical structure of various embodiments of the boronic derivatives of hydroxamate compounds taught herein. Furthermore, the Examples demonstrate the efficacy of various embodiments of the disclosed boronic derivatives of hydroxamate compounds.

Example 5: Boron-Containing Derivatives of Vorinostat (Compound 1 and Compound 2)

Method A: Step 1. A mixture of N-hydroxyphthalimide (0.82 g, 5.0 mmol), 4-bromomethylphenyl boronic acid, pinacol ester (1.48 g, 5.0 mmol) and triethylamine (2 mL) was stirred at rt overnight. After reaction, the excess triethylamine was removed under vacuum. The residue was purified by flash chromatography to afford 1.39 g product. $^1$H-NMR (300 MHz, CDCl$_3$): 7.84-7.81 (m, 4H), 7.74 (m, 2H), 7.54 (d, J=7.8 Hz, 2H), 5.25 (s, 2H), 1.36 (s, 12H). $^{13}$C-NMR (75 MHz, CDCl3): 163.5, 136.5, 134.9, 134.4, 129.0, 128.9, 123.5, 83.9, 79.6, 24.9.

Step 2. To a solution of the product of Step 1 (0.38 g, 1 mmol) in ethanol, was added hydrazine monohydrate (0.05 g, 1 mmol). The mixture was stirred at room temperature overnight. The resulting precipitate was filtered off, and the filtrate was evaporated under vacuum. The residue was purified by flash chromatography to afford 0.20 g O-(4-(4,4,5,5-tetramethyl-1,3,2-dioxaborolan-2-yl)benzyl)hydroxylamine. $^1$H-NMR (300 MHz, CDCl$_3$): 7.81 (d, J=7.8 Hz, 2H), 7.23 (d, J=7.8 Hz, 2H), 5.40 (s, 2H), 4.71 (s, 2H), 1.35 (s, 12H). $^{13}$C-NMR (75 MHz, CDCl$_3$): 140.6, 135.0, 127.5, 83.8, 77.9, 24.9.

Step 3: The mixture of 8-oxo-8-(phenylamino)octanoic acid (0.045 g, 0.18 mmol), O-(4-(4,4,5,5-tetramethyl-1,3,2-dioxaborolan-2-yl)benzyl)hydroxylamine (0.045 g, 0.18 mmol), EDCI (0.035 g, 0.18 mmol) and pyridine (2 mL) was stirred at room temperature overnight. After reaction, the excess pyridine was removed under vacuum. The residue was purified by flash chromatography to afford 0.040 g compound 1 and 0.005 g free boronic acid of the product, compound 2. Compound 1: $^1$H-NMR (300 MHz, DMSO-d$_6$): 10.94 (s, 1H), 9.84 (s, 1H), 7.67 (d, J=7.8 Hz, 2H), 7.58 (d, J=8.1 Hz, 2H), 7.39 (d, J=8.1 Hz, 2H), 7.27 (t, J=7.8 Hz, 2H), 7.01 (t, J=7.2 Hz, 1H), 4.79 (s, 2H), 2.28 (t, J=7.2 Hz, 2H), 1.93 (t, J=6.9 Hz, 2H), 1.58-1.48 (m, 8H), 1.29 (s, 16H). $^{13}$C-NMR (75 MHz, DMSO-d6): 171.7, 169.8, 139.85, 139.81, 134.8, 129.1, 128.5, 123.4, 119.5, 84.2, 77.0, 36.8, 32.7, 28.8, 28.7, 25.4, 25.3, 25.1. HRMS (ESI) for $C_{27}H_{38}BN_2O_5$ (M+H): Calcd. 481.2874; Found 481.2862. Compound 2: $^1$H-NMR (300 MHz, DMSO-d6): 10.94 (s, 1H), 9.84 (s, 1H), 8.06 (s, 2H), 7.78 (d, J=7.2 Hz, 2H), 7.57 (d, J=7.8 Hz, 2H), 7.33 (d, J=7.5 Hz, 2H), 7.27 (m, 2H), 7.00 (m, 1H), 4.77 (s, 2H), 2.28 (t, J=6.9 Hz, 2H), 1.94 (t, J=6.6 Hz, 2H), 1.57-1.47 (m, 8H), 1.27 (m, 4H). $^{13}$C-NMR (75 MHz, DMSO-d6): 171.7, 169.8, 139.8, 138.3, 134.5, 129.1, 128.1, 123.4, 119.5, 77.2, 36.8, 32.7, 28.84, 28.76, 25.4, 25.3. HRMS (ESI) for $C_{21}H_{28}BN_2O_5$ (M+H): Calcd. 399.2091; Found 399.2098.

Method B: 80 mg of SAHA and 240 mg of the boronate ester were dissolved in 20 mL of methanol. To this solution 300 mg of $Cs_2CO_3$ was added. After half hour, 300 mg of boronate ester and 300 mg of KOH solid were added into the reaction solution. After another half and hour, another 300 mg of the boronate ester and 200 mg of KOH solid were added into the reaction solution. After 2.5 hour of last starting material addition, the reaction was quenched by concentrated HCl to pH 7-8. The mixture was concentrated under vacuum to remove all the solvent. The residue was dissolved in 100 mL of DCM. After filtration, to the filtrate 10 spoons of silica gel was added. The solvent was removed under vacuum. Using a 12 g silica gel column, an automatic column was run with DCM/methanol: 0%, 0%-5%, 5%, 5%-10%, 10%, 10%-100% for 30 min. 15 mg of Compound 1 (yield about 10%) and 6 mg of Compound 2 were obtained as colorless crystals.

Example 6: Pinacolyl Boronate Ester Derivatives of Belinostat (Compound 3)

The mixture of the methyl ester (0.32 g, 1 mmol), NaOH (0.04 g, 1 mmol) in 5 ml water was refluxed for 2 h, acidified with 1M HCl, then extracted with DCM and the combined organic layer was dried over MgSO$_4$. After filtering, the filtrate was added O-(4-(4,4,5,5-tetramethyl-1,3,2-dioxaborolan-2-yl)benzyl)hydroxylamine (0.26 g, 0.5 mmol) and triethylamine (0.5 mL). The resultant mixture was stirred at room temperature overnight+. After reaction, the solvent was removed under vacuum. The residue was purified by flash chromatography to afford 0.15 g compound 3. $^1$H-NMR (300 MHz, DMSO-d6): 11.34 (s, 1H), 10.32 (s, 1H), 7.91 (s, 1H), 7.79 (d, J=6.9 Hz, 1H), 7.70-7.69 (m, 3H), 7.60-7.42 (m, 5H), 7.22-7.20 (m, 2H), 7.09-7.03 (m, 3H), 6.46 (d, J=15.9 Hz, 1H), 4.90 (s, 2H), 1.29 (s, 12H). $^{13}$C-NMR (75 MHz, DMSO-d6): 162.8, 140.7, 139.7, 138.3, 137.9, 136.0, 134.9, 132.6, 130.5, 129.7, 128.6, 127.8, 125.5, 124.8, 121.2, 120.8, 84.2, 77.3, 25.1. HRMS (ESI) for C$_{28}$H$_{32}$BN$_2$O$_6$S (M+H): Calcd. 535.2074; Found 535.2070.

Example 7: Boron-Containing Derivative of Givinostat (Compound 4)

The mixture of the acid (0.16 g, 0.4 mmol), O-(4-(4,4,5,5-tetramethyl-1,3,2-dioxaborolan-2-yl)benzyl)hydroxylamine (0.09 g, 0.4 mmol), EDCI (0.1 g, 0.4 mmol) and pyridine (1.5 mL) in DCM was stirred at room temperature overnight. After reaction, the excess pyridine was removed under vacuum. The residue was purified by flash chromatography to afford 0.075 g compound 4. $^1$H-NMR (300 MHz, CDCl$_3$): 7.86-7.59 (m, 10H), 7.45-7.41 (m, 5H), 5.26 (s, 2H), 5.02 (s, 2H), 3.97 (s, 2H), 2.81 (q, J=6.9 Hz, 4H), 1.33 (s, 12H), 1.20 (t, J=6.9 Hz, 6H). $^{13}$C-NMR (75 MHz, CDCl$_3$): 165.7, 153.2, 141.6, 138.5, 135.0, 134.2, 132.9, 132.7, 130.9, 129.3, 128.8, 128.4, 128.3, 127.8, 127.0, 126.3, 126.2, 118.1, 83.9, 78.1, 67.0, 56.5, 46.2, 24.9, 9.6. HRMS (ESI) for C$_{37}$H$_{45}$BN$_3$O$_6$(M+H): Calcd. 638.3401; Found 638.3395.

Example 8: Boron-Containing Derivative of Resminostat (Compound 5 and Compound 6)

The mixture of the acid (0.23 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford compound 5 and its free boronic acid compound 6. $^1$H-NMR (300 MHz, CDCl3): 7.82-7.80 (m, 4H), 7.48-7.46 (m, 3H), 7.38 (d, J=7.5 Hz, 2H), 7.30-7.27 (m, 2H), 7.13 (s, 1H), 6.40 (s, 1H), 4.94 (s, 2H), 3.46 (s, 2H), 2.22 (s, 6H), 1.34 (s, 12H). HRMS (ESI) for C$_{29}$H$_{37}$BN$_3$O$_6$S (M+H): Calcd. 566.2496; Found 566.2488. Free acid: $^1$H-NMR (300 MHz, DMSO-d6): 11.26 (s, 1H), 8.16 (s, 2H), 7.96 (d, J=7.8 Hz, 2H), 7.78 (d, J=7.8 Hz, 2H), 7.73 (s, 1H), 7.63 (d, J=7.5 Hz, 2H), 7.97-7.89 (m, 3H), 7.39-7.31 (m, 4H), 6.58 (s, 1H), 6.15 (d, J=14.7 Hz, 1H), 4.83 (s, 2H), 3.63 (s, 2H), 2.23 (s, 6H).

Example 9: Boron-Containing Derivative of Bendamustine Hydroxamic Acid (Compound 7)

The mixture of bendamustine (0.14 g, 0.4 mmol), O-(4-(4,4,5,5-tetramethyl-1,3,2-dioxaborolan-2-yl)benzyl)hydroxylamine (0.10 g, 0.4 mmol), EDCI (0.09 g, 0.5 mmol) and pyridine (1 mL) in 10 mL of dichloromethane was stirred at room temperature overnight until the reaction finish completely. The reaction mixture was applied to a silica gel column and eluted with to afford 0.12 g compound 7 as yellow oil that solidifies on standing. $^1$H-NMR (300 MHz, DMSO-d6): 7.80 (d, J=7.5 Hz, 2H), 7.34 (d, J=7.8 Hz, 2H), 7.16 (d, J=8.7 Hz, 1H), 7.07 (d, J=1.8 Hz, 1H), 6.77 (dd, J=1.8 and 8.7 Hz, 1H), 5.11 (s, 2H), 3.73-3.62 (m, 11H), 2.88 (t, J=7.5 Hz, 2H), 2.55 (t, J=6.9 Hz, 2H), 2.20 (m, 2H), 1.34 (s, 12H). $^{13}$C-NMR (75 MHz, DMSO-d6): 172.9, 154.5, 143.8, 142.5, 138.9, 135.0, 129.6, 127.3, 110.6, 109.7, 103.4, 83.9, 66.1, 54.8, 40.8, 33.3, 29.7, 26.4, 24.9, 22.5. HRMS (ESI) for C$_{29}$H$_{40}$BCl$_2$N$_4$O$_4$ (M+H): Calcd. 589.2520; Found 589.2507.

Example 10: Boron-containing derivative of all-trans retinoic hydroxamic acid (Compound 8)

The mixture of the acid (0.13 g, 0.4 mmol), O-(4-(4,4,5,5-tetramethyl-1,3,2-dioxaborolan-2-yl)benzyl)hydroxylamine (0.10 g, 0.4 mmol), EDCI (0.09 g, 0.5 mmol) and pyridine (2 mL) in 20 mL of dichloromethane was stirred at room temperature overnight until the reaction finish completely. The reaction mixture was applied to a silica gel column and eluted with to afford compound 8 as yellow oil that solidifies on standing. $^1$H-NMR (300 MHz, DMSO-d6): 11.05 (s, 1H), 7.68 (d, J=7.2 Hz, 2H), 7.41 (d, J=7.2 Hz, 2H), 6.94 (m, 1H), 6.31-6.17 (m, 4H), 5.61 (s, 1H), 4.84 (s, 2H), 2.28 (s, 3H), 2.00-1.94 (m, 5H), 1.68 (s, 3H), 1.57 (m, 2H), 1.44 (m, 2H), 1.29 (s, 12H), 1.01 (s, 6H). $^{13}$C-NMR (75 MHz, DMSO-d6): 164.9, 148.2, 139.9, 138.7, 137.7, 137.5, 136.3, 135.9, 134.9, 130.5, 130.2, 129.8, 128.5, 127.9, 119.0, 84.2, 77.2, 34.3, 33.1, 29.3, 25.1, 22.0, 19.2, 13.0. HRMS (ESI) for C$_{33}$H$_{47}$BNO$_4$ (M+H): Calcd. 532.3598; Found 532.3589.

Example 11: Boron-Containing Derivative of 3,4-Dimethoxycinnamic Hydroxamic Acid (Compound 9)

The mixture of the acid (g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford compound 9. $^1$H-NMR (300 MHz, CDCl$_3$): 7.69 (d, J=7.8 Hz, 2H), 7.44-7.42 (m, 3H), 7.15-7.11 (m, 2H), 6.97 (d, J=8.1 Hz, 1H), 6.31 (d, J=14.7 Hz, 2H), 4.89 (s, 2H), 3.78 (s, 6H), 1.29 (s, 12H). $^{13}$C-NMR (75 MHz, DMSO-d6): 163.9, 150.8, 149.3, 140.2, 139.9, 134.9, 128.5, 127.8, 122.1, 116.5, 112.1, 110.4, 84.2, 77.2, 74.0, 60.2, 56.0, 55.9, 25.1.

Example 12: Boron-Containing Derivative of 4-Methoxyhydrobenzoic Hydroxamic Acid (Compound 10)

The mixture of the acid (0.076 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford 0.050 g compound 10. $^1$H-NMR (300 MHz, CDCl$_3$): 8.34 (s, 1H), 7.84 (d, J=7.5 Hz, 2H), 7.62 (d, J=8.7 Hz, 2H), 7.45 (d, J=8.1 Hz, 2H), 6.88 (d, J=8.4 Hz, 2H), 5.04 (s, 2H), 3.83 (s, 31), 1.35 (s, 12H). $^{13}$C-NMR (75 MHz, CDCl$_3$): 166.3, 162.7, 138.4, 135.1, 128.9, 128.5, 124.1, 114.0, 84.0, 78.2, 55.4, 24.9. HRMS (ESI) for C$_{21}$H$_{27}$BNO$_5$ (M+H): Calcd. 384.1982; Found 384.1976.

Example 13: Boron-Containing Derivative of Sulindac Hydroxamic Acid (Compound 11)

The mixture of the acid (0.18 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford compound 11. $^1$H-NMR (300 MHz, CDCl$_3$): 8.05 (br s, 1H), 7.76-7.67 (m, 6H), 7.28 (d, J=9.0 Hz, 2H), 7.16 (d, J=9.0 Hz, 2H), 6.80 (d, J=7.5 Hz, 1H), 6.59 (m, 1H), 4.90 (s, 2H), 3.47 (s, 2H), 2.83 (s, 3H), 2.13 (s, 3H), 1.35 (s, 12H). $^{13}$C-NMR (75 MHz, DMSO-d6): 167.0, 163.6 (d, J=242 Hz), 148.1, 147.3, 141.4, 140.2, 139.6, 139.3, 135.4, 133.7, 131.0, 130.6, 130.4, 129.3, 125.0, 124.2, 111.5 (d, J=23.3 Hz), 107.3 (d, J=22.2 Hz), 84.7, 77.6, 44.2, 30.8, 25.7, 11.4. HRMS (ESI) for C$_{33}$H$_{36}$BFNO$_5$S (M+H): Calcd. 588.2391; Found 588.2388.

Example 14: Boron-Containing Derivative of Pracinostat (Compound 12)

The methyl ester (0.18 g, 0.5 mmol) with potassium hydroxide in water was irradiated under microwave at 100° C. for 2 h until the reaction mixture turn into the clear solution. The solution was neutralized with 10% HCl until pH=3-4. The solvent was removed under vacuum at 50° C., diluted with DCM and dried over molecular sieve. EDCI (0.096 g, 0.5 mmol) and pyridine (1 mL) were added and the resultant mixture was stirred for 10 min, then O-(4-(4,4,5,5-tetramethyl-1,3,2-dioxaborolan-2-yl)benzyl)hydroxylamine (0.13 g, 0.5 mmol) was added and the mixture was stirred at rt overnight. After reaction, the solution was washed with satd. NH$_4$Cl and brine. The organic layer was separated, dried over MgSO4 and concentrated. The residue was purified by flash chromatography to afford compound 12. $^1$H-NMR (400 MHz, CDCl$_3$): 7.89-7.83 (m, 4H), 7.44-7.38 (m, 3H), 7.28-7.25 (m, 2H), 4.99 (s, 2H), 4.15 (t, J=8.0 Hz, 2H), 2.89 (t, J=4.0 Hz, 2H), 2.73 (t, J=8.0 HZ, 2H), 2.55 (q, J=8.0 Hz, 4H), 1.88 (m, 2H), 1.48 (m, 2H), 1.34 (s, 12H), 0.97 (m, 9H).

Example 15: Boron-Containing Derivative of 3,4,5-Trimethoxybenzoic Hydroxamic Acid (Compound 13)

The mixture of the acid (0.10 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford compound 13. $^1$H-NMR (300 MHz, CDCl$_3$): 8.34 (s, 1H), 7.84 (d, J=7.8 Hz, 2H), 7.46 (d, J=7.8 Hz, 2H), 6.85 (s, 2H), 5.06 (s, 2H), 3.86 (s, 9H), 1.35 (s, 12H). $^{13}$C-NMR (75 MHz, DMSO-d6): 166.3, 153.3, 141.4, 138.2, 135.1, 128.6, 127.2, 104.4, 84.0, 78.2, 60.9, 56.3, 24.9. HRMS (ESI) for C$_{23}$H$_{31}$BNO$_7$ (M+H): Calcd. 444.2194; Found 444.2184.

Example 16: Boron-containing derivative of ibuprofen hydroxamic acid (Compound 14)

The mixture of the acid (0.12 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford 0.10 g compound 14. $^1$H-NMR (300 MHz, CDCl$_3$): 7.83-7.74 (m, 3H), 7.35-7.25 (m, 2H), 7.10-7.05 (m, 4H), 4.85 (s, 2H), 3.39 (m, 1H), 2.43 (d, J=6.9, 2H0, 1.83 (m, 1H), 1.49 (d, J=6.9 Hz, 3H), 1.35 (s, 12H), 0.89 (d, J=6.6 Hz, 6H). 1H-NMR (300 MHz, DMSO-d6): 11.17 (s, 1H), 7.63 (d, J=6.9 Hz, 2H), 7.30 (d, J=7.5 Hz, 2H), 7.16 (d, J=7.5 Hz, 2H), 7.06 (d, J=7.8 Hz, 2H), 4.75 (s, 2H), 2.39 (d, J=6.9 Hz, 2H), 1.80 (m, 1H), 1.29 (s, 15H), 0.85 (d, J=6.3 Hz, 6H). $^{13}$C-NMR (75 MHz, DMSO-d6): 170.9, 139.9, 139.6, 139.0, 134.8, 129.3, 128.7, 127.4, 84.1, 76.8, 44.7, 42.1, 30.1, 25.1, 22.6, 18.5. HRMS (ESI) for C$_{26}$H$_{37}$BNO$_4$ (M+H): Calcd. 438.2816; Found 438.2816.

Example 17: Boron-Containing Derivative of 2-Oxo-2H-Chromene-3-Carboxylic Hydroxamic Acid (Compound 15)

The mixture of the acid (0.095 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford 0.094 g compound 15. $^1$H-NMR (300 MHz, CDCl$_3$): 10.98 (s, 1H), 8.95 (s, 1H), 7.85 (d, J=7.8 Hz, 2H), 7.73-7.67 (m, 2H), 7.47 (d, J=7.8 Hz, 2H), 7.43-7.39 (m, 2H), 5.08 (s, 2H), 1.36 (s, 12H). $^{13}$C-NMR (75 MHz, CDCl$_3$): 160.7, 159.5, 154.4, 148.9, 137.9, 135.1, 134.5, 129.9, 128.3, 125.5, 118.4, 117.7, 116.8, 83.9, 78.4, 24.9. HRMS (ESI) for C$_{23}$H$_{31}$BNO$_7$ (M+H): Calcd. 444.2194; Found 444.2184.

Example 18: Boron-Containing Derivative of 3,4-Dimethoxybenzoic Hydroxamic Acid (Compound 16)

The mixture of the acid (0.09 g, 0.5 mmol), O-(4-(4,4,5,5-tetramethyl-1,3,2-dioxaborolan-2-yl)benzyl)hydroxylamine (0.13 g, 0.5 mmol), EDCI (0.10 g, 0.5 mmol) and pyridine (3 mL) in DCM was stirred at room temperature for overnight. After reaction, the solvent was removed under vacuum. The residue was purified by flash chromatography to afford 0.086 g compound 16. $^1$H-NMR (300 MHz, CDCl$_3$): 8.46 (s, 1H), 7.85 (d, J=7.8 Hz, 2H), 7.46 (d, J=7.8 Hz, 2H), 7.33 (s, 1H), 7.13 (d, J=8.1 Hz, 1H), 6.81 (d, J=8.1 Hz, 1H), 5.06 (s, 21), 3.91 (s, 6H), 1.37 (s, 12H). $^{13}$C-NMR (75 MHz, CDCl3): 166.3, 152.3, 149.2, 138.3, 135.1, 128.5, 124.4, 119.6, 110.5, 110.3, 84.0, 78.2, 56.1, 56.0, 24.9. HRMS (ESI) for $C_{22}H_{29}BNO_6$ (M+H): Calcd. 414.2088; Found 414.2077.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A compound of Formula (XIa)

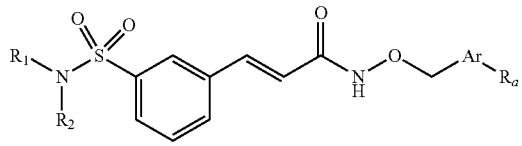

wherein:

$R_a$ is selected from the group consisting of:

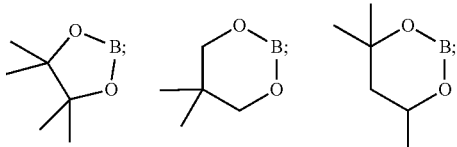

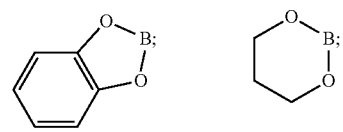

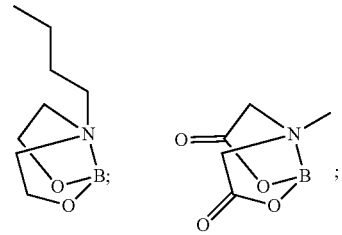

$KF_3B$;

$(HO)_2B$; and $NaF_3B$; Ar is substituted or substituted aryl or heteroaryl; and each of $R_1$ and $R_2$ are independently the same as or different from each other and are a hydrogen atom, a substituted or unsubstituted phenyl, benzyl, phenylalkyl, naphthyl, naphthylalkyl, 2-pyridinyl, 2-pyridinylalkyl, 3-pyridinyl, 3-pyridinylalkyl, 4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl, or isoquinolinyl.

2. The compound of claim 1, wherein $R_a$ is

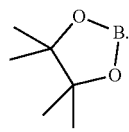

3. The compound of claim 1, wherein $R_a$ is:

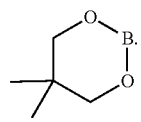

4. The compound of claim 1, wherein $R_a$ is:

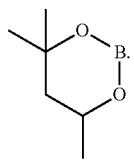

5. The compound of claim 1, wherein $R_a$ is:

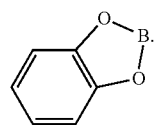

6. The compound of claim 1, wherein $R_a$ is:

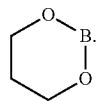

7. The compound of claim 1, wherein $R_a$ is:

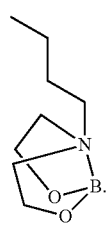

8. The compound of claim 1, wherein $R_a$ is:

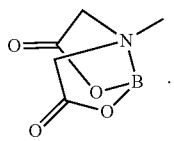

9. The compound of claim 1, wherein $R_a$ is: $KF_3B$.

10. The compound of claim 1, wherein $R_a$ is: $(HO)_2B$.

11. The compound of claim 1, wherein $R_a$ is: $NaF_3B$.

12. A method for the treatment of breast cancer in a patient in need thereof, the method comprising administering a therapeutically effective amount of a compound of claim 1 to the patient.

13. A method for treatment of non-small-cell lung cancer in a patent in need thereof, the method comprising administering a therapeutically effective amount of a compound of claim 1 to the patient.

14. A method for treatment of cervical cancer in a patent in need thereof, the method comprising administering a therapeutically effective amount of a compound of claim 1 to the patient.

15. The compound of claim 1, wherein said compound is (E)-3-(3-(N-phenylsulfamoyl)phenyl)-N-((4-(4,4,5,5-tetramethyl-1,3,2-dioxaborolan-2-yl)benzyl)oxy)acrylamide.

16. The compound of claim 1, wherein the compound of Formula (XIa) is the compound of Formula (XIb):

(XIb)

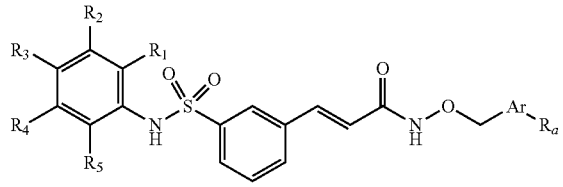

wherein:
$R_a$ is selected from the group consisting of:

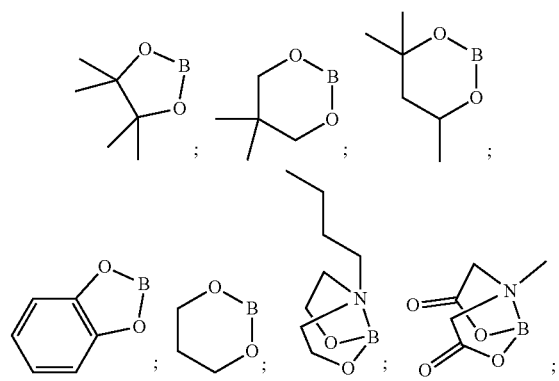

$KF_3B$; $(HO)_2B$; and $NaF_3B$; Ar is a substituted or unsubstituted aryl or heteroaryl; and each of $R_1$, $R_2$, $R_3$, $R_4$, and $R_5$ are independently the same as or different from each other and are a hydrogen atom, methyl, methoxy, phenyl, chloro, bromo, fluoro, iodo, difluoromethyl, trifluoromethyl, difluoromethoxy, trifluoromethoxy, nitro, nitrile, acetyl, acyl, alkylthio, isopropyl, isobutyl, tert-butyl, a substituted or unsubstituted phenyl, benzyl, phenylalkyl, naphthyl, naphthylalkyl, 2-pyridinyl, 2-pyridinylalkyl, 3-pyridinyl, 3-pyridinylalky 1,4-pyridinyl, 4-pyridinylalkyl, thiazolyl, 2-furanyl, 2-furanylalkyl, hydroxyl, branched or unbranched alkyl, alkenyl, alkyloxy, aryloxy, arylalkyloxy, arylalkenyl, indolyl, indolylalkyl, imidazolyl, imidazolylalkyl, quinolinyl, or isoquinolinyl.

17. A method for treatment of melanoma in a patient in need thereof, the method comprising administering a therapeutically effective amount of a compound of claim 1 to the patient.

18. A method for treatment of ovarian cancer in a patient in need thereof, the method comprising administering a therapeutically effective amount of a compound of claim 1 to the patient.

19. A method for treatment of cyctic fibrosis in a patient in need thereof, the method comprising administering a therapeutically effective amount of a compound of claim 1 to the patient.

* * * * *